US011407830B2

(12) United States Patent
Jenkins et al.

(10) Patent No.: US 11,407,830 B2
(45) Date of Patent: Aug. 9, 2022

(54) METHODS OF TREATING CANCER WITH ANTI-PD-1 ANTIBODIES

(71) Applicant: TESARO, INC., Waltham, MA (US)

(72) Inventors: David Jenkins, Waltham, MA (US); Haley A Laken, Waltham, MA (US); Ellie Im, Waltham, MA (US); Allene Diaz, Waltham, MA (US); Sharon Lu, Waltham, MA (US)

(73) Assignee: Tesaro, Inc., Waltham, MA (US)

( * ) Notice: Subject to any disclaimer, the term of this patent is extended or adjusted under 35 U.S.C. 154(b) by 225 days.

(21) Appl. No.: 16/476,536

(22) PCT Filed: Jan. 9, 2018

(86) PCT No.: PCT/US2018/013029
§ 371 (c)(1),
(2) Date: Jul. 8, 2019

(87) PCT Pub. No.: WO2018/129559
PCT Pub. Date: Jul. 12, 2018

(65) Prior Publication Data
US 2020/0239574 A1 Jul. 30, 2020

Related U.S. Application Data

(60) Provisional application No. 62/556,386, filed on Sep. 9, 2017, provisional application No. 62/491,220, filed on Apr. 27, 2017, provisional application No. 62/477,423, filed on Mar. 27, 2017, provisional application No. 62/444,336, filed on Jan. 9, 2017.

(51) Int. Cl.
*A61K 39/395* (2006.01)
*C07K 16/28* (2006.01)
*A61P 35/00* (2006.01)
*A61K 39/00* (2006.01)

(52) U.S. Cl.
CPC ........ *C07K 16/2818* (2013.01); *A61K 39/395* (2013.01); *A61P 35/00* (2018.01); *A61K 2039/505* (2013.01); *A61K 2039/545* (2013.01); *C07K 2317/24* (2013.01); *C07K 2317/76* (2013.01)

(58) Field of Classification Search
CPC combination set(s) only.
See application file for complete search history.

(56) References Cited

U.S. PATENT DOCUMENTS

| | | | |
|---|---|---|---|
| 5,122,464 A | 6/1992 | Wilson et al. | |
| 5,464,758 A | 11/1995 | Gossen et al. | |
| 5,770,359 A | 6/1998 | Wilson et al. | |
| 5,814,618 A | 9/1998 | Bujard et al. | |
| 7,029,674 B2 | 4/2006 | Carreno et al. | |
| 7,101,550 B2 | 9/2006 | Wood et al. | |
| 7,105,328 B2 | 9/2006 | Wood | |
| 7,112,715 B2 | 9/2006 | Chambon et al. | |
| 7,414,171 B2 | 8/2008 | Honjo | |
| 7,488,802 B2 | 2/2009 | Collins et al. | |
| 7,595,048 B2 | 9/2009 | Honjo et al. | |
| 7,700,301 B2 | 4/2010 | Wood et al. | |
| 7,709,214 B2 | 5/2010 | Freeman et al. | |
| 8,008,449 B2 | 8/2011 | Korman et al. | |
| 8,088,905 B2 | 1/2012 | Collins et al. | |
| 8,168,757 B2 | 5/2012 | Finnefrock et al. | |
| 8,216,996 B2 | 7/2012 | Minato | |
| 8,460,886 B2 | 6/2013 | Shibayama | |
| 8,563,314 B2 | 10/2013 | Gregory | |
| 8,586,038 B2 | 11/2013 | Yang | |
| 8,609,625 B2 | 12/2013 | Lan | |
| 8,728,474 B2 | 5/2014 | Honjo et al. | |
| 8,927,697 B2 | 1/2015 | Davis et al. | |
| 8,993,731 B2 | 3/2015 | Tyson et al. | |
| 9,102,728 B2 | 8/2015 | Tyson | |
| 9,181,342 B2 | 11/2015 | Davis | |
| 9,815,897 B2 | 11/2017 | King et al. | |
| 10,738,117 B2 | 8/2020 | King et al. | |
| 11,155,624 B2 | 10/2021 | King et al. | |
| 2002/0100068 A1 | 7/2002 | Chambon et al. | |
| 2002/0164600 A1 | 11/2002 | Freeman | |
| 2004/0213795 A1 | 10/2004 | Collins et al. | |
| 2004/0241745 A1 | 12/2004 | Honjo | |
| 2007/0041982 A1 | 2/2007 | Ponath et al. | |
| 2007/0092504 A1 | 4/2007 | Carreno | |
| 2008/0311117 A1 | 12/2008 | Collins | |
| 2009/0028857 A1 | 1/2009 | Li | |
| 2009/0060924 A1 | 3/2009 | Korytko et al. | |
| 2009/0093024 A1 | 4/2009 | Bowers et al. | |

(Continued)

FOREIGN PATENT DOCUMENTS

| | | |
|---|---|---|
| CA | 2932966 | 6/2015 |
| EP | 2397155 | 12/2011 |

(Continued)

OTHER PUBLICATIONS

Agrawal et al (Journal for ImmunoTherapy of Cancer, 2016, 4:72, internet pp. 1-11).*
Ott et al (Journal of Clinical Oncology, May 20, 2016, 34: No. 15_suppl, abstract 5581).*
Fader et al. (Gynecologic Oncology, 2016, 141:p. 206-207, # 3).*
Wang et al. (Chapter 9 in "ADME and Translational Pharmakokinetics/ Pharmacodynamics of Therapeutic Proteins: Applications in Drug Discovery and Development", First Edition edited by Honghui Zhou and Frank-Peter Theil; Published 2016 by John Wiley & Sons, Inc.).*

(Continued)

*Primary Examiner* — Laura B Goddard
(74) *Attorney, Agent, or Firm* — Fish & Richardson P.C.

(57) ABSTRACT

The present invention provides methods of administering certain PD-1 binding agents to patients having cancer. Dosage regimens for compositions comprising a PD-1 binding agent are also explicitly provided.

16 Claims, 8 Drawing Sheets

Specification includes a Sequence Listing.

(56) References Cited

U.S. PATENT DOCUMENTS

| | | |
|---|---|---|
| 2010/0028330 A1 | 2/2010 | Collins et al. |
| 2010/0086550 A1 | 4/2010 | Kang |
| 2010/0151492 A1 | 6/2010 | Ahmed |
| 2011/0008369 A1 | 1/2011 | Finnefrock et al. |
| 2011/0081341 A1 | 4/2011 | Honjo |
| 2011/0150892 A1 | 6/2011 | Thudium et al. |
| 2011/0171215 A1 | 7/2011 | Davis et al. |
| 2011/0171220 A1 | 7/2011 | Davis |
| 2011/0229461 A1 | 9/2011 | Tyson |
| 2011/0287485 A1 | 11/2011 | Bowers et al. |
| 2012/0039906 A1 | 2/2012 | Olive |
| 2012/0114649 A1 | 5/2012 | Langermann |
| 2012/0269806 A1 | 10/2012 | Sykes et al. |
| 2013/0035472 A1 | 2/2013 | Horlick et al. |
| 2013/0095098 A1 | 4/2013 | Tyson |
| 2013/0109843 A1 | 5/2013 | Carven |
| 2013/0133091 A1 | 5/2013 | Korman |
| 2013/0156774 A1 | 6/2013 | Kuchroo |
| 2013/0164294 A1 | 6/2013 | Honjo |
| 2013/0202623 A1 | 8/2013 | Chomont |
| 2013/0217656 A1 | 8/2013 | Tsokos |
| 2013/0291136 A1 | 10/2013 | Freeman |
| 2013/0309250 A1 | 11/2013 | Cogswell |
| 2013/0310266 A1 | 11/2013 | Liang |
| 2014/0004081 A1 | 1/2014 | Cobbold |
| 2014/0220021 A1 | 8/2014 | Shibayama et al. |
| 2015/0125955 A1 | 5/2015 | Chomont et al. |
| 2015/0152180 A1 | 6/2015 | Davis et al. |
| 2015/0203579 A1 | 7/2015 | Papadopoulos et al. |
| 2015/0210769 A1 | 7/2015 | Freeman et al. |
| 2015/0274844 A1 | 10/2015 | Blankenship et al. |
| 2015/0366174 A1 | 12/2015 | Burova et al. |
| 2016/0068586 A1 | 3/2016 | Tyson |
| 2016/0176962 A1 | 6/2016 | Murriel |
| 2016/0206754 A1 | 7/2016 | Chang |
| 2016/0208021 A1 | 7/2016 | Chang |
| 2016/0304607 A1* | 10/2016 | Sadineni ............... A61K 47/18 |
| 2019/0256600 A1* | 8/2019 | King ...................... A61P 35/00 |
| 2020/0239574 A1 | 7/2020 | Jenkins et al. |

FOREIGN PATENT DOCUMENTS

| | | |
|---|---|---|
| EP | 2638061 | 9/2013 |
| JP | 2018-515474 | 6/2018 |
| TW | 201825512 | 7/2018 |
| WO | WO 1992/008796 | 5/1992 |
| WO | WO 1994/028143 | 12/1994 |
| WO | WO 2001/014557 | 3/2001 |
| WO | WO 2002/078731 | 10/2002 |
| WO | WO 2003/042402 | 5/2003 |
| WO | WO 2004/056875 | 7/2004 |
| WO | WO 2008/083174 | 7/2008 |
| WO | WO 2008/084261 | 7/2008 |
| WO | WO 2008/156712 | 12/2008 |
| WO | WO 2009/026472 | 2/2009 |
| WO | WO 2009/087381 | 7/2009 |
| WO | WO 2010/029434 | 3/2010 |
| WO | WO 2010/029435 | 3/2010 |
| WO | WO 2011/090762 | 7/2011 |
| WO | WO 2011/100841 | 8/2011 |
| WO | WO 2011/110604 | 9/2011 |
| WO | WO 2011/110621 | 9/2011 |
| WO | WO 2012/017003 | 2/2012 |
| WO | WO 2012/135408 | 10/2012 |
| WO | WO 2013/022091 | 2/2013 |
| WO | WO 2013/128194 | 9/2013 |
| WO | WO 2013/169693 | 11/2013 |
| WO | WO 2013/174997 | 11/2013 |
| WO | WO 2013/177102 | 11/2013 |
| WO | WO 2013/181452 | 12/2013 |
| WO | WO 2014/179664 * | 11/2014 |
| WO | WO2014/179664 A2 | 11/2014 |
| WO | WO 2015/112800 | 7/2015 |
| WO | WO 2015/112900 | 7/2015 |
| WO | WO 2015/13 8920 | 9/2015 |
| WO | WO 2015/145360 | 10/2015 |
| WO | WO 2015/196051 | 12/2015 |
| WO | WO 2016/020856 | 2/2016 |
| WO | WO 2016/054555 | 4/2016 |
| WO | WO 2016/100882 | 6/2016 |
| WO | WO 2016/100924 | 6/2016 |
| WO | WO 2016/106159 | 6/2016 |
| WO | WO 2016/109310 | 7/2016 |
| WO | WO 2016/112870 | 7/2016 |
| WO | WO 2016/126858 | 9/2016 |
| WO | WO 2016/161270 | 10/2016 |
| WO | WO 2016/176504 | 11/2016 |
| WO | WO 2017/019894 | 11/2017 |
| WO | WO 2018/005818 | 1/2018 |
| WO | WO 2018/129553 | 7/2018 |
| WO | WO 2018/129559 | 7/2018 |
| WO | WO 2019/067978 | 4/2019 |

OTHER PUBLICATIONS

Konstantinopoulos et al (J Clinical Oncology, May 20, 2016, 34, No. 15_suppl, abstract TPS5599).*

ClinicalTrials.gov NCT02716284, "A Phase 1 Dose Escalation and Cohort Expansion Study of TSR-042, an Anti-PD-1 Monoclonal Antibody, in Patients With Advanced Tumors", published online Aug. 10, 2016.* clinicaltrails.gov [online], "NCT03955471: Study to Evaluate the Efficacy and Safety of the Combination of Niraparib and Dostarlimab (TSR-042) in Participants With Platinum Resistant Ovarian Cancer (Moonstone)", U.S. National Library of Medicine, May 20, 2019, retrieved on Jul. 22, 2021, retrieved on URL <"https://clinicaltrials.gov/ct2/show/NCT03955471">, 12 pages.

clinicaltrails.gov [online], "NCT04544995: Dose Escalation and Cohort Expansion Study of Niraparib and Dostarlimab in Pediatric Participants With Solid Tumors", U.S. National Library of Medicine, Sep. 10, 2020, retrieved on Jul. 22, 2021, retrieved from URL: <"https://clinicaltrials.gov/ct2/show/NCT04544995">, 11 pages.

clinicaltrial.gov [online], "NCT04679064: Trial on NIraparib-TSR-042 (Dostarlimab) vs Physician's Choice CHEmotherapy in Recurrent, Ovarian, Fallopian Tube or Primary Peritoneal Cancer Patients Not Candidate for Platinum Retreatment (NItCHE-MITO33)", Dec. 22, 2020, retrieved on Jul. 22, 2021, retrieved from URL <"https://clinicaltrials.gov/ct2/show/NCT04679064">, 11 pages.

clinicaltrial.gov [online], "NCT04926324: A Safety Study Adding Niraparib and Dostarlimab to Radiation Therapy for Rectal Cancers (Topaz)", U.S. National Library of Medicine, Jun. 15, 2021, retrieved on Jul. 22, 2021, retrieved from URL <"https://clinicaltrials.gov/ct2/show/NCT04926324">, 11 pages.

clinicaltrials.gov [online], "NCT02715284: Study of TSR-042, an Anti-programmed Cell Death-1 Receptor (PD-1) Monoclonal Antibody, in Participants With Advanced Solid Tumors (Garnet)", U.S. National Library of Medicine, Mar. 22, 2016, retrieved on Jul. 22, 2021, retrieved from URL <"https://clinicaltrials.gov/ct2/show/NCT02715284">, 24 pages.

clinicaltrials.gov [online], "NCT02817633: A Study of TSR-022 in Participants With Advanced Solid Tumors (Amber)", U.S. National Library of Medicine, Jun. 29, 2016, retrieved on Jul. 22, 2021, retrieved from URL <"https://clinicaltrials.gov/ct2/show/NCT02817633">, 15 pages.

clinicaltrials.gov [online], "NCT03250832: Study of TSR-033 With an Anti-programmed Cell Death-1 Receptor (PD-1) in Participants With Advanced Solid Tumors (Citrino)", U.S. National Library of Medicine, Aug. 16, 2017, retrieved on Jul. 22, 2021, retrieved on URL <"https://clinicaltrials.gov/ct2/show/NCT03250832">, 24 pages.

clinicaltrials.gov [online], "NCT03308942: Effects of Single Agent Niraparib and Niraparib Plus Programmed Cell Death-1 (PD-1) Inhibitors in Non-Small Cell Lung Cancer Participants", U.S. National Library of Medicine, Oct. 13, 2017, retrieved from Jul. 22, 2021, retrieved from URL <"https://clinicaltrials.gov/ct2/show/NCT03308942">, 20 pages.

clinicaltrials.gov [online], "NCT03602859: A Phase 3 Comparison of Platinum-based Therapy With TSR-042 and Niraparib Versus Standard of Care (SOC) Platinum-based Therapy as First-line

(56) References Cited

OTHER PUBLICATIONS

Treatment of Stage III or IV Nonmucinous Epithelial Ovarian Cancer (First)", U.S. National Library of Medicine, Jul. 27, 2018, retrieved on Jul. 22, 2021, retrieved from URL <"https://clinicaltrials.gov/ct2/show/NCT03602859">, 20 pages.
clinicaltrials.gov [online], "NCT03651206: Recurrent Ovarian CarcinoSarcoma Anti-pd-1 Niraparib (Rocsan)", U.S. National Library of Medicine, Aug. 29, 2018, retrieved on Jul. 22, 2021, retrieved from URL <"https://clinicaltrials.gov/ct2/show/NCT03651206">, 12 pages.
clinicaltrials.gov [online], "NCT03680508: TSR-022 (Anti-TIM-3 Antibody) and TSR-042 (Anti-PD-1 Antibody) in Patients With Liver Cancer", U.S. National Library of Medicine, Sep. 21, 2018, retrieved on Jul. 22, 2021, retrieved from URL <"https://clinicaltrials.gov/ct2/show/NCT03680508">, 9 pages.
clinicaltrials.gov [online], "NCT03739710: Platform Trial of Novel Regimens Versus Standard of Care (SoC) inNon-small Cell Lung Cancer (NSCLC)", U.S. National Library of Medicine, Nov. 14, 2018, retrieved on Jul. 22, 2021, retrieved from URL <"https://clinicaltrials.gov/ct2/show/NCT03739710">, 14 pages.
clinicaltrials.gov [online], "NCT03981796: A Study to Evaluate Dostarlimab Plus Carboplatin-paclitaxel Versus Placebo Plus Carboplatin-paclitaxel in Participants With Recurrent or Primary Advanced Endometrial Cancer (Ruby)", U.S. National Library of Medicine, Jun. 11, 2019, retrieved on Jul. 22, 2021, retrieved from URL <"https://clinicaltrials.gov/ct2/show/NCT03981796">, 11 pages.
clinicaltrials.gov [online], "NCT04068753: Niraparib in Combination With Dostarlimab in Patients With Recurrent or Progressive Cervix Cancer (Star)", U.S. National Library of Medicine, Aug. 28, 2019, retrieved on Jul. 22, 2021, retrieved from URL <"https://clinicaltrials.gov/ct2/show/NCT04068753">, 9 pages.
clinicaltrials.gov [online], "NCT0413 9902: Neoadjuvant PD-1 Inhibitor Dostarlimab (TSR-042) vs. Combination of Tim-3 Inhibitor Cobolimab (TSR-022) and PD-1 Inhibitor Dostarlimab (TSR-042) in Melanoma", U.S. National Library of Medicine, Oct. 25, 2019, retrieved on Jul. 22, 2021, retrieved from URL <"https://clinicaltrials.gov/ct2/show/NCT0413 9902">, 10 pages.
clinicaltrials.gov [online], "NCT04313504: Study Evaluating the Efficacy of Niraparib and Dostarlimab (TSR-042) in Recurrent/Metastatic HNSCC", U.S. National Library of Medicine, Mar. 18, 2020, retrieved on Jul. 22, 2021, retrieved from URL <"https://clinicaltrials.gov/ct2/show/NCT04313504">, 7 pages.
clinicaltrials.gov [online], "NCT04409002: Niraparib + Dostarlimab + RT in Pancreatic Cancer", U.S. National Library of Medicine, Jun. 1, 2020, retrieved on Jul. 22, 2021, retrieved from URL <"https://clinicaltrials.gov/ct2/show/NCT044090Q2">, 11 pages.
clinicaltrials.gov [online], "NCT04584255: Niraparib + TSR042 in BRCA Mutated Breast Cancer", U.S. National Library of Medicine, Oct. 12, 2020, retrieved on Jul. 22, 2021, retrieved from URL <"https://clinicaltrials.gov/ct2/show/NCT04584255">, 12 pages.
clinicaltrials.gov [online], "NCT04655976: Study of Cobolimab in Combination With Dostarlimab and Docetaxel in Advanced NSCLC Participants (COSTAR Lung)", U.S> National Library of Medicine, Dec. 2020, retrieved on Jul. 22, 2021, retrieved from URL <"https://clinicaltrials.gov/ct2/show/NCT04655976">, 10 pages.
clinicaltrials.gov [online], "NCT04673448: Niraparib and TSR-042 for the Treatment of BRCA-Mutated Unresectable or Metastatic Breast, Pancreas, Ovary, Fallopian Tube, or Primary Peritoneal Cancer", U.S. National Library of Medicine, Dec. 17, 2020, retrieved on Jul. 22, 2021, retrieved from URL <"https://clinicaltrials.gov/ct2/show/NCT04673448">, 12 pages.
clinicaltrials.gov [online], "NCT04895046: Maintenance Niraparib and Dostarlimab in Advanced Cholangiocarcinoma", U.S. National Library of Medicine, May 20, 2021, retrieved on Jul. 22, 2021, retrieved from URL <"https://clinicaltrials.gov/ct2/show/NCT04895046">, 10 pages.
Kasherman et al., ""Dostarlimab in the treatment of recurrent or primary advanced endometrial cancer"", Future Oncology, 2021, 17(8):877-892.
Moreno et al., "Abstract CT053: Preliminary safety, efficacy, and PK/PD characterization from GARNET, a phase 1 clinical trial of the anti-PD-1 monoclonal antibody, TSR-042, inpatients with recurrent or advanced NSCLC and MSI-H endometrial cancer", Cancer Research, Jul. 2018, 2 pages.
Oaknin et al., "Clinical Activity and Safety of the Anti-Programmed Death 1 Monoclonal Antibody Dostarlimab for Patients With Recurrent or Advanced Mismatch Repair-Deficient Endometrial Cancer: A Nonrandomized Phase 1 Clinical Trial", JAMA Oncology, Oct. 2020, 6(11):1766-1772.
Sachdev et al., "Safety, pharmacodynamic, and pharmacokinetic profile of TSR-042, an anti-PD-1 monoclonal antibody, in patients (pts) with advanced solid tumors", Annals of Oncology, Sep. 2017, 28(5):420, 3 pages.
Acierto et al., "Biomarkers for Immunostimulatory Monoclonal Antibodies in Combination Strategies for Melanoma and other Tumor Types," Clinical Cancer Research, 19(5): 1009-1020 (Mar. 1, 2013).
Al Magro et al., "Humanization of antibodies," Frontiers in Bioscience; 13: 1619-1633 (2008).
Altschu l et al., "Gapped BLAST and PSI-BLAST: a new generation of protein database search programs," Nucleic Acids Research, 25(17): 3389-3402 (1997).
Altschul et al., "Basic local alignment search tool," J. Molecular Biol, 1990, 215(3):403-410.
An, Therapeutic Monoclonal Antibodies From Bench to Clinic (An ed.) 3-75 (John Wiley & Sons, Inc., Hoboken, NJ 2009).
Anderson et al., "Lag-3, Tim-3 and TIGIT: Co-inhibitory Receptors with Specialized Functions in Immune Regulation", Immunity, 2016, 989-1004.
Aspeslagh et al., "Rationale for anti-OX40 cancer immunotherapy," European Journal of Cancer, 52: 50-66 (2016).
Ayers et al., "IFN-γ-related mRNA profile predicts clinical response to PD-1 blockade," J. Clin. Invest, 2017, 127(8):2930-2940.
Barber et al., "Restoring function in exhausted CD8 T cells during chronic viral infection," Nature, 439: 682-687 (Feb. 9, 2006).
Bennett et al., "Program death-1 engagement upon TCR activation has distinct effects on costimulation and cytokine-driven proliferation: attenuation of ICOS, IL-4, and IL-21, but not CD28, IL-7, and IL-15 responses," J Immunol., 2003, 170:711-8.
Bertsias et al., "Genetic, Immunologic, and Immunohistochemical Analysis of the Programmed Death 1/Programmed Death Ligand 1 Pathway in Human Systemic Lupus Erythematosus," Arlhritis & Rheumatism, 60(1): 207-218 (Jan. 2009).
Bhatia et al., "Immunobiology of Merkel cell carcinoma: implications for immunotherapy of a polyomavirus-associated cancer," Curr, Oncol. Rep., 13(6): 488-497 (Dec. 2011).
Biegert et al., "Sequence context-specific profiles for homology searching," PNAS, 106(10): 3770-3775 (Mar. 10, 2009).
Bird et al., "Single-Chain Antigen-Binding Proteins," Science, 242: 423-426 (Oct. 21, 1988).
Blank et al., "PD-L 1/B7H-1 Inhibits the Effector Phase of Tumor Rejection by T Cell Receptor (TCR) Transgenic cos+ T Cells," Cancer Research, 64: 1140-1145 (Feb. 1, 2004).
Bohnsack et al., "Adaptation of the immune-related response criteria: iRecist," ESMO, 2014, Abstract 4958.
Bowers et al., "Coupling mammalian cell surface display with somatic hypermutation for the discovery and maturation of human antibodies," PNAS, 108(51 ): 20455-20460 (Dec. 20, 2011).
Brash et al., "Strontium Phosphate Transfection of Human Cells in Primary Culture: Stable Expression of the Simian Virus 40 Large-T-Antigen Gene in Primary Human Bronchial Epithelial Cells," Molecular and Cellular Biology, 7(5): 2031-2034 (May 1987).
Brorson et al., Mutational Analysis of Avidity and Fine Specificity of Anti-Levan Antibodies, The Journal of Immunology, 1999, 163:6694-6701.
Brown et al., "Blockade of Programmed Death-1 Ligands on Dendritic Cells Enhances T Cell Activation and Cytokine Production," The Journal of Immunology, 170: 1257-1266 (2003).
Brown et al., Tolerance of single, but not multiple, amino acid replacements in antibody VH CDR 2: a means of minimizing B cell wastage from somatic hypermutation? The Journal of Immunology, i 56.9 (1996): 3285-3291.

(56) References Cited

OTHER PUBLICATIONS

Brummell et al., "Probing the Combining Site of an Anti-Carbohydrate Antibody by Saturation-Mutagenesis: Role of the Heavy-Chain CDR3 Residues", Biochemistry, 1993, 32:1180-1187.
CA Office Action in Canadian Office Appln. No. 2,910,278, dated Apr. 20, 2020, 3 pages.
Casset et al., "A peptide mimetic of an anti-CD4 monoclonal antibody by rational design", Biochemical and Biophysical Research Communications, 2003, 307:198-205.
Clinicaltrials.gov [online] "ClinicalTrials.gov NCT02657889: Niraparib in Combination With Pembrolizumab in Patients With Triple-negative Breast Cancer or Ovarian Cancer," Aug. 2, 2016, retrieved Jun. 12, 2020, retrieved from URL>https://clinicaltrials.gov/ct2/show/NCT02657889?term=NCT02657889&draw=2&rank=1.
Clinicaltrials.gov [online] ""ClinicalTrials.gov NCT02861573: Study of Pembrolizumab (MK-3475) Combination Therapies in Metastatic Castration-Resistant Prostate Cancer (MK-3475-365/KEYNOTE-365),"" Oct. 14, 2016, retrieved on Apr. 1, 2020, retrieved from URL>https://clinicaltrials.gov/ct2/history/NCT02861573?A=2&B=2&C=merged#StudyPageTop.
Clinicaltrials.gov [online] ""Niraparib in Combination With Pembrolizumab in Patients With Triple-negative Breast Cancer or Ovarian Cancer (TOPACIO),"" Mar. 1, 2017, retrieved Apr. 1, 2020, retrieved from URL>https://clinicaltrials.gov/ct2/show/NCT02657889?term=TESARO&draw=2&rank=5.
Colberre-Garapin et al., "A new dominant hybrid selective marker for higher eukaryotic cells," J Mol. Biol., 1981, 150:1-14.
Colman, "Effects of amino acid sequence changes on antibody-antigen interactions", Research in Immunology, 1994, 145:33-36.
Conese et al., "Gene Therapy Progress and Prospects: Episomally maintained self-replicating systems," Gene Therapy, 11: 1735-1741 (2004).
David et al., "Protein iodination with solid state lactoperoxidase," Biochemistry, 1974, 13:1014-1021.
Davies et al., "Antibody-antigen complexes," Annual Rev Biochem, 1990, 59:439-473.
De Genst et al., "Antibody repertoire development in camelids," Developmental & Comparative Immunology, 30:187-198 (2006).
De St. Groth et al., "Production of Monoclonal Antibodies: Strategy and Tactics," Journal of Immunological Methods, 35: 1-21 (1980).
Dong et al., "Tumor-associated B7-H1 promotes T-cell apoptosis: A potential mechanism of immune evasion," Nature Medicine, 8(8): 793-800 (Aug. 2002).
Durbin et al., Biological Sequence Analysis, Probabilistic Models of Proteins and Nucleic Acids, (Durbin et al., ed.) 1-356 (Cambridge University Press, Cambridge, UK 1998).
Eisenhauer, et al., "New response evaluation criteria in solid tumors: Revised RECIST guideline (version 1. 1.)," Eur. J. of Cancer, 2009, 45:228-247.
EP Search Report in European Appln. No. 20150603.7, dated May 14, 2020, 15 pages.
EP Search Report in European Appln. No. 17867513.8, dated Apr. 8, 2020, 4 pages.
Extended Search Report issued by the European Patent Office for Application No. 14 791454.3 dated Feb. 28, 2017.
Flies et al., "Blockade of the B7-H1/PD-1 Pathway for Cancer Immunotherapy," Yale Journal of Biology and Medicine, 84: 409-421 (2011).
Freeman et al., "Engagement of the PD-1 Immunoinhibitory Receptor by a Novel 87 Family Member Leads to Negative Regulation of Lymphocyte Activation," J. Exp. Med. 192(7): 1027-1034 (Oct. 2, 2000).
Friedlander: "A phase 1b study of the anti-PD-1 monoclonal antibody BGB-A317 (A317) in combination with the PARP inhibitor BGB-290 (290) in advanced solid tumors," Journal of Clinical Oncology, 2017, 35(15 suppl): 5 pages.
Fuhrmann-Benzakein et al., "Inducible and irreversible control of gene expression using a single transgene," Nucleic Acids Research, 28(23): 1-5 (2000).

Goldsby, "Diversity in the Variable-Region Domain is Concentrated in CDRs", Immunology, 2003, 5th edition, pp. 82-84.
Greenwald et al., "The 87 Family Revisited," Annu. Rev. Immunol., 23: 515-548 (2005).
Hamanishi et al., "Programmed cell death 1 ligand 1 and tumor-infiltrating CDS+ T lymphocytes are prognostic factors of human ovarian cancer," PNAS, 104(9): 3360-3365 (Feb. 27, 2007).
Hirano et al., "Blockade of B7-H1 and PD-1 by Monoclonal Antibodies Potentiates Cancer Therapeutic Immunity," Cancer Research, 65(3): 1089-1096 (Feb. 1, 2005).
Holliger et al., "Engineered antibody fragments and the rise of single domains," Nature Biotechnology, 23(9): 1126-1136 (Sep. 2005).
Hotzel et al., "A strategy for risk mitigation of antibodies with fast clearance," mAbs, 4(6): 753-760 (Nov./Dec. 2012).
Hou et al., "Humanization of an Anti-CD34 Monoclonal Antibody by Complementarity-determining Region Grafting Based on Computer-assisted Molecular Modelling," J. Biochem., 144: 115-120 (2008).
Hunter et al., "Preparation of iodine-131 labelled human growth hormone of high specific activity," Nature, 1962, 194:495-496.
Huston et al., "Protein engineering of antibody binding sites: Recovery of specific activity in an anti-digoxin single-chain Fv analogue produced in *Escherichia coli*," PNAS USA, 85: 5879-5883 (Aug. 1988).
Indra et al., "Temporally-controlled site-specific mutagenesis in the basal layer of the epidermis: comparison of the recombinase activity of the tamoxifen-inducible Cre-ERT and Cre-ERT2 recombinases," Nucleic Acids Research, 27(22): 4324-4327 (1999 ).
International Bureau of WIPO, International Preliminary Report on Patentability in International Patent Application No. PCT/US2014/036525 (dated Nov. 12, 2015).
Ishida et al., "Induced expression of PD-1, a novel member of the immunoglobulin gene superfamily, upon programmed cell death," The EMBO Journal, 11(11): 3887-3895 (1992).
Iwai et al., "Involvement of PD-L 1 on tumor cells in the escape from host immune system and tumor immunotherapy by PD-L 1 blockade," PNAS, 99(19): 12293-12297 (Sep. 17, 2002).
Iwai et al., "PD-1 blockade inhibits hematogenous spread of poorly immunogenic tumor cells by enhanced recruitment of effector T cells," International Immunology, 17(2): 133-144 (2004).
Jack et al., "Looping out and deletion mechanism for the immunoglobulin heavy-chain class switch," PNAS USA, 85: 1581-1585 (Mar. 1988).
Johnston, "Biolistic transformation: microbes to mice," Nature, 1990, 346:776-777.
JP Office Action in Japanese Appln. No. 2016-512062, dated Jun. 5, 2018, 9 pages (English translation).
JP Office Action in Japanese Appln. No. 2016-512062, dated May 7, 2019, 3 pages (English translation).
Kasagi et al., "Anti-Programmed Cell Death 1 Antibody Reduces co4+po-1+ T Cells and Relieves the Lupus-Like Nephritis of NZB/W F1 Mice," The Journal of Immunology, 184: 2337-2347 (Feb. 5, 2010).
Kashmiri et al., "SOR grafting-a new approach to antibody humanization," Methods, 36: 25-34 (2005).
Kearney et al., "A New Mouse Myeloma Cell Line That Has Lost Immunoglobulin Expression But Permits the Construction of Antibody-Secreting Hybrid Cell Lines," The Journal of Immunology, 123(4): 1548-1550 (Oct. 1979).
Kent et al., "Ouabain Resistance Conferred by Expression of the cDNA for a Murine Na+,K+-ATPase a Subunit," Science, 237: 901-903 (Aug. 21, 1987).
Kitts et al., "A method for producing recombinant baculovirus expression vectors at high frequency," Biotechniques, 1993, 14:810-817.
Kobayashi et al., "Tryptophan H33 plays an important role in pyrimidine (6-4) pyrimidone photoproduct binding by a high-affinity antibody", Protein Engineering, 1999, 12:879-844.
Kohler and Milstein, "Derivation of specific antibody-producing tissue culture and tumor lines by cell fusion," Eur. J. Immunol., 1976, 5:511-519.
Kramer & Fussenegger, "Transgene control engineering in mammalian cells," Methods Mol. Biol, 2005, 308:123-144.

(56) References Cited

OTHER PUBLICATIONS

Kroner et al., "A PD-1 Polymorphism is Associated with Disease Progression in Multiple Sclerosis," Annals of Neurology, 58(1): 50-57 (Jul. 2005).
Laken et al., "Identification and characterization of TSR-042, a novel anti-human PD-1 therapeutic antibody," European Journal of Cancer, 2016, 69(1):S102.
Latchman et al., "PD-L2 is a second ligand for PD-1 and inhibits T cell activation," Nature Immunology, 2(3): 261-268 (Mar. 2001).
Le et al., "PD-1 Blockade in Tumors with Mismatch-Repair Deficiency," N Engl. J Med, 2015, 372(26):2509-2520.
Li et al., "A Mini-Review for Cancer Immunotherapy: Molecular Understanding of PD-1 /PD-L 1 Pathway & Translational Blockade of Immune Checkpoints," Int. J. Mol. Sci. 2016, 17(7):1151.
Lonberg, "Human antibodies from transgenic animals," Nature Biotechnology, 23(9): 1117-1125 (Sep. 2005).
Lonberg, "Human Monoclonal Antibodies from Transgenic Mice," Therapeutic Antibodies. Handbook of Experimental Pharmacology 181, (Chemajovsky et al., eds.), 69-97 (Springer-Verlag, Berlin 2008).
Lowy et al., "Isolation of Transforming DNA: Cloning the Hamster aprt Gene," Cell, 22: 817-823 (Dec. 1980).
Lucklow et al., "Efficient generation of infectious recombinant baculoviruses by site-specific transposon-mediated insertion of foreign genes into a baculovirus genome propagated in *Escherichia coli*," J. Virol., 1993, 67:4566-4579.
Lucklow, "Baculovirus systems for the expression of human gene products," Curr. Opin. Biotechnol.,1993, 4:564-572.
Luckow et al., "Efficient Generation of Infectious Recombinant Baculoviruses by Site-Specific Transposon-Mediated Insertion of Foreign Genes into a Baculovirus Genome Propagated in *Escherichia coli*," Journal of Virology, 67(8): 4566-4579 (Aug. 1993).
Mahoney et al., "The Next Immune-Checkpoint Inhibitors: PD-1/ PD-L 1 Blockade in Melanoma," Clinical Therapeutics, 37(4):764-782 (2015).
Malmqvist, "Biospecific interaction analysis using biosensor technology," Nature, 1993, 361:186-87.
McConnell et al., "An integrated approach to extreme thermostabilization and affinity maturation of an antibody," Protein Engineering, Design & Selection, 26(2): 151-163 (2013).
Mellati et al., "Anti-PD-1 and Anti-PDL-1 Monoclonal Antibodies Causing Type 1 Diabetes", Diabetes Care, Sep. 2015, 38:e137-e138.
Mulligan et al., "Selection for animal cells that express the *Escherichia coli* gene coding for xanthine-guanine phosphoribosyltransferase," PNAS USA, 78(4): 2072-2076 (Apr. 1981).
Myers and Miller, "Optimal alignments in linear space," Cabios, 1989, 4:11-17.
Ngiow et al., "Anti-TIM3 Antibody Promotes T Cell IFN-v-Mediated Antitumor Immunity and Suppresses Established Tumors," Cancer Res., 71(10): 3540-3551 (May 15, 2011).
Ni et al., "PD-1 gene haplotype is associated with the development of type 1 diabetes mellitus in Japanese children," Hum. Genet., 121: 223-232 (2007).
Nielsen et al., "Association of a putative regulatory polymorphism in the PD-1 gene with susceptibility to type 1 diabetes," Tissue Antigens, 62: 492-497 (2003).
Nishimura et al., "Development of Lupus-like Autoimmune Diseases by Disruption of the PD-1 Gene Encoding an ITIM Motif-Canying Immuno receptor," Immunity, 11: 141-151 (Aug. 1999).
Nishina et al., "Developing a common language for tumor response to immunotherapy: immune-related response criteria using unidimensional measurements," Clin. Cancer Res., 2013, 19(14):3936-43.
No et al., "Ecdysone-inducible gene expression in mammalian cells and transgenic mice," PNAS USA, 93: 3346-3351 (Apr. 1996).
Nygren, "Conjugation of Horseradish Peroxidase to Fab Fragments with Different Homobifunctional and Heterobifunctional Cross-Linking Reagents," The Journal of Histochemistry and Cytochemistry, 30(5): 407-412 (1982).
O'Hare et al., "Transformation of mouse fibroblasts to methotrexate resistance by a recombinant plasmid expressing a prokaryotic dihydrofolate reductase," PNAS USA, 78(3): 1527-1531 (Mar. 1981).
Okazaki et al., "PD-1 and PD-1 ligands: from discovery to clinical application," Int. Immunol., 2007, 19(7):813-824.
Osbourn et al., "Directed selection of MIP-1 a neutralizing CCR5 antibodies from a phage display human antibody library," Nature Biotechnology, 16: 778-781 (Aug. 1998).
Pain et al., "Preparation of protein A-peroxidase monoconjugate using a heterobifunctional reagent, and its use in enzyme immunoassays," J. Immunol, Meth., 1981, 40: 219-230.
Parry et al., "CTLA-4 and PD-1 Receptors Inhibit T-Cell Activation by Distinct Mechanisms," Molecular and Cellular Biology, 25(21 ): 9543-9553 (Nov. 2005).
Patnaik et al., "Phase I study of MK-3475 (anti-PD-1 monoclonal antibody) in patients with advanced solid tumors," J. Clin. Oncol., 30(Abstract No. 2512): 30 (2012 ).
Porichis et al., "Role of PD-1 in HIV Pathogenesis and as Target for Therapy," Curr. HIV/AIDS Rep., 9(1): 81-90 (Mar. 2012).
Qin et al., "The Diverse Function of PD-1/PD-L Pathway Beyond Cancer", Frontiers in Immunology, 2019, vol. 10, pp. 1-16.
Rudikoff et al., "Single amino acid substitution altering antigen-binding specificity", Proc. Natl. Acad. Sci. USA, 1982, 79(6):1979-1983.
Sakuishi et al., "Targeting Tim-3 and PD-1 pathways to reverse T cell exhaustion and restore anti-tumor immunity," The Journal of Experimental Medicine, 207(10): 2187-2194 (Sep. 27, 2010).
Sanmam Ed et al., "Agonists of Co-stimulation in Cancer Immunotherapy Directed Against CD137, OX40, GITR, CD27, CD28, and ICOS," Seminars in Oncology 42(4): 640-655 (Aug. 2015).
Santerre et al., "Expression of prokaryotic genes for hygromycin B and G418 resistance as dominant-selection markers in mouse L cells," Gene, 1984, 30:147-156.
Search Report issued by the European Patent Office dated Oct. 28, 2016.
Sharpe et al., "The function of programmed cell death 1 and its ligands in regulating autoimmunity and infection," Nature Immunology, 8(3): 239-245 (Mar. 2007).
Silva et al., "The S228P mutation prevents in vivo and in vitro IgG4 Fab-arm exchange as demonstrated using a combination of novel quantitative immunoassays and physiological matrix preparation," J. Biol. Chem., 2015, 290(9):5462-5469.
Soding, "Protein homology detection by HMM-HMM comparison," Bioinformatics, 21(7): 951-960 (2005).
Szybalska et al., "Genetics of Human Cell Lines, IV. DNA-Mediated Heritable Transformation of a Biochemical Trait," PNAS., 48: 2026-2034 (1962).
Tahoori et al., "Association of programmed cell death-1 (PDCD-1) gene polymorphisms with rheumatoid arthritis in Iranian patients," Clinical and Experimental Rheumatology, 29: 763-767 (Sep. 2011).
Tang et al., "Programmed Death 1 Pathway inhibition in Metastatic Renal Cell Cancer and Prostate Cancer," Curr. Oncol., Rep., 15: 98-104 (2013).
Topalian et al., "Safety, Activity, and Immune Correlates of Anti-PD-1 Antibody in Cancer," The New England Journal of Medicine, 366(26): 2443-2454 (Jun. 28, 2012).
Turnis et al., "Combinatorial immunotherapy: PD-1 may not be LAG-ing behind anymore." Oncoimmunology, 1.7 (2012): 1172-1174.
United States Patent and Trademark Office, International Search Report in International Patent Application No. PCT/US2014/ 036525 (dated Dec. 24, 2014).
Urlaub et al., "Isolation of Chinese hamster cell mutants deficient in dihydrofolate reductase activity," PNAS USA, 77(7): 4216-4220 (Jul. 1980).
Vitetta et al., "Considering Therapeutic Antibodies," Science, 313: 308-309 (Jul. 21, 2006).
Weber, "Immune Checkpoint Proteins: A New Therapeutic Paradigm for Cancer-Preclinical Background: CTLA-4 and PD-1 Blockade," Seminars in Oncology, 37(5): 430-439 (Oct. 2010).

(56) References Cited

OTHER PUBLICATIONS

Westdorp et al., "Opportunities for immunotherapy in microsatellite instable colorectal cancer," Cancer Immunol. Immunother., 2016, 65(10):1249-1259.
Wigler et al., "Transfer of Purified Herpes Virus Thymidine Kinase Gene to Cultured Mouse Cells," Cell, 11: 223-232 (May 1977).
Wigler et al., "Transformation of mammalian cells with an amplifiable dominant-acting gene," PNAS USA, 77(6): 3567-3570 (Jun. 1980).
Woo et al., "Immune inhibitory molecules LAG-3 and PD-1 synergistically regulate T cell function to promote tumoral immune escape," Cancer Res., 72(4): 917-927 (Feb. 15, 2012).
Yamazaki et al., "Expression of Programmed Death 1 Ligands by Murine T Cells and APC," The Journal of Immunology, 169: 5538-5545 (2002).
CAS Entry 2022215-59-2, STN, Oct. 31, 2016, 2 pages.
Caroline Robert et al: "Anti-Programmed-Death-Receptor-1 Treatment With Pembrolizumab in Ipilimumab-Refractory Advanced Melanoma: A Randomized Dose-Comparison Cohort of a Phase 1 Trial", The Lancet, vol. 384, No. 9948, Sep. 1, 2014 (Sep. 1, 2014), pp. 1109-1117, XP055318318, GB ISSN: 0140-6736, DOI: 10.1016/S0140-6737 (14) 60958-2, p. 1115, col. 1, paragraph 1; tables 1-3.
Rituparna Das et al: "Combination Therapy With Anti-CTLA-4 and Anti-PD-1 Leads to Distinct Immunologic Changes in Vivo", The Journal of Immunology, vol. 194, No. 3, Dec. 24, 2014 (Dec. 24, 2014), pp. 950-959, XP055462350, US ISSN: 0022-1767, DOI: 10.4049/jimmunol.1401686, p. 956, col. 2, paragraph 2; figure 5.
Shruti Agrawal et al: "Nivolumab Dose Selection: Challenges, Opportunities, and Lessons Learned for Cancer Immunotherapy", Journal for Immunotherapy of Cancer, BioMed Central LTD, London, UK, vol. 4, No. 1, Nov. 15, 2016 (Nov. 15, 2016), pp. 1-11, XP021241445, DOI: 10.1186/S40425-016-0177-2, p. 8/11, col. 2, paragraph 3, tables 1, 2, p. 10/11, col. 1, paragraph 2, 3, p. 5/11, col. c1, last paragraph-col. c2, paragraph 1; figure 3.
International Search Report for PCT/US2018/013029, 8 pages (dated Jun. 6, 2018).
Ghosh et al., "TSR-033, a Novel Therapeutic Antibody Targeting LAG-3, Enhances T-Cell Function and the Activity of PD-1 Blockade In Vitro and In Vivo," Molecular Cancer Therapeutics, Mar. 2019, 18: 632-641.

\* cited by examiner

SEQUENCE LISTING

```
<160> NUMBER OF SEQ ID NOS: 14

<210> SEQ ID NO 1
<211> LENGTH: 117
<212> TYPE: PRT
<213> ORGANISM: Artificial Sequence
<220> FEATURE:
<223> OTHER INFORMATION: Synthetic Polypeptide
```

-continued

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala
            115

<210> SEQ ID NO 2
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg
            100                 105

<210> SEQ ID NO 3
<211> LENGTH: 443
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Pro Tyr Tyr Ala Met Asp Tyr Trp Gly Gln Gly Thr Thr Val
        100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
        340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 4
<211> LENGTH: 214
<212> TYPE: PRT
<213> ORGANISM: Artificial Sequence
<220> FEATURE:

<223> OTHER INFORMATION: Synthetic Polypeptide

<400> SEQUENCE: 4

```
Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 1329
<212> TYPE: DNA
<213> ORGANISM: Artificial Sequence
<220> FEATURE:
<223> OTHER INFORMATION: Synthetic Polynucleotide

<400> SEQUENCE: 5

```
gaggtgcagc tgttggagtc tgggggaggc ttggtacagc ctggggggtc cctgagactc    60
tcctgtgcag cctctggatt cactttcagt agctatgaca tgtcttgggt ccgccaggct   120
ccagggaagg ggctggagtg ggtctcaacc attagtggtg gtggtagtta cacctactat   180
caagacagtg tgaaggggcg gttcaccatc tccagagaca attccaagaa cacgctgtat   240
ctgcaaatga acagcctgag agccgaggac acggccgtat attactgtgc gtccccttac   300
tatgctatgg actactgggg gcaagggacc acggtcaccg tctcctcagc atccaccaag   360
ggcccatcgg tcttccccgct agcaccctgc tccaggagca cctccgagag cacagccgcc   420
ctgggctgcc tggtcaagga ctacttcccc gaaccagtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cgaagaccta cacctgcaac   600
gtagatcaca agcccagcaa caccaaggtg gacaagagag ttgagtccaa atatggtccc   660
ccatgcccac catgcccagc acctgagttc ctggggggac catcagtctt cctgttcccc   720
```

```
ccaaaaccca aggacactct catgatctcc cggacccctg aggtcacgtg cgtggtggtg        780
gacgtgagcc aggaagaccc cgaggtccag ttcaactggt acgtggatgg cgtggaggtg        840
cataatgcca agacaaagcc gcgggaggag cagttcaaca gcacgtaccg tgtggtcagc        900
gtcctcaccg tcctgcacca ggactggctg aacggcaagg agtacaagtg caaggtctcc        960
aacaaaggcc tcccgtcctc catcgagaaa accatctcca aagccaaagg gcagccccga       1020
gagccacagg tgtacaccct gcccccatcc caggaggaga tgaccaagaa ccaggtcagc       1080
ctgacctgcc tggtcaaagg cttctacccc agcgacatcg ccgtggagtg ggagagcaat       1140
gggcagccgg agaacaacta caagaccacg cctcccgtgc tggactccga cggctccttc       1200
ttcctctaca gcaggctaac cgtggacaag agcaggtggc aggaggggaa tgtcttctca       1260
tgctccgtga tgcatgaggc tctgcacaac cactacacac agaagagcct ctccctgtct       1320
ctgggtaaa                                                               1329
```

<210> SEQ ID NO 6
<211> LENGTH: 642
<212> TYPE: DNA
<213> ORGANISM: Artificial Sequence
<220> FEATURE:
<223> OTHER INFORMATION: Synthetic Polynucleotide

<400> SEQUENCE: 6

```
gacatccagt tgacccagtc tccatccttc ctgtctgcat atgtaggaga cagagtcacc         60
atcacttgca aggccagtca ggatgtgggt actgctgtag cctggtatca gcaaaaacca        120
gggaaagccc ctaagctcct gatctattgg gcatccaccc tgcacactgg ggtcccatca        180
aggttcagcg gcagtggatc tgggacagaa ttcactctca caatcagcag cctgcagcct        240
gaagattttg caacttatta ctgtcagcat tatagcagct atccgtggac gtttggccag        300
gggaccaagc tggagatcaa acggactgtg gctgcaccat ctgtcttcat cttcccgcca        360
tctgatgagc aattgaaatc tggaactgcc tctgttgtgt gcctgctgaa taacttctat        420
cccagagagg ccaaagtaca gtggaaggtg gataacgccc tccaatcggg taactcccag        480
gagagtgtca cagagcagga cagcaaggac agcacctaca gcctcagcag caccctgacg        540
ctgagcaaag cagactacga gaaacacaaa gtctacgcct gcgaagtcac ccatcagggc        600
ctcagctcgc ccgtcacaaa gagcttcaac aggggagagt gt                          642
```

<210> SEQ ID NO 7
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Ser Pro Tyr Tyr Ala Met Asp Tyr Trp Gly Gln Gly Thr Thr Val
            100                 105                 110

Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 9

Ser Tyr Asp Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 10

Thr Ile Ser Gly Gly Gly Ser Tyr Thr Tyr Tyr Gln Asp Ser Val Lys
1               5                   10                  15

Gly

<210> SEQ ID NO 11
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 11
```

```
Pro Tyr Tyr Ala Met Asp Tyr
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 12

Lys Ala Ser Gln Asp Val Gly Thr Ala Val Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 13

Trp Ala Ser Thr Leu His Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 14

Gln His Tyr Ser Ser Tyr Pro Trp Thr
1               5
```

METHODS OF TREATING CANCER WITH ANTI-PD-1 ANTIBODIES

CROSS-REFERENCE TO RELATED APPLICATIONS

The present application is a 35 U.S.C. § 371 National Stage Application of International Application No. PCT/US2018/013029, filed Jan. 9, 2018, and claims benefit of U.S. Provisional Application No. 62/444,336, filed Jan. 9, 2017, U.S. Provisional Application No. 62/477,423, filed Mar. 27, 2017, U.S. Provisional Application No. 62/491,220, filed Apr. 27, 2017, and U.S. Provisional Application No. 62/556,386, filed Sep. 9, 2017, each of which is incorporated by reference in its entirety.

SEQUENCE LISTING

The present specification makes reference to a Sequence Listing provided in electronic form as an ASCII.txt file named "TSR-006 SEQ LIST_ST25" that was generated on Jan. 8, 2018, and is 14,555 bytes in size.

BACKGROUND

Cancer is a serious public health problem, with about 600,920 people in the United States of America expected to die of cancer in 2017 alone according to the American Cancer Society, Cancer Facts & Figures 2017 (https://www.cancer.org/research/cancer-facts-statistics/all-cancer-facts-figures/cancer-facts-figures-2017.html). Accordingly, there continues to be a need for effective therapies to treat cancer patients.

SUMMARY

The present invention encompasses a recognition that certain dosage regimens for agents that are capable of inhibiting anti-programmed death-1 protein (PD-1) (e.g., PD-1 binding agents) are useful for treating disorders such as cancer.

In embodiments, a PD-1 inhibitor is a PD-1 binding agent. In embodiments, a PD-1 binding agent is an antibody, an antibody conjugate, or an antigen-binding fragment thereof. In embodiments, a PD-1 binding agent is an antibody agent (i.e., an anti-PD-1 antibody agent).

In embodiments, a PD-1 binding agent is an anti-PD-1 antibody. In embodiments, a PD-1 binding agent comprises a heavy chain variable region with one or more CDR sequences having at least about 80%, 85%, 90%, 91%, 92%, 93%, 94%, 95%, 96%, 97%, 98%, or 99% sequence identity to SEQ ID NOs: 9, 10, or 11. In embodiments, a PD-1 binding agent comprises a heavy chain variable region with two or three CDR sequences having at least about 80%, 85%, 90%, 91%, 92%, 93%, 94%, 95%, 96%, 97%, 98%, or 99% sequence identity to SEQ ID NOs: 9, 10, or 11.

In embodiments, a PD-1 binding agent comprises a light chain variable region with one or more CDR sequences having at least about 80%, 85%, 90%, 91%, 92%, 93%, 94%, 95%, 96%, 97%, 98%, or 99% sequence identity to SEQ ID NOs: 12, 13, and 14. In embodiments, a PD-1 binding agent comprises a light chain variable region with two or three CDR sequences having at least about 80%, 85%, 90%, 91%, 92%, 93%, 94%, 95%, 96%, 97%, 98%, or 99% sequence identity to SEQ ID NOs: 12, 13, and 14.

In some embodiments, a PD-1-binding agent comprises a heavy chain variable region with one or more CDR sequences selected from SEQ ID NOs: 9, 10, and 11 and/or a light chain variable region with one or more CDR sequences selected from SEQ ID NOs: 12, 13, and 14. In some embodiments, a PD-1-binding agent comprises a heavy chain variable region with two or more CDR sequences selected from SEQ ID NOs: 9, 10, and 11 and/or a light chain variable region with two or more CDR sequences selected from SEQ ID NOs: 12, 13, and 14. In some embodiments, a PD-1-binding agent comprises a heavy chain variable region with three CDRs that have sequences of SEQ ID NOs: 9, 10, and 11 and/or a light chain variable region with three CDRs that have sequences of SEQ ID NOs: 12, 13, and 14. In some embodiments, a PD-1-binding agent comprises a heavy chain variable region with three CDRs that have sequences of SEQ ID NOs: 9, 10, and 11 and a light chain variable region with three CDRs that have sequences of SEQ ID NOs: 12, 13, and 14.

In some embodiments, a PD-1-binding agent comprises an immunoglobulin heavy chain variable domain comprising an amino acid sequence having at least about 80%, 85%, 90%, 91%, 92%, 93%, 94%, 95%, 96%, 97%, 98%, or 99% sequence identity to SEQ ID NO: 1 or SEQ ID NO:7. In some embodiments, a PD-1-binding agent comprises an immunoglobulin heavy chain variable domain comprising an amino acid sequence having at least about 80%, 85%, 90%, 91%, 92%, 93%, 94%, 95%, 96%, 97%, 98%, or 99% sequence identity to SEQ ID NO: 1. In some embodiments, a PD-1-binding agent comprises an immunoglobulin heavy chain variable domain comprising an amino acid sequence having at least about 80%, 85%, 90%, 91%, 92%, 93%, 94%, 95%, 96%, 97%, 98%, or 99% sequence identity to SEQ ID NO: 7.

In some embodiments, a PD-1-binding agent comprises an immunoglobulin light chain variable domain comprising an amino acid sequence having at least about 80%, 85%, 90%, 91%, 92%, 93%, 94%, 95%, 96%, 97%, 98%, or 99% sequence identity to SEQ ID NO: 2 or SEQ ID NO: 8. In some embodiments, a PD-1-binding agent comprises an immunoglobulin light chain variable domain comprising an amino acid sequence having at least about 80%, 85%, 90%, 91%, 92%, 93%, 94%, 95%, 96%, 97%, 98%, or 99% sequence identity to SEQ ID NO: 2. In some embodiments, a PD-1-binding agent comprises an immunoglobulin light chain variable domain comprising an amino acid sequence having at least about 80%, 85%, 90%, 91%, 92%, 93%, 94%, 95%, 96%, 97%, 98%, or 99% sequence identity to SEQ ID NO: 8.

In some embodiments, a PD-1-binding agent comprises an immunoglobulin heavy chain variable domain whose amino acid sequence comprises SEQ ID NO: 1 or SEQ ID NO:7 and an immunoglobulin light chain variable domain whose amino acid sequence comprises SEQ ID NO: 2 or SEQ ID NO: 8.

In some embodiments, a PD-1-binding agent comprises an immunoglobulin heavy chain comprising an amino acid sequence having at least about 80%, 85%, 90%, 91%, 92%, 93%, 94%, 95%, 96%, 97%, 98%, or 99% sequence identity to SEQ ID NO: 3.

In some embodiments, a PD-1-binding agent comprises an immunoglobulin light chain comprising an amino acid sequence having at least about 80%, 85%, 90%, 91%, 92%, 93%, 94%, 95%, 96%, 97%, 98%, or 99% sequence identity to SEQ ID NO: 4.

In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The PD-1 binding agents can be any PD-1 binding agent known in the art. In some embodiments, a PD-1-binding agent is nivolumab, pembrolizumab, atezolizumab, durvalumab, avelumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZMO09, KN-035, AB122, genolimzumab (CBT-501), FAZ-053, CK-301, AK 104, or GLS-010, or any of the PD-1 antibodies disclosed in WO2014/179664.

In some embodiments, a PD-1-binding agent (e.g., anti-PD-1 antibody agent) binds an epitope of PD-1 which blocks the binding of PD-1 to any one or more of its putative ligands. In some embodiments, a PD-1-binding agent (e.g., anti-PD-1 antibody agent) binds an epitope of PD-1 which blocks the binding of PD-1 to two or more of its putative ligands. In a some embodiments, a PD-1-binding agent (e.g., anti-PD-1 antibody agent) binds an epitope of a PD-1 protein which blocks the binding of PD-1 to PD-L1 and/or PD-L2. PD-1-binding agents (e.g., anti-PD-1 antibody agents) of the present disclosure may comprise a heavy chain constant region (Fe) of any suitable class. In some embodiments, a PD-1-binding agent (e.g., anti-PD-1 antibody agent) comprises a heavy chain constant region that is based upon wild-type IgG1, IgG2, or IgG4 antibodies, or variants thereof.

The present disclosure provides methods of treating a disorder in a subject comprising administering a therapeutically effective dose of an agent that is capable of inhibiting Programmed Death-1 Protein (PD-1) signaling. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg. In embodiments, a PD-1 inhibitor is any PD-1 binding agent described herein (e.g., any anti-PD-1 antibody described herein).

The present disclosure provides methods of increasing T cell activation or T cell effector function in a subject, which method comprises administering a therapeutically effective dose of an agent that is capable of inhibiting Programmed Death-1 Protein (PD-1) signaling. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg. In embodiments, a PD-1 inhibitor is any PD-1 binding agent described herein (e.g., any anti-PD-1 antibody described herein).

The present disclosure provides methods of reducing tumors or inhibiting the growth of tumor cells in a subject, which method comprises administering a therapeutically effective dose of an agent that is capable of inhibiting Programmed Death-1 Protein (PD-1) signaling. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg. In embodiments, a PD-1 inhibitor is any PD-1 binding agent described herein (e.g., any anti-PD-1 antibody described herein).

The present disclosure provides methods of inducing an immune response in a subject, which method comprises administering a therapeutically effective dose of an agent that is capable of inhibiting Programmed Death-1 Protein (PD-1) signaling. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg. In embodiments, a PD-1 inhibitor is any PD-1 binding agent described herein (e.g., any anti-PD-1 antibody described herein).

The present disclosure provides methods of enhancing an immune response or increasing the activity of an immune cell in a subject, which method comprises administering a therapeutically effective dose of an agent that is capable of inhibiting Programmed Death-1 Protein (PD-1) signaling. In embodiments, an immune response is a humoral or cell mediated immune response. In embodiments, an immune response is a CD4 or CD8 T cell response. In embodiments, an immune response is a B cell response. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg. In embodiments, a PD-1 inhibitor is any PD-1 binding agent described herein (e.g., any anti-PD-1 antibody described herein).

The present disclosure provides methods of treating cancer that include administering compositions that deliver particular PD-1-binding agents. In embodiments, a PD-1 binding agent in administered in an amount that is about 1, 3 or 10 mg/kg. In embodiments, a PD-1 binding agent in administered in an amount that is about 100-2000 mg (e.g., about 100 mg; about 200 mg; about 300 mg; about 400 mg; about 500 mg; about 600 mg; about 700 mg about 800 mg; about 900 mg about 1000 mg; about 1100 mg; about 1200 mg; about 1300 mg; about 1400 mg; about 1500 mg; about 1600 mg; about 1700 mg; about 1800 mg; about 1900 mg; or about 2000 mg). In embodiments, a PD-1 binding agent in administered in an amount that is about 1 mg/kg. In embodiments, a PD-1 binding agent in administered in an amount that is about 3 mg/kg. In embodiments, a PD-1 binding agent in administered in an amount that is about 10 mg/kg. In embodiments, a PD-1 binding agent in administered in an amount that is about 500 mg. In embodiments, a therapeutically effective dose is about 800 mg. In embodiments, a PD-1 binding agent in administered in an amount that is about 1000 mg. In embodiments, a PD-1 inhibitor is any PD-1 binding agent described herein (e.g., any anti-PD-1 antibody described herein).

The present disclosure provides methods of treating cancer comprising administering to a patient in need of treatment an anti-programmed death-1 protein (PD-1) antibody at a therapeutically effective dose at an administration interval for a period sufficient to achieve clinical benefit. In embodiments, an anti-PD-1 antibody comprises a heavy chain variable region comprising CDR sequences of SEQ ID NOs: 9, 10, and 11 and a light chain variable region comprising CDR sequences of SEQ ID NOs: 12, 13, and 14. In embodiments, an anti-PD-1 antibody comprises an immunoglobulin heavy chain variable domain whose amino acid sequence comprises SEQ ID NO:1 or SEQ ID NO:7 and/or an immunoglobulin light chain variable domain whose amino acid sequence comprises SEQ ID NO:2 or SEQ ID NO:8. In embodiments, an anti-PD-1 antibody comprises an immunoglobulin heavy chain polypeptide whose amino acid sequence comprises SEQ ID NO:3 and/or an immunoglobulin light chain polypeptide whose amino acid sequence comprises SEQ ID NO:4. In embodiments, a therapeutically effective dose is: about 1, 3 or 10 mg/kg. In embodiments, a therapeutically effective dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 500 mg. In embodiments, a therapeutically effective dose is about 800 mg. In embodiments, a therapeutically effective dose is about 1000 mg.

The present disclosure provides methods of treating cancer comprising administering to a patient in need of treatment an anti-programmed death-1 protein (PD-1) antibody at a first dose at a first interval for a first period; and administering to the patient the anti-PD-1 antibody at a second dose at a second interval for a second period. In embodiments, an anti-PD-1 antibody comprises a heavy chain variable region comprising CDR sequences of SEQ ID NOs: 9, 10, and 11 and a light chain variable region comprising CDR sequences of SEQ ID NOs: 12, 13, and 14. In embodiments, an anti-PD-1 antibody comprises an immunoglobulin heavy chain variable domain whose amino acid sequence comprises SEQ ID NO:1 or SEQ ID NO:7 and/or an immunoglobulin light chain variable domain whose amino acid sequence comprises SEQ ID NO:2 or SEQ ID NO:8. In embodiments, an anti-PD-1 antibody comprises an immunoglobulin heavy chain polypeptide whose amino acid sequence comprises SEQ ID NO:3 and/or an immunoglobulin light chain polypeptide whose amino acid sequence comprises SEQ ID NO:4. In embodiments, a dose is: about 1, 3 or 10 mg/kg. In embodiments, a dose is a flat dose of about 100-2000 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; a flat dose about 1600 mg; a flat dose about 1700 mg; a flat dose about 1800 mg; a flat dose about 1900 mg; or a flat dose about 2000 mg). In embodiments, a therapeutically effective dose is about 1 mg/kg. In embodiments, a dose is about 3 mg/kg. In embodiments, a dose is about 10 mg/kg. In embodiments, a therapeutically effective dose is a flat dose about 500 mg. In embodiments, a therapeutically effective dose is a flat dose about 800 mg. In embodiments, a therapeutically effective dose is about 1000 mg. In embodiments, the first dose and second dose are different. In embodiments, the first dose is about 500 mg and the second dose is about 1000 mg. In embodiments, the first interval and the second interval are different. In embodiments, the first interval is once every three weeks and the second interval is once every six weeks. In embodiments, anti-PD-1 antibody is administered at the first dose of 500 mg once every three weeks for the first period of 2-6 dosing cycles (e.g., the first 3, 4, or 5 dosing cycles), and at the second dose of 1000 mg once every six weeks until therapy is discontinued (e.g., due to disease progression, an adverse event, or as determined by a physician). In embodiments, anti-PD-1 antibody is administered at the first dose of 500 mg once every three weeks for the first three dosing cycles, and at the second dose of 1000 mg once every six weeks or more until therapy is discontinued (e.g., due to disease progression, an adverse event, or as determined by a physician). In embodiments, anti-PD-1 antibody is administered at the first dose of 500 mg once every three weeks for the first four dosing cycles, and at the second dose of 1000 mg once every six weeks or more until therapy is discontinued (e.g., due to disease progression, an adverse event, or as determined by a physician). In embodiments, anti-PD-1 antibody is administered at the first dose of 500 mg once every three weeks for the first five dosing cycles, and at the second dose of 1000 mg once every six weeks or more until therapy is discontinued (e.g., due to disease progression, an adverse event, or as determined by a physician). In embodiments, the second dose is administered once every six weeks.

In any of the methods described herein, a therapeutically effective dose is about 1 mg/kg of a PD-1 binding agent. In any of the methods described herein, a therapeutically effective dose is about 3 mg/kg of a PD-1 binding agent. In any of the methods described herein, a therapeutically effective dose is about 10 mg/kg of a PD-1 binding agent. In embodiments, a PD-1 binding agent is any anti-PD-1 antibody described herein.

In any of the methods described herein, a therapeutically effective dose is about 100 mg of a PD-1 binding agent. In any of the methods described herein, a therapeutically effective dose is about 200 mg of a PD-1 binding agent. In any of the methods described herein, a therapeutically effective dose is about 300 mg of a PD-1 binding agent. In any of the methods described herein, a therapeutically effective dose is about 400 mg of a PD-1 binding agent. In any of the methods described herein, a therapeutically effective dose is about 500 mg of a PD-1 binding agent. In any of the methods described herein, a therapeutically effective dose is about 600 mg of a PD-1 binding agent. In any of the methods described herein, a therapeutically effective dose is about 700 mg of a PD-1 binding agent. In any of the methods described herein, a therapeutically effective dose is about 800 mg of a PD-1 binding agent. In any of the methods described herein, a therapeutically effective dose is about 900 mg of a PD-1 binding agent. In any of the methods described herein, a therapeutically effective dose is about 1000 mg of a PD-1 binding agent. In any of the methods described herein, a therapeutically effective dose is about 1100 mg of a PD-1 binding agent. In any of the methods described herein, a therapeutically effective dose is about 1200 mg of a PD-1 binding agent. In any of the methods described herein, a therapeutically effective dose is about 1300 mg of a PD-1 binding agent. In any of the methods described herein, a therapeutically effective dose is about 1400 mg of a PD-1 binding agent. In any of the methods described herein, a therapeutically effective dose is about 1500 mg of a PD-1 binding agent. In any of the methods described herein, a therapeutically effective dose is about 1600 mg of a PD-1 binding agent. In any of the methods described herein, a therapeutically effective dose is about 1700 mg of a PD-1 binding agent. In any of the methods described herein, a therapeutically effective dose is about 1800 mg of a PD-1 binding agent. In any of the methods described herein, a therapeutically effective dose is about 1900 mg of a PD-1 binding agent. In any of the methods described herein, a therapeutically effective dose is about 2000 mg of a PD-1 binding agent. In embodiments, a PD-1 binding agent is any anti-PD-1 antibody described herein.

In embodiments, a PD-1 binding agent is administered at an administration interval (or treatment cycle) of once a week (Q1W), once every 2 weeks (Q2W), once every 3 weeks (Q3W), once every 4 weeks (Q4W), once every 5 weeks (Q5W), or once every 6 weeks (Q6W). In embodiments, a PD-1 binding agent is administered at an administration interval (or treatment cycle) of once a week (Q1W). In embodiments, a PD-1 binding agent is administered at an administration interval (or treatment cycle) of once every 2 weeks (Q2W). In embodiments, a PD-1 binding agent is administered at an administration interval (or treatment cycle) of once every three weeks (Q3W). In embodiments, a PD-1 binding agent is administered at an administration interval (or treatment cycle) of once every 4 weeks (Q4W). In embodiments, a PD-1 binding agent is administered at an administration interval (or treatment cycle) of once every 5 weeks (Q5W). In embodiments, a PD-1 binding agent is administered at an administration interval (or treatment cycle) of once every 6 weeks (Q6W). In embodiments, a PD-1 binding agent is administered for a period of at least about 2, 3, 4, 5, 6, 7, 8, 9, 10, 11, 12, 13, 14, 15, 16, 17, 18, 19, 20 weeks, or more. In embodiments, a PD-1 binding agent is administered on the first day of a treatment cycle or within 1, 2, or 3 days of the first day of a treatment cycle. In embodiments, a PD-1 binding agent is any anti-PD-1 antibody described herein.

In embodiments, a PD-1 binding agent described herein is administered according to dosing regimens demonstrated to achieve a clinical benefit in some patients (for example, according to a regimen as determined by a physician, including dosing modifications). In embodiments, a PD-1 binding agent described herein is administered until treatment is discontinued due to, e.g., disease progression or an adverse reaction or as determined by a physician. In embodiments, a clinical benefit is stable disease ("SD"), a partial response ("PR") and/or a complete response ("CR"). In embodiments, a clinical benefit is stable disease ("SD"). In embodiments, a clinical benefit is a partial response ("PR"). In embodiments, a clinical benefit is a complete response ("CR"). In embodiments, PR or CR is determined in accordance with Response Evaluation Criteria in Solid Tumors (RECIST). In embodiments, a PD-1 binding agent is administered for a longer period to maintain clinical benefit. In embodiments, a PD-1 binding agent is any anti-PD-1 antibody described herein.

In embodiments, a PD-1 binding agent is administered periodically to a subject at a dose of about 500 mg or about 1000 mg. In embodiments, a PD-1 binding agent is administered periodically to a subject at a dose of about 500 mg (e.g., once every three weeks (Q3W) and/or for 2, 3, 4, 5, 6, or more cycles). In embodiments, a PD-1 binding agent is administered periodically to a subject at a dose of about 1000 mg (e.g., once every three weeks (Q3W) and/or for 2, 3, 4, 5, 6, or more cycles). In embodiments, a PD-1 binding agent is administered to a subject at a dose of about 500 mg according once every three weeks (Q3W) for 3 cycles. In embodiments, a PD-1 binding agent is administered to a subject at a dose of about 500 mg according once every three weeks (Q3W) for 4 cycles. In embodiments, a PD-1 binding agent is administered to a subject at a dose of about 500 mg according once every three weeks (Q3W) for 5 cycles. In embodiments, a PD-1 binding agent is administered to a subject at a dose of about 1000 mg according once every six weeks or more (Q3W). In embodiments, a PD-1 binding agent is administered to a subject at a dose of about 1000 mg according once every six weeks (Q3W). In embodiments, a PD-1 binding agent is administered at a first dose of about 500 mg once every 3 weeks for 3 cycles followed by a second dose of about 1000 mg once every 6 weeks or more (e.g., until treatment is discontinued). In embodiments, a PD-1 binding agent is administered at a first dose of about 500 mg once every 3 weeks for 4 cycles followed by a second dose of about 1000 mg once every 6 weeks (e.g., until treatment is discontinued). In embodiments, a PD-1 binding agent is administered at a first dose of about 500 mg once every 3 weeks for 5 cycles followed by a second dose of about 1000 mg once every 6 weeks or more (e.g., until treatment is discontinued). In embodiments, a second dose is of about 1000 mg once every six weeks (e.g., until treatment is discontinued). In embodiments, a PD-1 binding agent is any anti-PD-1 antibody described herein.

In embodiments, a subject has been further administered or will be administered a further therapeutic agent, such that the subject receives a PD-1 binding agent and a further therapeutic agent (e.g., one, two, three, four, or more further therapeutic agents). In embodiments, a PD-1 binding agent is any anti-PD-1 antibody described herein.

In embodiments, a subject has been further administered or will be administered an immune checkpoint inhibitor, such that the subject receives a PD-1 binding agent and an immune checkpoint inhibitor. That is, a subject can be administered a PD-1 binding agent in combination with at least one immune checkpoint inhibitor. In embodiments, a PD-1 binding agent is any anti-PD-1 antibody described herein.

In embodiments, an immune checkpoint inhibitor is an agent capable of inhibiting any of the following: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, IDO, or CSF-1R. In embodiments, a checkpoint inhibitor is a small molecule, a nucleic acid, a polypeptide (e.g., an antibody), a carbohydrate, a lipid, a metal, or a toxin. In embodiments, a checkpoint inhibitor is an antibody, an antibody conjugate, or an antigen-binding fragment thereof.

In embodiments, an immune checkpoint inhibitor is an agent that inhibits T cell immunoglobulin and mucin protein 3 (TIM-3), cytotoxic T-lymphocyte-associated protein 4 (CTLA-4), lymphocyte activation gene-3 (LAG-3), T cell immunoglobulin and ITIM domain (TIGIT), indoleamine 2,3-dioxygenase (IDO), or colony stimulating factor 1 receptor (CSF1R).

In embodiments, an immune checkpoint inhibitor is a TIM-3 inhibitor. In embodiments, a TIM-3 inhibitor is a small molecule, a nucleic acid, a polypeptide (e.g., an antibody), a carbohydrate, a lipid, a metal, a toxin, or a binding agent. In embodiments, a TIM-3 inhibitor is a TIM-3 binding agent (e.g., an antibody, an antibody conjugate, or an antigen-binding fragment thereof). In embodiments, a TIM-3 inhibitor is a TIM-3 inhibitor described in WO 2016/161270, which is hereby incorporated by reference in its entirety. In embodiments, a TIM-3 inhibitor is TSR-022. For example, a TIM-3 inhibitor (e.g., TSR-022) can be administered in a dose of about 1, 3 or 10 mg/kg (e.g., about 1 mg/kg; about 3 mg/kg; or about 10 mg/kg) or a flat dose between about 100-1500 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg).

In embodiments, an immune checkpoint inhibitor is a CTLA-4 inhibitor (e.g., an antibody, an antibody conjugate, or an antigen-binding fragment thereof). In embodiments, a CTLA-4 inhibitor is a small molecule, a nucleic acid, a polypeptide (e.g., an antibody), a carbohydrate, a lipid, a metal, or a toxin. In embodiments, a CTLA-4 inhibitor is a small molecule. In embodiments, a CTLA-4 inhibitor is a CTLA-4 binding agent. In embodiments, a CTLA-4 inhibitor is an antibody, an antibody conjugate, or an antigen-binding fragment thereof. In embodiments, a CTLA-4 inhibitor is ipilimumab (Yervoy), AGEN1884, or tremelimumab.

In embodiments, an immune checkpoint inhibitor is a LAG-3 inhibitor (e.g., an antibody, an antibody conjugate, or an antigen-binding fragment thereof). In embodiments, a LAG-3 inhibitor is a small molecule, a nucleic acid, a polypeptide (e.g., an antibody), a carbohydrate, a lipid, a metal, or a toxin. In embodiments, a LAG-3 inhibitor is a small molecule. In embodiments, a LAG-3 inhibitor is a LAG-3 binding agent. In embodiments, a LAG-3 inhibitor is an antibody, an antibody conjugate, or an antigen-binding fragment thereof. In embodiments, a LAG-3 inhibitor is a IMP321, BMS-986016, GSK2831781, Novartis LAG525, or a LAG-3 inhibitor described in WO 2016/126858, WO 2017/019894, or WO 2015/138920, each of which is hereby incorporated by reference in its entirety.

In embodiments, an immune checkpoint inhibitor is a TIGIT inhibitor (e.g., an antibody, an antibody conjugate, or an antigen-binding fragment thereof). In embodiments, a TIGIT inhibitor is a small molecule, a nucleic acid, a polypeptide (e.g., an antibody), a carbohydrate, a lipid, a metal, or a toxin. In embodiments, a TIGIT inhibitor is small molecule. In embodiments, a TIGIT inhibitor is a TIGIT binding agent. In embodiments, a TIGIT inhibitor is an antibody, an antibody conjugate, or an antigen-binding fragment thereof. In embodiments, a TIGIT inhibitor is MTIG7192A, BMS-986207, or OMP-31M32.

In embodiments, an immune checkpoint inhibitor is an IDO inhibitor. In embodiments, an IDO inhibitor is a small molecule, a nucleic acid, a polypeptide (e.g., an antibody), a carbohydrate, a lipid, a metal, or a toxin. In embodiments, an IDO inhibitor is small molecule. In embodiments, an IDO inhibitor is an IDO binding agent. In embodiments, an IDO inhibitor is an antibody, an antibody conjugate, or an antigen-binding fragment thereof.

In embodiments, an immune checkpoint inhibitor is a CSF1R inhibitor. In embodiments, a CSF1R inhibitor is a small molecule, a nucleic acid, a polypeptide (e.g., an antibody), a carbohydrate, a lipid, a metal, or a toxin. In embodiments, a CSF1R inhibitor is small molecule. In embodiments, a CSF1R inhibitor is a CSF1R binding agent. In embodiments, a CSF1R inhibitor is an antibody, an antibody conjugate, or an antigen-binding fragment thereof.

In embodiments, a subject has been further administered or will be administered an agent that inhibits poly (ADP-ribose) polymerase (PARP), such that the subject receives treatment with a PD-1 binding agent and a PARP inhibitor.

In embodiments, a PARP inhibitor is a small molecule, a nucleic acid, a polypeptide (e.g., an antibody), a carbohydrate, a lipid, a metal, or a toxin. In embodiments, a PARP inhibitor is selected from the group consisting of: ABT-767, AZD 2461, BGB-290, BGP 15, CEP 8983, CEP 9722, DR 2313, E7016, E7449, fluzoparib, IMP 4297, INO1001, JPI 289, JPI 547, monoclonal antibody B3-LysPE40 conjugate, MP 124, niraparib, NU 1025, NU 1064, NU 1076, NU1085, olaparib, ONO2231, PD 128763, R 503, R554, rucaparib, SBP 101, SC 101914, simmiparib, talazoparib, veliparib, WW 46, 2-(4-(trifluoromethyl)phenyl)-7,8-dihydro-5H-thiopyrano[4,3-d]pyrimidin-4-ol, and salts or derivatives thereof. In embodiments, a PARP inhibitor is niraparib, olaparib, rucaparib, talazoparib, or veliparib. In embodiments, a PARP inhibitor is niraparib (e.g., niraparib free base, niraparib tosylate, or niraparib tosylate monohydrate, or any combination thereof).

In embodiments, a subject is further administered or will be administered one or more immune checkpoint inhibitors (e.g., a TIM-3 inhibitor and/or a LAG-3 inhibitor) such that the subject receives treatment with a PD-1 binding agent, a PARP inhibitor (e.g., niraparib), and the one or more immune checkpoint inhibitors. In embodiments, a subject is administered a PD-1 binding agent, a PARP inhibitor (e.g., niraparib), and a TIM-3 inhibitor. In embodiments, a subject is administered a PD-1 binding agent, a PARP inhibitor (e.g., niraparib), and a LAG-3 inhibitor. In embodiments, a subject is administered a PD-1 binding agent, a PARP inhibitor (e.g., niraparib), a TIM-3 inhibitor, and a LAG-3 inhibitor.

In embodiments, a therapeutic agent (e.g., a PD-1 binding agent, an immune checkpoint inhibitor, or a PARP inhibitor) described herein is administered according to dosing regimens demonstrated to achieve a clinical benefit in some patients (for example, according to a regimen as determined by a physician, including dosing modifications).

In some embodiments, a clinical benefit is a complete response ("CR"), a partial response ("PR") or a stable disease ("SD"). In some embodiments, a clinical benefit corresponds to at least SD. In some embodiments, a clinical benefit corresponds to at least a PR. In some embodiments, a clinical benefit corresponds to a CR. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, at least 5% of patients achieve a clinical benefit. In some embodiments, at least 5% of patients achieve SD. In some embodiments, at least 5% of patients achieve at least a PR. In some embodiments, at least 5% of patients achieve CR. In some embodiments, at least 10% of patients achieve a clinical benefit. In some embodiments, at least 10% of patients achieve SD. In some embodiments, at least 10% of patients achieve at least a PR. In some embodiments, at least 20% of patients achieve a clinical benefit. In some embodiments, at least 20% of patients achieve SD.

In some embodiments, the clinical benefit (e.g., SD, PR and/or CR) is determined in accordance with Response Evaluation Criteria in Solid Tumors (RECIST). In some embodiments, the clinical benefit (e.g., SD, PR and/or CR) is determined in accordance RECIST guidelines. In some embodiments, the clinical benefit (e.g., SD, PR and/or CR) is determined in accordance RECIST guidelines (version 1.1). In some embodiments, the clinical benefit (e.g., SD, PR and/or CR) is determined in accordance immune-related RECIST (irRECIST) guidelines. In some embodiments, tumor response can be assessed by either irRECIST or RECIST version 1.1. In some embodiments, tumor response can be assessed by both irRECIST and RECIST version 1.1. When used herein, the term "RECIST guidelines" can refer to RECIST 1.0, RECIST 1.1 or it RECIST interchangeably.

In embodiments, a patient has a disorder that is a T-cell dysfunctional disorder.

In embodiments, a patient has a disorder that is cancer.

In embodiments, a cancer is associated with a high tumor mutation burden (TMB).

In embodiments, a cancer is microsatellite stable (MSS).

In embodiments a cancer is characterized by microsatellite instability.

In embodiments, a cancer has a high microsatellite instability status (MSI-H).

In embodiments, a cancer has a low microsatellite instability status (MSI-L).

In embodiments, a cancer is associated with high TMB and MSI-H.

In embodiments, a cancer is associated with high TMB and MSI-L or MSS. In embodiments, a cancer is associated with high TMB and MSI-L. In embodiments, a cancer is associated with high TMB and MSS.

In embodiments, a cancer has a defective DNA mismatch repair system.

In embodiments, a cancer has a defect in a DNA mismatch repair gene.

In embodiments, a cancer is a hypermutated cancer.

In embodiments, a cancer has homologous recombination repair deficiency/homologous repair deficiency ("HRD").

In embodiments, a cancer comprises a mutation in polymerase delta (POLD).

In embodiments, a cancer comprises a mutation in polymerase epsilon (POLE).

In embodiments, a cancer is endometrial cancer (e.g., MSI-H or MSS/MSI-L endometrial cancer). In embodiments, a cancer is a MSI-H cancer comprising a mutation in POLE or POLD (e.g., a MSI-H non-endometrial cancer comprising a mutation in POLE or POLD). In embodiments, a cancer is breast cancer (e.g., triple negative breast cancer (TNBC)). In embodiments, a cancer is lung cancer (e.g., non-small cell lung cancer). In embodiments, a cancer is melanoma. In embodiments, a cancer is colorectal cancer. In embodiments, a cancer is squamous cell carcinoma of the anus, squamous cell carcinoma of the penis, squamous cell carcinoma of the cervix, squamous cell carcinoma of the vagina, or squamous cell carcinoma of the vulva.

In embodiments, a cancer is adenocarcinoma, endometrial cancer, breast cancer, ovarian cancer, cervical cancer, fallopian tube cancer, testicular cancer, primary peritoneal cancer, colon cancer, colorectal cancer, stomach cancer, small intestine cancer, squamous cell carcinoma of the anogenital region (e.g., squamous cell carcinoma of the anus, penis, cervix, vagina, or vulva), soft tissue sarcoma (e.g., leiomyosarcoma), melanoma, renal cell carcinoma, lung cancer, non-small cell lung cancer, adenocarcinoma of the lung, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor. In embodiments, a cancer is MSS or MSI-L, is characterized by microsatellite instability, is MSI-H, has high TMB, has high TMB and is MSS or MSI-L, has high TMB and is MSI-H, has a defective DNA mismatch repair system, has a defect in a DNA mismatch repair gene, is a hypermutated cancer, is an HRD cancer, comprises a mutation in polymerase delta (POLD) or comprises a mutation in polymerase epsilon (POLE).

In embodiments, a cancer has homologous recombination repair deficiency/homologous repair deficiency ("HRD"). In embodiments, a cancer is acute myeloid leukemia. In embodiments, a cancer is acute lymphoblastic leukemia. In embodiments, a cancer is non-Hodgkin's lymphoma. In embodiments, a cancer is Hodgkin's lymphoma. In embodiments, a cancer is neuroblastoma. In embodiments, a cancer is a CNS tumor. In embodiments, a cancer is diffuse intrinsic pontine glioma (DIPG). In embodiments, a cancer is Ewing's sarcoma. In embodiments, a cancer is embryonal rhabdomyosarcoma. In embodiments, a cancer is osteosarcoma. In embodiments, a cancer is Wilms tumor. In embodiments, a cancer is a soft tissue sarcoma (e.g., leiomyosarcoma).

In some embodiments, a patient has cancer, such as a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, a patient has an anal cancer, a fallopian tube cancer, an ovarian cancer, or a lung cancer. In some certain embodiments, a patient has a cancer of the anus. In some certain embodiments, a patient has a cancer of the fallopian tube(s). In some certain embodiments, a patient has an ovarian cancer. In some certain embodiments, a patient has a lung cancer.

In some embodiments, a patient has a cancer with microsatellite instability. In some embodiments, the microsatellite instability is considered high, wherein the instability is significantly higher than that observed in a control cell (e.g., MSI-H status). In some embodiments, the microsatellite instability is MSI-Low. In some embodiments, the microsatellite instability is microsatellite stable (e.g., MSS status). In some embodiments, a cancer with microsatellite instability is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, a cancer with microsatellite instability is an anal cancer, a fallopian tube cancer, an ovarian cancer, or a lung cancer. In some certain embodiments, a patient has an endometrial cancer with microsatellite instability. In some embodiments, a patient has an endometrial cancer that is microsatellite stable (MSS).

In some embodiments, a patient has a cancer characterized by PD-1 and/or PD-L1 expression. In some embodiments, a cancer has high PD-1 and/or PD-L1 expression (e.g., by high PD-1 and/or high PD-L1 expression). In some embodiment, a cancer characterized by PD-1 and/or PD-L1 expression is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, a cancer characterized by PD-1 and/or PD-L1 expression is an anal cancer, a fallopian tube cancer, an ovarian cancer, or a lung cancer.

In embodiments, a cancer is an advanced cancer. In embodiments, a cancer is a metastatic cancer. In embodiments, a cancer is a MSI-H cancer. In embodiments, a cancer is a MSS cancer. In embodiments, a cancer is a POLE-mutant cancer. In embodiments, a cancer is a POLD-mutant cancer. In embodiments, a cancer is a high TMB cancer. In embodiments, a cancer is associated with homologous recombination repair deficiency/homologous repair deficiency ("HRD").

In embodiments, a cancer is a solid tumor. In embodiments, a solid tumor is advanced. In embodiments, a solid tumor is a metastatic solid tumor. In embodiments, a solid tumor is a MSI-H solid tumor. In embodiments, a solid tumor is a MSS solid tumor. In embodiments, a solid tumor is a POLE-mutant solid tumor. In embodiments, a solid tumor is a POLD-mutant solid tumor. In embodiments, a solid tumor is a high TMB solid tumor. In embodiments, a solid tumor is associated with homologous recombination repair deficiency/homologous repair deficiency ("HRD").

In embodiments, a cancer is a non-endometrial cancer (e.g., a non-endometrial solid tumor). In embodiments, a non-endometrial cancer is an advanced cancer. In embodiments, a non-endometrial cancer is a metastatic cancer. In embodiments, a non-endometrial cancer is a MSI-H cancer. In embodiments, a non-endometrial cancer is a MSS cancer. In embodiments, a non-endometrial cancer is a POLE-mutant cancer. In embodiments, a non-endometrial cancer is a solid tumor (e.g., a MSS solid tumor, a MSI-H solid tumor, a POLD mutant solid tumor, or a POLE-mutant solid tumor). In embodiments, a non-endometrial cancer is a high TMB cancer. In embodiments, a non-endometrial cancer is associated with homologous recombination repair deficiency/homologous repair deficiency ("HRD").

In embodiments, a cancer is endometrial cancer (e.g., a solid tumor). In embodiments, an endometrial cancer is an advanced cancer. In embodiments, an endometrial cancer is a metastatic cancer. In embodiments, an endometrial cancer is a MSI-H endometrial cancer. In embodiments, an endometrial cancer is a MSS endometrial cancer. In embodiments, an endometrial cancer is a POLE-mutant endometrial cancer. In embodiments, an endometrial cancer is a POLD-mutant endometrial cancer. In embodiments, an endometrial cancer is a high TMB endometrial cancer. In embodiments, an endometrial cancer is associated with homologous recombination repair deficiency/homologous repair deficiency ("HRD").

In embodiments, a cancer is a lung cancer (e.g., a solid tumor). In embodiments, a lung cancer is an advanced lung cancer. In embodiments, a lung cancer is a metastatic lung cancer. In embodiments, a lung cancer is squamous cell carcinoma of the lung. In embodiments, a lung cancer is small cell lung cancer (SCLC). In embodiments, a lung cancer is non-small cell lung cancer (NSCLC). In embodiments, a lung cancer is an ALK-translocated lung cancer (e.g., a lung cancer with a known ALK-translocation). In embodiments, a lung cancer is an EGFR-mutant lung cancer (e.g., a lung cancer with a known EGFR mutation). In embodiments, a lung cancer is a MSI-H lung cancer. In embodiments, a lung cancer is a MSS lung cancer. In embodiments, a lung cancer is a POLE-mutant lung cancer. In embodiments, a lung cancer is a POLD-mutant lung cancer. In embodiments, a lung cancer is a high TMB lung cancer. In embodiments, a lung cancer is associated with homologous recombination repair deficiency/homologous repair deficiency ("HRD").

In embodiments, a cancer is a colorectal (CRC) cancer (e.g., a solid tumor). In embodiments, a colorectal cancer is an advanced colorectal cancer. In embodiments, a colorectal cancer is a metastatic colorectal cancer. In embodiments, a colorectal cancer is a MSI-H colorectal cancer. In embodiments, a colorectal cancer is a MSS colorectal cancer. In embodiments, a colorectal cancer is a POLE-mutant colorectal cancer. In embodiments, a colorectal cancer is a POLD-mutant colorectal cancer. In embodiments, a colorectal cancer is a high TMB colorectal cancer. In embodiments, a colorectal cancer is associated with homologous recombination repair deficiency/homologous repair deficiency ("HRD").

In embodiments, a cancer is a melanoma. In embodiments, a melanoma is an advanced melanoma. In embodiments, a melanoma is a metastatic melanoma. In embodiments, a melanoma is a MSI-H melanoma. In embodiments, a melanoma is a MSS melanoma. In embodiments, a melanoma is a POLE-mutant melanoma. In embodiments, a melanoma is a POLD-mutant melanoma. In embodiments, a melanoma is a high TMB melanoma. In embodiments, a melanoma is associated with homologous recombination repair deficiency/homologous repair deficiency ("HRD").

In embodiments, a cancer is squamous cell carcinoma of the anogenital region (e.g., of the anus, penis, cervix, vagina, or vulva). In embodiments, a squamous cell carcinoma of the anogenital region (e.g., of the anus, penis, cervix, vagina, or vulva) is an advanced cancer. In embodiments, a squamous cell carcinoma of the anogenital region (e.g., of the anus, penis, cervix, vagina, or vulva) is a metastatic cancer. In embodiments, a squamous cell carcinoma of the anogenital region (e.g., of the anus, penis, cervix, vagina, or vulva) is MSI-H. In embodiments, a squamous cell carcinoma of the anogenital region (e.g., of the anus, penis, cervix, vagina, or vulva) is MSS. In embodiments, a lung cancer is a POLE-mutant cancer. In embodiments, a squamous cell carcinoma of the anogenital region (e.g., of the anus, penis, cervix, vagina, or vulva) is associated with homologous recombination repair deficiency/homologous repair deficiency ("HRD").

In embodiments, a cancer is an ovarian cancer. In embodiments, an ovarian cancer is an advanced ovarian cancer. In embodiments, an ovarian cancer is a metastatic ovarian cancer. In embodiments, an ovarian cancer is a MSI-H ovarian cancer. In embodiments, an ovarian cancer is a MSS ovarian cancer. In embodiments, an ovarian cancer is a POLE-mutant ovarian cancer. In embodiments, an ovarian cancer is a POLD-mutant ovarian cancer. In embodiments, an ovarian cancer is a high TMB ovarian cancer. In embodiments, an ovarian cancer is associated with homologous recombination repair deficiency/homologous repair deficiency ("HRD"). In embodiments, an ovarian cancer is a serous cell ovarian cancer. In embodiments, an ovarian cancer is a clear cell ovarian cancer.

In embodiments, a cancer is a fallopian cancer. In embodiments, a fallopian cancer is an advanced fallopian cancer. In embodiments, a fallopian cancer is a metastatic fallopian cancer. In embodiments, a fallopian cancer is a MSI-H fallopian cancer. In embodiments, a fallopian cancer is a MSS fallopian cancer. In embodiments, a fallopian cancer is a POLE-mutant fallopian cancer. In embodiments, a fallopian cancer is a POLD-mutant fallopian cancer. In embodiments, a fallopian cancer is a high TMB fallopian cancer. In embodiments, a fallopian cancer is associated with homologous recombination repair deficiency/homologous repair deficiency ("HRD"). In embodiments, a fallopian cancer is a serous cell fallopian cancer. In embodiments, a fallopian cancer is a clear cell fallopian cancer.

In embodiments, a cancer is a primary peritoneal cancer. In embodiments, a primary peritoneal cancer is an advanced primary peritoneal cancer. In embodiments, a primary peritoneal cancer is a metastatic primary peritoneal cancer. In embodiments, a primary peritoneal cancer is a MSI-H primary peritoneal cancer. In embodiments, a primary peritoneal cancer is a MSS primary peritoneal cancer. In embodiments, a primary peritoneal cancer is a POLE-mutant primary peritoneal cancer. In embodiments, a primary peritoneal cancer is a POLD-mutant primary peritoneal cancer. In embodiments, a primary peritoneal cancer is a high TMB primary peritoneal cancer. In embodiments, a primary peritoneal cancer is associated with homologous recombination repair deficiency/homologous repair deficiency ("HRD"). In embodiments, a primary peritoneal cancer is a serous cell primary peritoneal cancer. In embodiments, a primary peritoneal cancer is a clear cell primary peritoneal cancer.

In embodiments, a cancer is acute lymphoblastic leukemia ("ALL"). In embodiments, acute lymphoblastic leukemia is advanced acute lymphoblastic leukemia. In embodiments, acute lymphoblastic leukemia is metastatic acute lymphoblastic leukemia. In embodiments, acute lymphoblastic leukemia is MSI-H acute lymphoblastic leukemia. In embodiments, acute lymphoblastic leukemia is MSS acute lymphoblastic leukemia. In embodiments, acute lymphoblastic leukemia is POLE-mutant acute lymphoblastic leukemia. In embodiments, acute lymphoblastic leukemia is POLD-mutant acute lymphoblastic leukemia. In embodiments, an acute lymphoblastic leukemia is associated with homologous recombination repair deficiency/homologous repair deficiency ("HRD").

In embodiments, a cancer is acute myeloid leukemia ("AML"). In embodiments, acute myeloid leukemia is advanced acute myeloid leukemia. In embodiments, acute myeloid leukemia is metastatic acute myeloid leukemia. In embodiments, acute myeloid leukemia is MSI-H acute myeloid leukemia. In embodiments, acute myeloid leukemia is MSS acute myeloid leukemia. In embodiments, acute myeloid leukemia is POLE-mutant acute myeloid leukemia. In embodiments, acute myeloid leukemia is POLD-mutant acute myeloid leukemia. In embodiments, an acute myeloid leukemia is associated with homologous recombination repair deficiency/homologous repair deficiency ("HRD").

In embodiments, a cancer is non-Hodgkin's lymphoma (NHL). In embodiments, non-Hodgkin's lymphoma is advanced non-Hodgkin's lymphoma. In embodiments, non-Hodgkin's lymphoma is metastatic non-Hodgkin's lymphoma. In embodiments, non-Hodgkin's lymphoma is MSI-H non-Hodgkin's lymphoma. In embodiments, non-Hodgkin's lymphoma is MSS non-Hodgkin's lymphoma. In embodiments, non-Hodgkin's lymphoma is POLE-mutant non-Hodgkin's lymphoma. In embodiments, non-Hodgkin's lymphoma is POLD-mutant non-Hodgkin's lymphoma. In embodiments, non-Hodgkin's lymphoma is associated with homologous recombination repair deficiency/homologous repair deficiency ("HRD").

In embodiments, a cancer is Hodgkin's lymphoma (HL). In embodiments, Hodgkin's lymphoma is advanced Hodgkin's lymphoma. In embodiments, Hodgkin's lymphoma is metastatic Hodgkin's lymphoma. In embodiments, Hodgkin's lymphoma is MSI-H Hodgkin's lymphoma. In embodiments, Hodgkin's lymphoma is MSS Hodgkin's lymphoma. In embodiments, Hodgkin's lymphoma is POLE-mutant Hodgkin's lymphoma. In embodiments, Hodgkin's lymphoma is POLD-mutant Hodgkin's lymphoma. In embodiments, Hodgkin's lymphoma is associated with homologous recombination repair deficiency/homologous repair deficiency ("HRD").

In embodiments, a cancer is a neuroblastoma (NB). In embodiments, a neuroblastoma is an advanced neuroblastoma. In embodiments, a neuroblastoma is a metastatic neuroblastoma. In embodiments, neuroblastoma is a MSI-H neuroblastoma. In embodiments, a neuroblastoma is a MSS neuroblastoma. In embodiments, a neuroblastoma is a POLE-mutant neuroblastoma. In embodiments, a neuroblastoma is a POLD-mutant neuroblastoma. In embodiments, a neuroblastoma is a high TMB neuroblastoma. In embodiments, a neuroblastoma is associated with homologous recombination repair deficiency/homologous repair deficiency ("HRD").

In embodiments, a cancer is a CNS tumor. In embodiments, a CNS tumor is advanced. In embodiments, a CNS tumor is a metastatic CNS tumor. In embodiments, a CNS tumor is a MSI-H CNS tumor. In embodiments, a CNS tumor is a MSS CNS tumor. In embodiments, a CNS tumor is a POLE-mutant CNS tumor. In embodiments, a CNS tumor is a POLD-mutant CNS tumor. In embodiments, a CNS tumor is a high TMB CNS tumor. In embodiments, a CNS tumor is associated with homologous recombination repair deficiency/homologous repair deficiency ("HRD").

In embodiments, a cancer is diffuse intrinsic pontine glioma (DIPG). In embodiments, a DIPG is an advanced DIPG. In embodiments, a DIPG is a metastatic DIPG. In embodiments, DIPG is a MSI-H DIPG. In embodiments, a DIPG is a MSS DIPG. In embodiments, a DIPG is a POLE-mutant DIPG. In embodiments, a DIPG is a POLD-mutant DIPG. In embodiments, a DIPG is a high TMB DIPG. In embodiments, a DIPG is associated with homologous recombination repair deficiency/homologous repair deficiency ("HRD").

In embodiments, a cancer is Ewing's sarcoma. In embodiments, Ewing's sarcoma is an advanced Ewing's sarcoma. In embodiments, Ewing's sarcoma is a metastatic Ewing's sarcoma. In embodiments, Ewing's sarcoma is a MSI-H Ewing's sarcoma. In embodiments, Ewing's sarcoma is a MSS Ewing's sarcoma. In embodiments, Ewing's sarcoma is a POLE-mutant Ewing's sarcoma. In embodiments, Ewing's sarcoma is a POLD-mutant Ewing's sarcoma. In embodiments, Ewing's sarcoma is a high TMB Ewing's sarcoma. In embodiments, Ewing's sarcoma is associated with homologous recombination repair deficiency/homologous repair deficiency ("HRD").

In embodiments, a cancer is an embryonal rhabdomyosarcoma (ERS). In embodiments, an embryonal rhabdomyosarcoma is an advanced embryonal rhabdomyosarcoma. In embodiments, an embryonal rhabdomyosarcoma is a metastatic embryonal rhabdomyosarcoma. In embodiments, an embryonal rhabdomyosarcoma is a MSI-H embryonal rhabdomyosarcoma. In embodiments, an embryonal rhabdomyosarcoma is a MSS embryonal rhabdomyosarcoma. In embodiments, an embryonal rhabdomyosarcoma is a POLE-mutant embryonal rhabdomyosarcoma. In embodiments, an embryonal rhabdomyosarcoma is a POLD-mutant embryonal rhabdomyosarcoma. In embodiments, an embryonal rhabdomyosarcoma is a high TMB embryonal rhabdomyosarcoma. In embodiments, an embryonal rhabdomyosarcoma is associated with homologous recombination repair deficiency/homologous repair deficiency ("HRD").

In embodiments, a cancer is an osteosarcoma (OS). In embodiments, an osteosarcoma is an advanced osteosarcoma. In embodiments, an osteosarcoma is a metastatic osteosarcoma. In embodiments, an osteosarcoma is a MSI-H osteosarcoma. In embodiments, an osteosarcoma is a MSS osteosarcoma. In embodiments, an osteosarcoma is a POLE-mutant osteosarcoma. In embodiments, an osteosarcoma is a POLD-mutant osteosarcoma. In embodiments, an osteosarcoma is a high TMB osteosarcoma. In embodiments, an osteosarcoma is associated with homologous recombination repair deficiency/homologous repair deficiency ("HRD").

In embodiments, a cancer is a soft tissue sarcoma. In embodiments, a soft tissue sarcoma is an advanced soft tissue sarcoma. In embodiments, a soft tissue sarcoma is a metastatic soft tissue sarcoma. In embodiments, a soft tissue sarcoma is a MSI-H soft tissue sarcoma. In embodiments, a soft tissue sarcoma is a MSS soft tissue sarcoma. In embodiments, a soft tissue sarcoma is a POLE-mutant soft tissue sarcoma. In embodiments, a soft tissue sarcoma is a POLD-mutant soft tissue sarcoma. In embodiments, a soft tissue sarcoma is a high TMB soft tissue sarcoma. In embodiments, a soft tissue sarcoma is associated with homologous recombination repair deficiency/homologous repair deficiency ("HRD"). In embodiments, a soft tissue sarcoma is leiomyosarcoma.

In embodiments, a cancer is Wilms tumor. In embodiments, Wilms tumor is an advanced Wilms tumor. In embodiments, Wilms tumor is a metastatic Wilms tumor. In embodiments, Wilms tumor is a MSI-H Wilms tumor. In embodiments, Wilms tumor is a MSS Wilms tumor. In embodiments, Wilms tumor is a POLE-mutant Wilms tumor. In embodiments, Wilms tumor is a POLD-mutant Wilms tumor. In embodiments, Wilms tumor is a high TMB Wilms tumor. In embodiments, Wilms tumor is associated with homologous recombination repair deficiency/homologous repair deficiency ("HRD").

In embodiments, a subject has previously been treated with one or more different cancer treatment modalities (e.g., one or more of surgery, radiotherapy, chemotherapy, or immunotherapy). In embodiments, a subject has previously been treated with one different cancer treatment modalities (e.g., one or more of surgery, radiotherapy, chemotherapy, or immunotherapy). In embodiments, a subject has previously been treated with two or more different cancer treatment modalities (e.g., one or more of surgery, radiotherapy, chemotherapy, or immunotherapy). In embodiments, a subject has been previously treated with a cytotoxic therapy. In embodiments, a subject has been previously treated with chemotherapy. In embodiments, a subject has previously been treated with two different cancer treatment modalities (e.g., one or more of surgery, radiotherapy, chemotherapy, or immunotherapy). In embodiments, a subject has previously been treated with three different cancer treatment modalities (e.g., one or more of surgery, radiotherapy, chemotherapy, or immunotherapy).

In embodiments of methods described herein, a method further comprises administering one or more of surgery, a radiotherapy, a chemotherapy, an immunotherapy, an anti-angiogenic agent, or an anti-inflammatory. In embodiments, a method further comprises administering a chemotherapy.

In embodiments, a subject is resistant to treatment with an agent that inhibits PD-1.

In embodiments, a subject is refractory to treatment with an agent that inhibits PD-1.

In embodiments, a method described herein sensitizes a subject to treatment with an agent that inhibits PD-1.

In embodiments, a subject comprises an exhausted immune cell (e.g., an exhausted immune cell that is an exhausted T cell).

In embodiments of methods described herein, a subject is an animal (e.g., a mammal). In embodiments, a subject is a human. In embodiments, a subject is a non-human mammal (e.g., mice, rats, rabbits, or non-human primates). Accordingly, methods described herein can be useful in both treatment of humans and in veterinary medicine.

In embodiments, a PD-1 binding agent (e.g., any anti-PD-1 antibody) is administered intravenously (e.g., by intravenous infusion).

The present disclosure also provides, in some embodiments, methods of treating cancer that comprises administering to a patient in need of treatment an anti-programmed death-1 protein (PD-1) antibody at a therapeutically effective dose at an administration interval for a period sufficient to achieve clinical benefit. In embodiments, the anti-PD-1 antibody comprises a heavy chain variable region comprising CDR sequences of SEQ ID NOs: 9, 10, and 11 and a light chain variable region comprising CDR sequences of SEQ ID NOs: 12, 13, and 14. In embodiments, the heavy chain variable region comprises SEQ ID NO: 1 and the light chain variable domain comprises SEQ ID NO: 2. In embodiments, the heavy chain variable region comprises SEQ ID NO:7 and the light chain variable region comprises SEQ ID NO:8. In embodiments, the heavy chain variable region comprises SEQ ID NO: 3 and the light chain variable region comprises SEQ ID NO: 4.

The present disclosure provides, in some embodiments, methods of treating cancer in a patient in need thereof, the method comprising administering a composition that delivers a PD-1-binding agent according to a regimen demonstrated to achieve a response rate in relevant patient population such that no more than 50% to 80% of patients show progressive disease after 2, 4, 6, 8, 10, 12, 14, 16, 18, or 20 weeks following initiation of treatment. In some embodiments, no more than 80% of patients show progressive disease after at least 10 weeks following initiation of treatment.

In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, methods of treating cancer in a patient in need thereof, the method comprising administering a composition that delivers a PD-1-binding agent sufficient to achieve an average PD-1 receptor occupancy of at least about 50% to about 90% after 1, 2, 3, 4, or 5 days following a single dose of the composition. In some embodiments, administration of a composition that delivers a PD-1-binding agent is sufficient to achieve an average PD-1 receptor occupancy of at least 85% after 3 days following a single dose of the composition. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, methods of treating cancer in a patient in need thereof, the method comprising administering a composition that delivers a PD-1-binding agent sufficient to achieve an average stimulation ratio of at least 1 in a functional PD-1 receptor occupancy assay after 3 days following a single dose of the PD-1-binding agent. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, methods of treating cancer in a patient in need thereof, the method comprising administering a composition that delivers a PD-1-binding agent sufficient to achieve an average PD-1 receptor occupancy of at least 75% over a first period of time (e.g., about 15 days to about 60 days; in some embodiments about 29 days) following a single dose of the PD-1-binding agent. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, methods of treating cancer in a patient in need thereof, the method comprising administering a composition that delivers a PD-1-binding agent sufficient to achieve an average stimulation ratio of at least 1 in a functional PD-1 receptor occupancy assay over a first period of time (e.g., about 15 days to about 60 days; in some embodiments about 29 days) following a single dose of the PD-1-binding agent. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

In some embodiments, a patient for treatment with a composition for delivering a PD-1 binding agent has a tumor. In some embodiments, the patient has a solid tumor. In some embodiments, the patient has an advanced stage solid tumor. In some embodiments, a patient has a metastatic solid tumor.

In some embodiments, the patient has a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, an endometrial cancer, an ovarian cancer, a fallopian tube cancer, a breast cancer, a prostate cancer, a salivary gland tumor, a thymoma, an adrenocortical carcinoma, an esophageal cancer, a gastric cancer, a colorectal cancer, an appendiceal cancer, a urothelial cell carcinoma, or a squamous cell carcinoma.

In some embodiments, the patient has an advanced stage cancer, including an advanced stage head and neck cancer, lung cancer (e.g., non-small cell lung cancer (NSCLC)), renal cancer, bladder cancer, melanoma, Merkel cell carcinoma, cervical cancer, vaginal cancer, vulvar cancer, uterine cancer, endometrial cancer, ovarian cancer, fallopian tube cancer, breast cancer, prostate cancer, salivary gland tumor, thymoma, adrenocortical carcinoma, esophageal cancer, gastric cancer, colorectal cancer, urothelial cell carcinoma, or squamous cell carcinoma (e.g., of the lung; of the anogenital region including anus, penis, cervix, vagina, or vulva; or of the esophagus). In some certain embodiments, a patient has an advanced stage anal cancer, fallopian tube cancer, ovarian cancer, breast cancer, endometrial cancer, or lung cancer. In some embodiments, the patient has an advanced stage cancer such as an advanced stage endometrial cancer, triple negative breast cancer, ovarian cancer, non-small cell lung cancer, squamous cell carcinoma of the lung, or squamous cell carcinoma of the anogenital region (e.g., squamous cell carcinoma of the anus, penis, cervix, vagina, or vulva).

In some embodiments, the patient has a cancer associated with a POLE (DNA polymerase epsilon) or a POLD (DNA polymerase delta) mutation. In some embodiments, the POLE or POLD mutation is in an exonuclease domain. In some embodiments, the POLE or POLD mutation is a germline mutation. In some embodiments, the POLE or POLD mutation is a sporadic mutation. In some embodiments, a method described herein further comprises a step of first identifying the patient having the cancer with the POLE or POLD mutation. In some embodiments, a POLE or POLD mutation is identified using sequencing.

In some embodiments, a patient has a cancer with microsatellite instability (e.g., MSI-H status). In some embodiments, the microsatellite instability is MSI-Low. In some embodiments, the microsatellite instability is microsatellite stable (e.g., MSS status). In some embodiments, the patient has endometrial cancer. In some embodiments, a patient has an endometrial cancer with microsatellite instability. In some embodiments, a patient has an advanced stage cancer with microsatellite instability. In some embodiments, an advanced stage cancer with microsatellite instability is an endometrial cancer, a triple negative breast cancer, an ovarian cancer, a non-small cell lung cancer, a squamous cell carcinoma of the lung, or a squamous cell carcinoma of the anogenital region (e.g., squamous cell carcinoma of the anus, penis, cervix, vagina, or vulva). In some embodiments, the patient has a solid tumor (e.g., an advanced stage solid tumor or a metastatic solid tumor). In some embodiments, the patient has a MSI-H solid tumor.

In some embodiments, the patient has a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In some embodiments, a patient has a hematological cancer with microsatellite instability.

In some embodiments, the patient has not previously been treated with a cancer treatment modality.

In some embodiments, the patient has previously been treated with one or more different cancer treatment modalities. In some embodiments, the patient has previously been treated with one or more of surgery, radiotherapy, chemotherapy or immunotherapy. In some embodiments, the patient has previously been treated with surgery. In some embodiments, the patient has previously been treated with chemotherapy (e.g., platinum-based chemotherapy). In some such embodiments, the platinum agent is selected from cisplatin, carboplatin, oxaliplatin, nedaplatin, triplatin tetranitrate, phenanthriplatin, picoplatin, or satraplatin. In some embodiments, a patient has a cancer that has responded to platinum induction therapy. In some embodiments, the cancer is platinum sensitive at the commencement of treatment. In some embodiments, the cancer responded to the most recent platinum-based chemotherapy regimen prior to commencement of treatment. In some embodiments, response to the most recent platinum-based chemotherapy regimen is a complete response. In some embodiments, response to the most recent platinum-based chemotherapy regimen is a partial response.

In some embodiments, a composition that delivers a PD-1-binding agent (e.g., an anti-PD-1 antibody) is administered in an amount that delivers a dose of 1, 3 or 10 mg/kg PD-1-binding agent. In some embodiments, a PD-1-binding agent (e.g., an anti-PD-1 antibody) is administered according to a regimen that delivers a dose of 1, 3 or 10 mg/kg every two weeks. In some embodiments, a PD-1-binding agent (e.g., an anti-PD-1 antibody) is administered according to a regimen that delivers a dose of 1, 3 or 10 mg/kg every three weeks. In some embodiments, a PD-1-binding agent (e.g., an anti-PD-1 antibody) is administered according to a regimen that delivers a dose of 1, 3 or 10 mg/kg every four weeks.

In some embodiments, a composition that delivers a PD-1-binding agent (e.g., an anti-PD-1 antibody) is administered in an amount that delivers a dose (e.g., a therapeutically effective dose) within a range of about 100 mg to about 2,000 mg of PD-1-binding agent. In some embodiments, a PD-1-binding agent (e.g., an anti-PD-1 antibody) is administered at a dose ranging from about 100 mg to about 1,200 mg, such as a therapeutically effective dose that is about 100 mg, about 300 mg, about 500 mg, or about 1000 mg. In some embodiments, a PD-1-binding agent (e.g., an anti-PD-1 antibody) is administered at a dose of about 400 mg, about 500 mg, about 800 mg, and/or about 1000 mg of PD-1-binding agent. In some embodiments, a dose of a particular PD-1 binding agent is considered to be "a dose of about [an indicated amount]" if it achieves a relevant biological or pharmacological effect that is comparable to that achieved with a dose of the indicated amount of a particular reference PD-1 binding agent (e.g., a particular anti-PD-1 antibody, such as a particular anti-PD-1 monoclonal antibody or other anti-PD-1 antibody agent including, for example, an anti-PD-1 antibody exemplified herein). In some embodiments, such a dose of the particular PD-1 binding agent may be described as a dose "corresponding to" the indicated amount of the reference PD-1 binding agent.

In some embodiments, a PD-1-binding agent (e.g., an anti-PD-1 antibody) is administered according to a regimen that includes a plurality of individual doses (e.g., as set forth above), separated from each other by a period of time. In some embodiments, individual doses may be separated from each other by a period of two weeks, three weeks, four weeks, five weeks, six weeks or more. In embodiments, the anti-PD-1 antibody is administered at the administration interval of once a week, once every 2 weeks, once every 3 weeks, once every 4 weeks, once every 5 weeks, or once every 6 weeks. In embodiments, the administration interval is once every 3 weeks. In embodiments, the administration interval is once every 6 weeks. In embodiments, the anti-PD-1 antibody is administered for the period of at least 2, 4, 6, 8, 10, 12, 14, 16, 18, or 20 weeks.

In some embodiments, a PD-1-binding agent (e.g., an anti-PD-1 antibody) is administered at a dose of 100 mg of PD-1-binding agent. In some embodiments, a PD-1-binding agent (e.g., an anti-PD-1 antibody) is administered according to a regimen that delivers a dose of 100 mg every two weeks. In some embodiments, a PD-1-binding agent (e.g., an anti-PD-1 antibody) is administered according to a regimen that delivers a dose of 100 mg every three weeks. In some embodiments, a PD-1-binding agent (e.g., an anti-PD-1 antibody) is administered according to a regimen that delivers a dose of 100 mg every four weeks. In some embodiments, a PD-1-binding agent (e.g., an anti-PD-1 antibody) is administered according to a regimen that delivers a dose of 100 mg every five weeks. In some embodiments, a PD-1-binding agent (e.g., an anti-PD-1 antibody) is administered at a dose of 100 mg every six weeks.

In some embodiments, a PD-1-binding agent (e.g., an anti-PD-1 antibody) is administered at a dose of 300 mg of PD-1-binding agent. In some embodiments, a PD-1-binding agent (e.g., an anti-PD-1 antibody) is administered according to a regimen that delivers a dose of 300 mg every two weeks. In some embodiments, a PD-1-binding agent (e.g., an anti-PD-1 antibody) is administered according to a regimen that delivers a dose of 300 mg every three weeks. In some embodiments, a PD-1-binding agent (e.g., an anti-PD-1 antibody) is administered according to a regimen that delivers a dose of 300 mg every four weeks. In some embodiments, a PD-1-binding agent (e.g., an anti-PD-1 antibody) is administered according to a regimen that delivers a dose of 300 mg every five weeks. In some embodiments, a PD-1-binding agent (e.g., an anti-PD-1 antibody) is administered at a dose of 300 mg every six weeks.

In some embodiments, a PD-1-binding agent (e.g., an anti-PD-1 antibody) is administered at a dose of 400 mg of PD-1-binding agent. In some embodiments, a PD-1-binding agent (e.g., an anti-PD-1 antibody) is administered according to a regimen that delivers a dose of 400 mg every two weeks. In some embodiments, a PD-1-binding agent (e.g., an anti-PD-1 antibody) is administered according to a regimen that delivers a dose of 400 mg every three weeks. In some embodiments, a PD-1-binding agent (e.g., an anti-PD-1 antibody) is administered according to a regimen that delivers a dose of 400 mg every four weeks. In some embodiments, a PD-1-binding agent (e.g., an anti-PD-1 antibody) is administered according to a regimen that delivers a dose of 400 mg every five weeks. In some embodiments, a PD-1-binding agent (e.g., an anti-PD-1 antibody) is administered at a dose of 400 mg every six weeks.

In some embodiments, a PD-1-binding agent (e.g., an anti-PD-1 antibody) is administered at a dose of 500 mg. In some embodiments, a PD-1-binding agent (e.g., an anti-PD-1 antibody) is administered according to a regimen that delivers a dose of 500 mg every two weeks. In some embodiments, a PD-1-binding agent (e.g., an anti-PD-1 antibody) is administered according to a regimen that delivers a dose of 500 mg every three weeks. In some embodiments, a PD-1-binding agent (e.g., an anti-PD-1 antibody) is administered according to a regimen that delivers a dose of 500 mg every four weeks. In some embodiments, a PD-1-binding agent (e.g., an anti-PD-1 antibody) is administered according to a regimen that delivers a dose of 500 mg every five weeks. In some embodiments, a PD-1-binding agent (e.g., an anti-PD-1 antibody) is administered according to a regimen that delivers a dose of 500 mg every six weeks.

In some embodiments, a PD-1-binding agent (e.g., an anti-PD-1 antibody) is administered at a dose of 600 mg. In some embodiments, a PD-1-binding agent (e.g., an anti-PD-1 antibody) is administered according to a regimen that delivers a dose of 600 mg every two weeks. In some embodiments, a PD-1-binding agent (e.g., an anti-PD-1 antibody) is administered according to a regimen that delivers a dose of 600 mg every three weeks. In some embodiments, a PD-1-binding agent (e.g., an anti-PD-1 antibody) is administered according to a regimen that delivers a dose of 600 mg every four weeks. In some embodiments, a PD-1-binding agent (e.g., an anti-PD-1 antibody) is administered according to a regimen that delivers a dose of 600 mg every five weeks. In some embodiments, a PD-1-binding agent (e.g., an anti-PD-1 antibody) is administered according to a regimen that delivers a dose of 600 mg every six weeks.

In some embodiments, a PD-1-binding agent (e.g., an anti-PD-1 antibody) is administered at a dose of 700 mg. In some embodiments, a PD-1-binding agent (e.g., an anti-PD-1 antibody) is administered according to a regimen that delivers a dose of 700 mg every four weeks. In some embodiments, a PD-1-binding agent (e.g., an anti-PD-1 antibody) is administered according to a regimen that delivers a dose of 700 mg every five weeks. In some embodiments, a PD-1-binding agent (e.g., an anti-PD-1 antibody) is administered according to a regimen that delivers a dose of 700 mg every six weeks. In some embodiments, a PD-1-binding agent (e.g., an anti-PD-1 antibody) is administered according to a regimen that delivers a dose of 700 mg every seven weeks. In some embodiments, a PD-1-binding agent (e.g., an anti-PD-1 antibody) is administered according to a regimen that delivers a dose of 700 mg every eight weeks.

In some embodiments, a PD-1-binding agent (e.g., an anti-PD-1 antibody) is administered at a dose of 800 mg. In some embodiments, a PD-1-binding agent (e.g., an anti-PD-1 antibody) is administered according to a regimen that delivers a dose of 800 mg every four weeks. In some embodiments, a PD-1-binding agent (e.g., an anti-PD-1 antibody) is administered according to a regimen that delivers a dose of 800 mg every five weeks. In some embodiments, a PD-1-binding agent (e.g., an anti-PD-1 antibody) is administered according to a regimen that delivers a dose of 800 mg every six weeks. In some embodiments, a PD-1-binding agent (e.g., an anti-PD-1 antibody) is administered according to a regimen that delivers a dose of 800 mg every eight weeks.

In some embodiments, a PD-1-binding agent (e.g., an anti-PD-1 antibody) is administered at a dose of 900 mg. In some embodiments, a PD-1-binding agent (e.g., an anti-PD-1 antibody) is administered according to a regimen that delivers a dose of 900 mg every four weeks. In some embodiments, a PD-1-binding agent (e.g., an anti-PD-1 antibody) is administered according to a regimen that delivers a dose of 900 mg every five weeks. In some embodiments, a PD-1-binding agent (e.g., an anti-PD-1 antibody) is administered according to a regimen that delivers a dose of 900 mg every six weeks. In some embodiments, a PD-1-binding agent (e.g., an anti-PD-1 antibody) is administered according to a regimen that delivers a dose of 900 mg every seven weeks. In some embodiments, a PD-1-binding agent (e.g., an anti-PD-1 antibody) is administered according to a regimen that delivers a dose of 900 mg every eight weeks.

In some embodiments, a PD-1-binding agent (e.g., an anti-PD-1 antibody) is administered at a dose of 1,000 mg. In some embodiments, a PD-1-binding agent (e.g., an anti-PD-1 antibody) is administered according to a regimen that delivers a dose of 1,000 mg every four weeks. In some embodiments, a PD-1-binding agent (e.g., an anti-PD-1 antibody) is administered according to a regimen that delivers a dose of 1,000 mg every five weeks. In some embodiments, a PD-1-binding agent (e.g., an anti-PD-1 antibody) is administered according to a regimen that delivers a dose of 1,000 mg every six weeks. In some embodiments, a PD-1-binding agent (e.g., an anti-PD-1 antibody) is administered according to a regimen that delivers a dose of 1,000 mg every seven weeks. In some embodiments, a PD-1-binding agent (e.g., an anti-PD-1 antibody) is administered according to a regimen that delivers a dose of 1,000 mg every eight weeks.

In some particular embodiments, a PD-1 binding agent (e.g., an anti-PD1 antibody) is administered according to a regimen that comprises or consists of at least one cycle of: a single dose (e.g., a single 400 mg dose or a single 500 mg dose) once every two weeks, a single dose once every three weeks, a single dose once every four weeks, a single dose once every five weeks, a single dose once every six weeks, etc. In some embodiments, a cycle includes 1, 2, 3, 4, 5, 6, 7, 8, 9, 10 or more single doses. In some embodiments, a regimen includes a plurality of cycles. In some embodiments, individual cycles may be separated from one another by a period of rest (i.e., no dosing).

In embodiments, a PD-1 inhibitor (e.g., any anti-PD-1 antibody described herein) is administered at a first dose of about 500 mg once every 3 weeks for 3, 4, or 5 cycles followed by a second dose of about 1000 mg once every 6 weeks or more (e.g., a second dose of about 1000 mg once every 6 weeks). In embodiments, a PD-1 inhibitor (e.g., any anti-PD-1 antibody described herein) is administered at a first dose of about 500 mg once every 3 weeks for 3 cycles followed by a second dose of about 1000 mg once every 6 weeks or more (e.g., a second dose of about 1000 mg once every 6 weeks). In embodiments, a PD-1 inhibitor (e.g., any anti-PD-1 antibody described herein) is administered at a first dose of about 500 mg once every 3 weeks for 4 cycles followed by a second dose of about 1000 mg once every 6 weeks or more (e.g., a second dose of about 1000 mg once every 6 weeks). In embodiments, a PD-1 inhibitor (e.g., any anti-PD-1 antibody described herein) is administered at a first dose of about 500 mg once every 3 weeks for 5 cycles followed by a second dose of about 1000 mg once every 6 weeks or more (e.g., a second dose of about 1000 mg once every 6 weeks).

In some embodiments, administration of a dose may be achieved by administration of a single unit dose composition (i.e., of a single composition that comprises and/or delivers the relevant dose amount). In some embodiments, administration of a dose may be achieved by administration of a plurality of single unit dose compositions. In some embodiments, administration of a dose may be achieved by administration of a portion of a single unit dose composition.

In some embodiments, a PD-1-binding agent (e.g., an anti-PD-1 antibody) is administered according to a regimen that delivers a first dose of PD-1-binding agent once every three weeks for the first 2-6 dosing cycles (e.g., the first 3, 4, or 5 dosing cycles), and then delivers a second dose of a PD-1-binding agent once every six weeks until disease progression. In some embodiments, a PD-1-binding agent (e.g., an anti-PD-1 antibody) is administered according to a regimen that delivers a first dose of a PD-1-binding agent once every three weeks for the first 3, 4, or 5 dosing cycles, and then delivers a second dose of a PD-1-binding agent once every six weeks or more until disease progression. In some embodiments, a PD-1-binding agent (e.g., an anti-PD-1 antibody) is administered according to a regimen that delivers a first dose of a PD-1-binding agent once every three weeks for the first 3, 4, or 5 dosing cycles, and then delivers a second dose of a PD-1-binding agent once every six weeks or more until disease progression. In some embodiments the first and/or second dose of a PD-1-binding agent (e.g., an anti-PD-1 antibody) is about 100 mg to about 2,000 mg. In some embodiments the first dose and the second dose are the same. In some embodiments, the first dose and the second dose are different.

In some embodiments, a PD-1-binding agent (e.g., an anti-PD-1 antibody) is administered according to a regimen that comprises administering a 500 mg dose every 3 weeks for 3, 4, or 5 doses followed by administering at least one 1,000 mg dose every six weeks after the third, fourth, or fifth 500 mg dose. In some embodiments, a PD-1-binding agent (e.g., an anti-PD-1 antibody) is administered according to a regimen that comprises administering a 500 mg dose every 3 weeks for 3 doses followed by administering at least one 1,000 mg dose every six weeks or more after the third 500 mg dose. In some embodiments, a PD-1-binding agent (e.g., an anti-PD-1 antibody) is administered according to a regimen that comprises administering a 500 mg dose every 3 weeks for 4 doses followed by administering at least one 1,000 mg dose every six weeks or more after the fourth 500 mg dose. In some embodiments, a PD-1-binding agent (e.g., an anti-PD-1 antibody) is administered according to a regimen that comprises administering a 500 mg dose every 3 weeks for 5 doses followed by administering at least one 1,000 mg dose every six weeks or more after the fifth 500 mg dose. In some embodiments, additional 1,000 mg doses are administered every six weeks or more after the first 1000 mg dose until no further clinical benefit is achieved. In some particular embodiments, a PD-1 binding agent (e.g., an anti-PD1 antibody) is administered according to a dosing regimen that includes 500 mg for 4 cycles Q3W followed by 1000 mg Q6W.

In some embodiments, the a PD-1-binding agent (e.g., an anti-PD-1 antibody) is administered according to a regimen that comprises administering a 300 mg dose every 3 weeks for 3, 4, or 5 doses followed by administering at least one 800 mg or 1000 mg dose every six weeks after the third, fourth, or fifth 300 mg dose. In some embodiments, additional 800 mg or 1000 mg doses are administered every six weeks after the first 800 mg or 1000 mg dose until no further clinical benefit is achieved. In some particular embodiments, a PD-1 binding agent (e.g., an anti-PD1 antibody) is administered according to a dosing regimen that includes 300 mg for 4 cycles Q3W followed by 800 mg or 1000 mg Q6W.

In some embodiments, the a PD-1-binding agent (e.g., an anti-PD-1 antibody) is administered according to a regimen that comprises administering a 400 mg dose every 3 weeks for 3, 4, or 5 doses followed by administering at least one 800 mg or 1000 mg dose every six weeks after the third, fourth, or fifth 400 mg dose. In some embodiments, additional 800 mg or 1000 mg doses are administered every six weeks after the first 800 mg or 1000 mg dose until no further clinical benefit is achieved. In some particular embodiments, a PD-1 binding agent (e.g., an anti-PD1 antibody) is administered according to a dosing regimen that includes 400 mg for 4 cycles Q3W followed by 800 mg or 1000 mg Q6W.

In some embodiments, the a PD-1-binding agent (e.g., an anti-PD-1 antibody) is administered according to a regimen that comprises administering a 600 mg dose every 3 weeks for 3, 4, or 5 doses followed by administering at least one 800 mg or 1000 mg dose every six weeks after the third, fourth, or fifth 600 mg dose. In some embodiments, additional 800 mg or 1000 mg doses are administered every six weeks after the first 800 mg or 1000 mg dose until no further clinical benefit is achieved. In some particular embodiments, a PD-1 binding agent (e.g., an anti-PD1 antibody) is administered according to a dosing regimen that includes 600 mg for 4 cycles Q3W followed by 800 mg or 1000 mg Q6W.

In some embodiments, a PD-1-binding agent (e.g., an anti-PD-1 antibody) is administered according to a regimen that is demonstrated to achieve an average $C_{max}$ of PD-1-binding agent in a patient population that is within 10 µg/mL to 500 µg/mL. In some embodiments, the regimen is demonstrated to achieve an average $C_{max}$ of PD-1-binding agent in a patient population that is about 20 µg/mL, about 65 µg/mL, or about 200 µg/mL. In some embodiments, the regimen is demonstrated to achieve an average $C_{max}$ of PD-1-binding agent in a patient population that is about 140 µg/mL, about 180 µg/mL, about 200 µg/mL, about 230 µg/mL, about 290 µg/mL. In embodiments, the administration of the anti-PD-1 antibody results in an average $C_{max}$ within 10 µg/mL to 500 µg/mL in the patient (e.g., an average $C_{max}$ of about 20 µg/mL, about 65 µg/mL, or about 200 µg/mL in the patient).

In some embodiments, a PD-1-binding agent (e.g., an anti-PD-1 antibody) is administered according to a regimen that is demonstrated to achieve an average $AUC_{0-336\,h}$ of PD-1-binding agent concentration-time curve in a patient population that is within 2500 h*µg/mL to 50000 h*µg/mL. In some embodiments, the regimen is demonstrated to achieve an average $AUC_{0-336\,h}$ of PD-1-binding agent concentration-time curve in a patient population that is about 3400 h*µg/mL, about 11000 h*µg/mL, or about 36800 h*µg/mL. In embodiments, the administration of the anti-PD-1 antibody results in an average $AUC_{0-336\,h}$ within 2500 h*µg/mL to 50000 h*µg/mL in the patient (e.g., an average $AUC_{0-336\,h}$ is about 3400 h*µg/mL, about 11000 h*µg/mL, or about 36800 h*µg/mL).

In some embodiments, a PD-1-binding agent (e.g., an anti-PD-1 antibody) is administered according to a regimen that is demonstrated to achieve a peak serum concentration of a PD-1-binding agent within 0.5-3 hours after administration.

In some embodiments, a PD-1 binding agent has a terminal half-life of approximately 6, 7, 8, 9, 10, 11, 12, 13, 14, 15, 16, 17, or 18 days. In some embodiments, a PD-1 binding agent has a terminal half-life of approximately 12 days.

In some embodiments, a PD-1-binding agent (e.g., an anti-PD-1 antibody) is administered intravenously. In some embodiments, a PD-1-binding agent (e.g., an anti-PD-1 antibody) is administered by intravenous infusion.

In some embodiments, a PD-1-binding agent (e.g., an anti-PD-1 antibody) is aseptically filled into a clear glass vial. In some embodiments, the glass vial is stoppered with a chlorobutyl elastomer stopper laminated with fluoropolymer and sealed with an aluminum overseal. In some embodiments, a PD-1-binding agent (e.g., an anti-PD-1 antibody) is stored at 2-8° C. In some embodiments, a PD-1-binding agent (e.g., an anti-PD-1 antibody) is free of preservatives.

In some embodiments, the patient is receiving or will receive an additional therapy in combination with the PD-1-binding agent. In some embodiments, the additional therapy is surgery, radiotherapy, chemotherapy or immunotherapy. In some embodiments, the additional therapy includes treatment with a composition that delivers a LAG-3-binding agent (e.g., any described in WO 2016/126858, WO 2017/019894, or WO 2015/138920, each of which is hereby incorporated by reference in its entirety) and/or a TIM-3 binding agent (e.g., any described in WO 2016/161270). In embodiments, an anti-TIM-3 therapy (e.g., an anti-TIM-3 antibody) can be administered at about 1, 3 or 10 mg/kg; a flat dose between about 100-1500 mg; a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; a flat dose about 1500 mg; about 1 mg/kg; about 3 mg/kg; or about 10 mg/kg. In some embodiments, the additional therapy is a PARP inhibitor. In some embodiments, the PARP inhibitor is niraparib, olaparib, rucaparib, talazoparib, and veliparib.

In some embodiments, the present disclosure provides a method of administering a PD-1-binding agent in combination with niraparib to a patient having a recurrent and/or platinum sensitive cancer. In some embodiments, a recurrent and/or platinum sensitive cancer is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, a recurrent and/or platinum sensitive cancer is an anal cancer, a fallopian tube cancer, an ovarian cancer, or a lung cancer. In some certain embodiments, a recurrent and/or platinum sensitive cancer is an endometrial cancer, triple negative breast cancer, ovarian cancer, non-small cell lung cancer (NSCLC), squamous cell carcinoma of the lung or squamous cell carcinoma of the anogenital region (e.g., squamous cell carcinoma of the anus, penis, cervix, vagina, or vulva).

In some embodiments, niraparib is administered to a patient at a dose of 5 mg to 500 mg. In some embodiments, niraparib is administered according to a regimen that comprises a once daily dose of 50 mg to 500 mg of niraparib. In some embodiments, a once daily dose of niraparib comprises 100 mg to 300 mg. In some embodiments, a once daily dose of niraparib comprises 100 mg, 200 mg, or 300 mg. In some embodiments, a once daily dose of niraparib is administered orally.

In some embodiments, the method further comprises a step of reducing the therapeutically effective dose of the anti-PD-1 antibody and/or prolonging the administration interval after achieving the clinical benefit.

The present disclosure provides, in some embodiments, methods of treating cancer comprising administering to a patient in need of treatment an anti-programmed death-1 protein (PD-1) antibody at a first dose at a first interval for a first period; administering to the patient the anti-PD-1 antibody at a second dose at a second interval for a second period; wherein the anti-PD-1 antibody comprises a heavy chain variable region comprising CDR sequences of SEQ ID NOs: 9, 10, and 11 and a light chain variable region comprising CDR sequences of SEQ ID NOs: 12, 13, and 14. In some embodiments, the first dose and the second dose are different. In some embodiments, the first dose is 500 mg and the second dose is 1000 mg. In embodiments, the first interval and the second interval are different. In embodiments, the first interval is once every three weeks and the second interval is once every six weeks. In embodiments, the anti-PD-1 antibody is administered at the first dose once every three weeks for the first period of 2-6 dosing cycles (e.g., the first 3, 4, or 5 dosing cycles), and at the second dose once every six weeks until disease progression.

The present disclosure provides, in some embodiments, compositions comprising a PD-1-binding agent for use in treatment of cancer in a selected cancer patient population, wherein the composition is administered according to a regimen demonstrated to achieve a clinical benefit. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

In some embodiments, a clinical benefit is a complete response ("CR"), a partial response ("PR") or a stable disease ("SD"). In some embodiments, a clinical benefit corresponds to at least SD. In some embodiments, a clinical benefit corresponds to at least a PR. In some embodiments, a clinical benefit corresponds to a CR. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, at least 5% of patients in a patient population achieve a clinical benefit. In some embodiments, at least 5% of patients in a patient population achieve SD. In some embodiments, at least 5% of patients in a patient population achieve at least a PR. In some embodiments, at least 5% of patients achieve in a patient population CR. In some embodiments, at least 20% of patients in a patient population achieve a clinical benefit. In some embodiments, at least 20% of patients in a patient population achieve SD.

In some embodiments, the clinical benefit (e.g., SD, PR and/or CR) is determined in accordance with Response Evaluation Criteria in Solid Tumors (RECIST). In some embodiments, the clinical benefit (e.g., SD, PR and/or CR) is determined in accordance RECIST guidelines. In some embodiments, the clinical benefit (e.g., SD, PR and/or CR) is determined in accordance RECIST guidelines (version 1.1). In some embodiments, the clinical benefit (e.g., SD, PR and/or CR) is determined in accordance immune-related RECIST (irRECIST) guidelines.

The present disclosure provides, in some embodiments, compositions comprising a PD-1-binding agent for use in treatment of cancer in a selected cancer patient population, wherein the composition is administered according to a regimen demonstrated to achieve an average PD-1 receptor occupancy of at least 50% to 85% within 1 to 5 days of administration of a single dose of the PD-1 binding agent. In some embodiments, a PD-1-binding agent comprises a heavy chain variable region with one, two or three CDR sequences selected from SEQ ID NOs: 9, 10, and 11 and/or a light chain variable region with one, two or three CDR sequences selected from SEQ ID NOs: 12, 13, and 14. In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, compositions comprising a PD-1-binding agent for use in treatment of cancer in a selected cancer patient population, wherein the composition is administered according to a regimen demonstrated to achieve an average PD-1 receptor occupancy of at least 75% over the first period of time (e.g., about 15 days to about 60 days; in some embodiments about 29 days). In some embodiments, a PD-1-binding agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, a PD-1-binding agent comprises an immunoglobulin heavy chain whose amino acid sequence comprises SEQ ID NO: 3 and an immunoglobulin light chain whose amino acid sequence comprises SEQ ID NO: 4.

In some embodiments, the patients in the cancer patient population each have a tumor. In some embodiments, the patients in the cancer patient population each have a solid tumor. In some embodiments, at least some of the patients in the cancer patient population have an advanced stage solid tumor. In some embodiments, at least some of the patients in the cancer patient population have a metastatic solid tumor. In some embodiments, the patient has a MSI-H solid tumor.

In some embodiments, the patients in the cancer patient population each have a cancer such as a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, the patients in the cancer patient population each have a cancer such as an anal cancer, a fallopian tube cancer, an ovarian cancer, or a lung cancer. In some embodiments, the patients in the cancer patient population each have a cancer with microsatellite instability (e.g., MSI-H status). In some embodiments, the microsatellite instability is MSI-Low. In some embodiments, the microsatellite instability is microsatellite stable (e.g., MSS status). In some embodiments, the patients in the cancer patient population each have endometrial cancer. In some embodiments, at least some of the patients in the cancer patient population have an endometrial cancer with microsatellite instability or an endometrial cancer that is microsatellite stable (MSS).

In some embodiments, the patients in the cancer patient population each have a hematological cancer. In some embodiments, the patients in the cancer patient population each have a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In some embodiments, the patients in the cancer patient population each have a hematological cancer with microsatellite instability.

In some embodiments, at least some of the patients in the cancer patient population have previously been treated with one or more different cancer treatment modalities. In some embodiments, at least some of the patients in the cancer patient population have previously been treated with one or more of surgery, radiotherapy, chemotherapy or immunotherapy. In some embodiments, at least some of the patients in the cancer patient population have previously been treated with chemotherapy (e.g., platinum-based chemotherapy).

In some embodiments, at least some of the patients in the cancer patient population have not previously been treated with one or more different cancer treatment modalities.

BRIEF DESCRIPTION OF THE DRAWING

The Drawing included herein, which is composed of the following Figures, is for illustration purposes only not for limitation.

DETAILED DESCRIPTION OF CERTAIN EMBODIMENTS

Definitions

Figure 1:
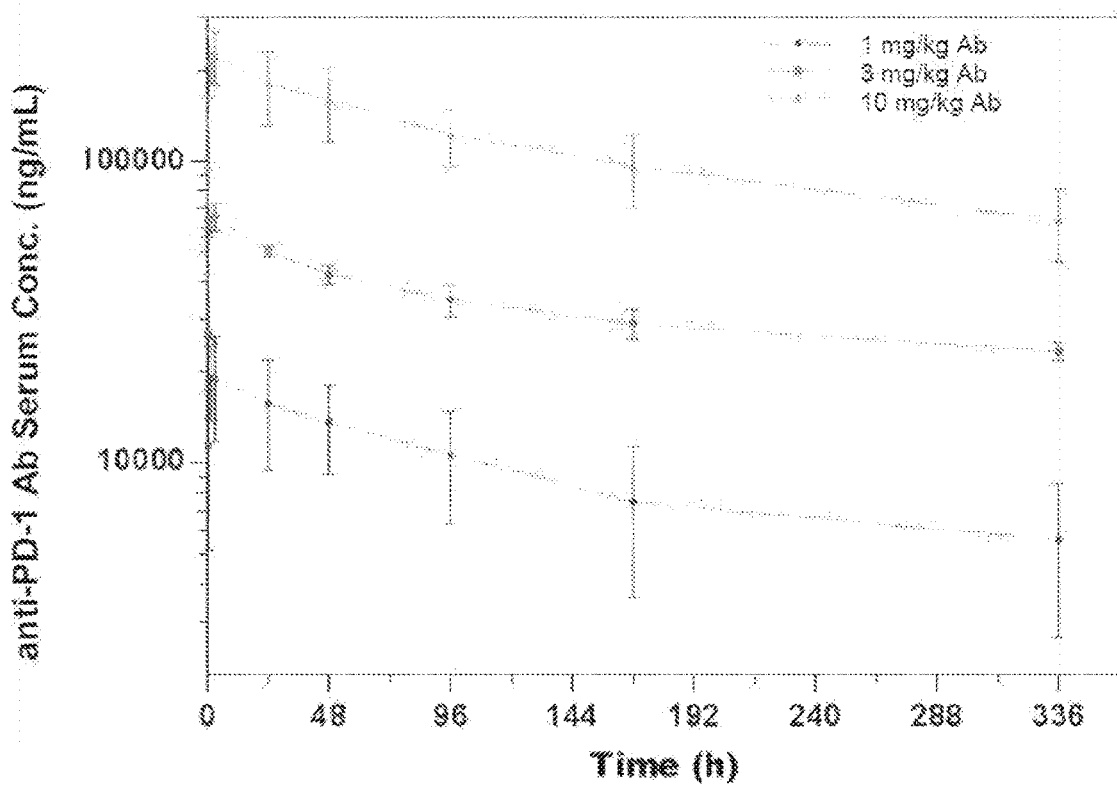
FIG. 1 depicts a graphical representation of log-linear mean concentration versus time profile following a single dose administration of an anti-PD-1 antibody. Dots represent a dose of 1 mg/kg, squares represent a dose of 3 mg/kg and triangles represent a dose of 10 mg/kg. The x-axis indicates time from administration (in hours) and the y-axis indicates the serum concentration of the anti-PD-1 antibody in ng/mL. Error bars represent ±standard deviation.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. Examples of routes of administration include parenteral, e.g., intravenous, intradermal, subcutaneous, oral (e.g., inhalation), transdermal (i.e., topical), transmucosal, and rectal administration. For example, in some embodiments, administration may be ocular, oral, parenteral, topical, etc. In embodiments, administration is parenteral (e.g., intravenous administration). In embodiments, intravenous administration is intravenous infusion. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; TransBodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.].

Antibodies include antibody fragments. Antibodies also include, but are not limited to, polyclonal monoclonal, chimeric dAb (domain antibody), single chain, $F_{ab}$, $F_{ab'}$, $F_{(ab')2}$ fragments, scFvs, and $F_{ab}$ expression libraries. An antibody may be a whole antibody, or immunoglobulin, or an antibody fragment.

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; TransBodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell). In some embodiments, "binding" refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

Binding Agent: In general, the term "binding agent" is used herein to refer to any entity that binds to a target of interest as described herein. In many embodiments, a binding agent of interest is one that binds specifically with its target in that it discriminates its target from other potential binding partners in a particular interaction context. In general, a binding agent may be or comprise an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding moiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise nucleic acids, such as DNA or RNA.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor (e.g., a metastatic solid tumor or an advanced solid tumor). In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastrointestinal cancers and nervous system cancers, benign lesions such as papillomas, and the like.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components. In some embodiments, the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Combination therapy: As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Complete Response: As used herein, the term "complete response" or "CR" is used to mean the disappearance of all or substantially all target lesions. In some embodiments, CR refers to an about 80%, 85%, 90%, 91%, 92%, 93%, 94%, 95%, 96%, 97%, 98%, 99% or 100% decrease in the sum of the diameters of the target lesions (i.e., loss of lesions), taking as reference the baseline sum diameters. In some embodiments, CR indicates that less than about 10%, 9%, 8%, 7%, 6%, 5%, 4%, 3%, 2%, 1% or less of the total lesion diameter remains after treatment. Exemplary methods for evaluating complete response are identified by RECIST guidelines. See, e.g., E. A. Eisenhauer, et al., "New response evaluation criteria in solid tumors: Revised RECIST guideline (version 1.1.),"*Eur. J. of Cancer,* 45: 228-247 (2009).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or regimen: Those skilled in the art will appreciate that the term "regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen). In some embodiments, a regimen comprises at least one dose, wherein the dose comprises one unit dose of a therapeutic agent (e.g., a PD-1-binding agent). In some embodiments, a regimen comprises at least one dose, wherein the dose comprises two or more unit doses of a therapeutic agent. For example, a dose of 500 mg can be administered as a single 500 mg unit dose or as two 250 mg unit doses. In some embodiments, a regimen is correlated with or result in a desired or beneficial outcome when administered across a relevant population (i.e., is a therapeutic regimen).

Hazard Ratio: As used herein, a "hazard ratio" is the expression of the hazard or chance of events occurring in the treatment arm as a ratio of the events occurring in the control arm. Hazard ratios may be determined by the Cox model, a regression method for survival data, which provides an estimate of the hazard ratio and its confidence interval. The hazard ratio is an estimate of the ratio of the hazard rate in the treated versus the control group. The hazard rate is the probability that if the event in question has not already occurred, it will occur in the next time interval, divided by the length of that interval. An assumption of proportional hazards regression is that the hazard ratio is constant over time.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

$K_D$: as used herein, refers to the dissociation constant of a binding agent (e.g., an antibody or binding component thereof) from a complex with its partner (e.g., the epitope to which the antibody or binding component thereof binds).

$K_{off}$: as used herein, refers to the off rate constant for dissociation of a binding agent (e.g., an antibody or binding component thereof) from a complex with its partner (e.g., the epitope to which the antibody or binding component thereof binds).

$K_{on}$: as used herein, refers to the on rate constant for association of a binding agent (e.g., an antibody or binding component thereof) with its partner (e.g., the epitope to which the antibody or binding component thereof binds).

Niraparib: As used herein, the term "niraparib" includes any of the free base compound ((3 S)-3-[4-{7-(aminocarbonyl)-2H-indazol-2-yl}phenyl]piperidine), a salt form, including pharmaceutically acceptable salts, of (3S)-3-[4-{7-(aminocarbonyl)-2H-indazol-2-yl}phenyl]piperidine (e.g., (3S)-3-[4-{7-(aminocarbonyl)-2H-indazol-2-yl}phenyl]piperidine tosylate), or a solvated or hydrated form thereof (e.g., (3S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3 S)-3-[4-{7-(aminocarbonyl)-2H-indazol-2-yl}phenyl]piperidine.

Patient or Subject: As used herein, the term "patient" or "subject" refers to any organism to which provided compound or compounds described herein are administered in accordance with the present invention e.g., for experimental, diagnostic, prophylactic, and/or therapeutic purposes. Typical subjects include animals. The term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone. In embodiments, animals are e.g., mammals such as mice, rats, rabbits, non-human primates, and humans; insects; worms; etc. In some embodiments, a subject is a human. In some embodiments, a subject may be suffering from, and/or susceptible to a disease, disorder, and/or condition (e.g., cancer). As used herein, a "patient population" or "population of subjects" refers to a plurality of patients or subjects.

Partial Response: As used herein, the term "partial response" ("PR") refers to a decrease in tumor progression in a subject as indicated by a decrease in the sum of the diameters of the target lesions, taking as reference the baseline sum diameters. In some embodiments, PR refers to at least a 30% decrease in the sum of diameters or target lesions, taking as reference the baseline sum diameters. Exemplary methods for evaluating partial response are identified by RECIST guidelines. See e.g., E. A. Eisenhauer, et al., "New response evaluation criteria in solid tumors: Revised RECIST guideline (version 1.1.)," Eur. J. of Cancer, 45: 228-247 (2009).

Pharmaceutical composition: As used herein, the term "pharmaceutical composition" refers to a composition in which an active agent (e.g., a PD-1-binding agent) is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, an active agent (e.g., a PD-1-binding agent) is formulated for parenteral administration.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Progression Free Survival: As used herein, the term "progression free survival" means the time period for which a subject having a disease (e.g., cancer) survives, without a significant worsening of the disease state. Progression free survival may be assessed as a period of time in which there is no progression of tumor growth and/or wherein the disease status of a patient is not determined to be a progressive disease. In some embodiments, progression free survival of a subject having cancer is assessed by evaluating tumor (lesion) size, tumor (lesion) number, and/or metastasis.

Progression or Progressive Disease: The term "progression" of tumor growth or a "progressive disease" ("PD") as used herein in reference to cancer status indicates an increase in the sum of the diameters of the target lesions (tumors). In some embodiments, progression of tumor growth refers to at least a 20% increase in the sum of diameters of target lesions, taking as reference the smallest sum on study (this includes the baseline sum if that is the smallest on study). In some embodiments, in addition to a relative increase of 20%, the sum of diameters of target lesions must also demonstrate an absolute increase of at least 5 mm. An appearance of one or more new lesions may also be factored into the determination of progression of tumor growth. Progression for the purposes of determining progression free survival may also be determined if at least one of the following criteria is met: 1) tumor assessment by CT/MRI unequivocally shows progressive disease according to RECIST 1.1 or irRECIST criteria; or 2) additional diagnostic tests (e.g., histology/cytology, ultrasound techniques, endoscopy, positron emission tomography) identify new lesions or determine existing lesions qualify for unequivocal progressive disease AND CA-125-progression according to Gynecologic Cancer Intergroup (GCIG)-criteria (see Rustin et al., Int J Gynecol Cancer 2011; 21: 419-423 which is incorporated herein in its entirety); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion) AND CA-125-progression according to GCIG-criteria.

Solid Tumor: As used herein, the term "solid tumor" refers to an abnormal mass of tissue that usually does not contain cysts or liquid areas. In some embodiments, a solid tumor may be benign; in some embodiments, a solid tumor may be malignant. Those skilled in the art will appreciate that different types of solid tumors are typically named for the type of cells that form them. Examples of solid tumors are carcinomas, lymphomas, and sarcomas. In some embodiments, solid tumors may be or comprise adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stabilization or Stable Disease: As used herein, "stabilization" of tumor growth or a "stable disease" ("SD") refers to neither sufficient shrinkage to qualify for PR nor sufficient increase to qualify for PD. In some embodiments, stabilization refers to a less than 30%, 25%, 20%, 15%, 10% or 5% change (increase or decrease) in the sum of the diameters of the target lesions, taking as reference the baseline sum diameters. Exemplary methods for evaluating stabilization of tumor growth or a stable disease are identified by RECIST guidelines. See e.g., E. A. Eisenhauer, et al., "New response evaluation criteria in solid tumors: Revised RECIST guideline (version 1.1.)," Eur. J. of Cancer, 45: 228-247 (2009).

Therapeutically Effective Amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Methods of Treatment, Including Methods of Treating Cancer

Described herein are methods of treating disorders in a subject (e.g., disorders that benefit from administration of an anti-PD-1 therapy). For example, an anti-PD-1 therapy described herein can agent is administered e.g., as a monotherapy or in combination therapy, for a period sufficient to achieve clinical benefit or according to a regimen as determined by a physician (e.g., an anti-PD-1 therapy is administered in dosage amounts and number of treatment cycles as determined by a physician).

In embodiments, methods described herein are useful for treating T-cell dysfunctional disorders (e.g., cancer). In embodiments, methods described herein are useful for reducing tumors or inhibiting the growth of tumor cells in a subject.

In embodiments, methods described herein are useful for increasing T cell activation or T cell effector function in a subject.

In embodiments, methods described herein are useful for inducing an immune response in a subject.

In embodiments, methods described herein are useful for enhancing an immune response or increasing the activity of an immune cell in a subject.

The inventive methods can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)). When the inventive method treats an infectious disease, an anti-TIM-3 antibody agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

The inventive methods can be used to treat any type of autoimmune disease (i.e., as disease or disorder caused by immune system over-activity in which the body attacks and damages its own tissues), such as those described in, for example, MacKay I. R. and Rose N. R., eds., *The Autoimmune Diseases, Fifth Edition*, Academic Press, Waltham, Mass. (2014). Examples of autoimmune diseases that can be treated by the inventive method include, but are not limited to, multiple sclerosis, type 1 diabetes mellitus, rheumatoid arthritis, scleroderma, Crohn's disease, psoriasis, systemic lupus erythematosus (SLE), and ulcerative colitis. When the inventive method treats an autoimmune disease, an anti-TIM-3 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

PD-1 is abnormally expressed in a variety of cancers (see, e.g., Brown et al, J. Immunol., 170: 1257-1266 (2003); and Flies et. al, Yale Journal of Biology and Medicine, 84: 409-421 (2011)), and PD-L1 expression in some renal cell carcinoma patients correlates with tumor aggressiveness. The inventive methods can be used to treat any type of cancer known in the art.

In embodiments, a cancer that is adenocarcinoma, adenocarcinoma of the lung, acute myeloid leukemia ("AML"), acute lymphoblastic leukemia ("ALL"), adrenocortical carcinoma, anal cancer, appendiceal cancer, B-cell derived leukemia, B-cell derived lymphoma, bladder cancer, brain cancer, breast cancer (e.g., triple negative breast cancer (TNBC)), cancer of the fallopian tube(s), cancer of the testes, cerebral cancer, cervical cancer, choriocarcinoma, chronic myelogenous leukemia, a CNS tumor, colon adenocarcinoma, colon cancer, colorectal cancer, diffuse intrinsic pontine glioma (DIPG), diffuse large B cell lymphoma ("DLBCL"), embryonal rhabdomyosarcoma (ERMS), endometrial cancer, epithelial cancer, esophageal cancer, Ewing's sarcoma, follicular lymphoma ("FL"), gall bladder cancer, gastric cancer, gastrointestinal cancer, glioma, head and neck cancer, a hematological cancer, hepatocellular cancer, Hodgkin's lymphoma/primary mediastinal B-cell lymphoma, kidney cancer, kidney clear cell cancer, laryngeal cancer, leukemia, liver cancer, lung cancer, lymphoma, melanoma, Merkel cell carcinoma, mesothelioma, monocytic leukemia, multiple myeloma, myeloma, a neuroblastic-derived CNS tumor, non-Hodgkin's lymphoma (NHL), non-small cell lung cancer (NSCLC), oral cancer, osteosarcoma, ovarian cancer, ovarian carcinoma, pancreatic cancer, peritoneal cancer, primary peritoneal cancer, prostate cancer, relapsed or refractory classic Hodgkin's Lymphoma (cHL), renal cell carcinoma, rectal cancer, salivary gland cancer (e.g., a salivary gland tumor), sarcoma, skin cancer, small cell lung cancer, small intestine cancer, squamous cell carcinoma of the anogenital region (e.g., squamous cell carcinoma of the anus, penis, cervix, vagina, or vulva), squamous cell carcinoma of the esophagus, squamous cell carcinoma of the head and neck (SCHNC), squamous cell carcinoma of the lung, stomach cancer, T-cell derived leukemia, T-cell derived lymphoma, thymic cancer, a thymoma, thyroid cancer, uveal melanoma, urothelial cell carcinoma, uterine cancer, uterine endometrial cancer, uterine sarcoma, vaginal cancer, vulvar cancer, or Wilms tumor.

In other embodiments, a cancer is a head and neck cancer, a lung cancer (e.g., a non-small cell lung cancer (NSCLC)), a renal cancer, a bladder cancer, a melanoma, Merkel cell carcinoma (see, e.g., Bhatia et al., Curr. Oncol. Rep., 13(6): 488-497 (2011), a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some embodiments, a cancer for treatment in the context of the present disclosure is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

In some embodiments, a patient or population of patients have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In embodiments, a cancer is a blood-borne cancer such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, and myelocytic leukemias.

In embodiments a cancer is a lymphoma such as Hodgkin's disease, non-Hodgkin's Lymphoma, Multiple myeloma, Waldenstrom's macroglobulinemia, Heavy chain disease and Polycythemia vera.

In embodiments, a cancer is a squamous cell carcinoma. In embodiments, a cancer is squamous cell carcinoma of the lung. In embodiments, a cancer is squamous cell carcinoma of the esophagus. In embodiments, a cancer is head and neck squamous cell carcinoma (HNSCC).

In embodiments, a cancer is squamous cell carcinoma of the anogenital region (e.g., of the anus, penis, cervix, vagina, or vulva).

In embodiments, a cancer is bladder cancer, breast cancer (e.g., triple negative breast cancer (TNBC)), cancer of the fallopian tube(s), cholagiocarcinoma, colon adenocarcinoma, endometrial cancer, esophageal cancer, Ewing's sarcoma, gastric cancer, kidney clear cell cancer, lung cancer (e.g., lung adenocarcinoma or lung squamous cell cancer), mesothelioma, ovarian cancer, pancreatic cancer, peritoneal cancer, prostate cancer, uterine endometrial cancer, or uveal melanoma. In embodiments, a cancer is ovarian cancer, cancer of the fallopian tube(s), or peritoneal cancer. In embodiments, a cancer is breast cancer (e.g., TNBC). In embodiments, a cancer is lung cancer (e.g., non-small cell lung cancer). In embodiments, a cancer is prostate cancer.

In embodiments, a cancer is a CNS or brain cancer such as neuroblastoma (NB), glioma, diffuse intrinsic pontine glioma (DIPG), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor, or medulloblastoma. In embodiments, a cancer is a CNS tumor.

In some embodiments, a patient or population of patients have a solid tumor. In embodiments, a cancer is a solid tumor such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, osteosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, non small cell lung cancer (NSCLC), small cell lung carcinoma, bladder carcinoma, lung cancer, epithelial carcinoma, skin cancer, melanoma, neuroblastoma (NB), or retinoblastoma. In some embodiments, the tumor is an advanced stage solid tumor. In some embodiments, the tumor is a metastatic solid tumor. In some embodiments, the patient has a MSI-H solid tumor.

In some embodiments, a patient or population of patients to be treated by the methods of the present invention have or are susceptible to cancer, such as a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some embodiments, a patient or population of patients to be treated by the methods of the present invention have or are susceptible to lung cancer (e.g., NSCLC), renal cancer, melanoma, cervical cancer, colorectal cancer, or endometrial cancer (e.g., MSS endometrial cancer or MSI-H endometrial cancer).

In some embodiments, a cancer is a gynecologic cancer (i.e., a cancer of the female reproductive system such as ovarian cancer, fallopian tube cancer, cervical cancer, vaginal cancer, vulvar cancer, uterine cancer, or primary peritoneal cancer, or breast cancer). In some embodiments, cancers of the female reproductive system include, but are not limited to, ovarian cancer, cancer of the fallopian tube(s), peritoneal cancer, and breast cancer.

In embodiments, a cancer is ovarian cancer (e.g., serous or clear cell ovarian cancer). In embodiments, a cancer is fallopian tube cancer (e.g., serous or clear cell fallopian tube cancer). In embodiments, a cancer is primary peritoneal cancer (e.g., serous or clear cell primary peritoneal cancer).

In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, call the peritoneum. In some embodiments, the cancer is or comprises a germ cell tumor.

Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis. In some embodiments, a gynecologic cancer is associated with homologous recombination repair deficiency/homologous repair deficiency ("HRD") and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy (e.g., a partial or complete response to the last platinum-based therapy or to the penultimate platinum-based therapy). In some embodiments, a gynecologic cancer is now resistant to platinum-based therapy.

In embodiments, a cancer is a breast cancer. Usually breast cancer either begins in the cells of the milk producing glands, known as the lobules, or in the ducts. Less commonly breast cancer can begin in the stromal tissues. These include the fatty and fibrous connective tissues of the breast. Over time the breast cancer cells can invade nearby tissues such the underarm lymph nodes or the lungs in a process known as metastasis. The stage of a breast cancer, the size of the tumor and its rate of growth are all factors which determine the type of treatment that is offered. Treatment options include surgery to remove the tumor, drug treatment which includes chemotherapy and hormonal therapy, radiation therapy and immunotherapy. The prognosis and survival rate varies widely; the five year relative survival rates vary from 98% to 23% depending on the type of breast cancer that occurs. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2. In some embodiments, triple negative breast cancer (TNBC) is characterized as breast cancer cells that are estrogen receptor expression negative (<1% of cells), progesterone receptor expression negative (<1% of cells), and HER2-negative.

In embodiments, a cancer is ER-positive breast cancer, ER-negative breast cancer, PR-positive breast cancer, PR-negative breast cancer, HER2-positive breast cancer, HER2-negative breast cancer, BRCA1/2-positive breast cancer, BRCA1/2-negative cancer, or triple negative breast cancer (TNBC). In embodiments, a cancer is triple negative breast cancer (TNBC).

In some embodiments, a breast cancer is a metastatic breast cancer. In some embodiments, a breast cancer is an advanced breast cancer. In some embodiments, a cancer is a stage II, stage III or stage IV breast cancer. In some embodiments, a cancer is a stage IV breast cancer. In some embodiments, a breast cancer is a triple negative breast cancer.

In some embodiments, a patient or a population of patients to be treated by the methods of the present disclosure have or are susceptible to endometrial cancer ("EC"). Endometrial carcinoma is the most common cancer of the female genital, tract accounting for 10-20 per 100,000 person-years. The annual number of new cases of endometrial cancer (EC) is estimated at about 325 thousand worldwide. Further, EC is the most commonly occurring cancer in post-menopausal women. About 53% of endometrial cancer cases occur in developed countries. In 2015, approximately 55,000 cases of EC were diagnosed in the U.S. and no targeted therapies are currently approved for use in EC. There is a need for agents and regimens that improve survival for advanced and recurrent EC in 1 L and 2 L settings. Approximately 10,170 people are predicted to die from EC in the U.S. in 2016. The most common histologic form is endometrioid adenocarcinoma, representing about 75-80% of diagnosed cases. Other histologic forms include uterine papillary serous (less than 10%), clear cell 4%, mucinous 1%, squamous less than 1% and mixed about 10%.

From the pathogenetic point of view, EC falls into two different types, so-called types I and II. Type I tumors are low-grade and estrogen-related endometrioid carcinomas (EEC) while type II are non-endometrioid (NEEC) (mainly serous and clear cell) carcinomas. The World Health Organization has recently updated the pathologic classification of EC, recognizing nine different subtypes of EC, but EEC and serous carcinoma (SC) account for the vast majority of cases. EECs are estrogen-related carcinomas, which occur in perimenopausal patients, and are preceded by precursor lesions (endometrial hyperplasia/endometrioid intraepithelial neoplasia). Microscopically, lowgrade EEC (EEC 1-2) contains tubular glands, somewhat resembling the proliferative endometrium, with architectural complexity with fusion of the glands and cribriform pattern. High-grade EEC shows solid pattern of growth. In contrast, SC occurs in postmenopausal patients in absence of hyperestrogenism. At the microscope, SC shows thick, fibrotic or edematous papillae with prominent stratification of tumor cells, cellular budding, and anaplastic cells with large, eosinophilic cytoplasms. The vast majority of EEC are low grade tumors (grades 1 and 2), and are associated with good prognosis when they are restricted to the uterus. Grade 3 EEC (EEC3) is an aggressive tumor, with increased frequency of lymph node metastasis. SCs are very aggressive, unrelated to estrogen stimulation, mainly occurring in older women. EEC 3 and SC are considered high-grade tumors. SC and EEC3 have been compared using the surveillance, epidemiology and End Results (SEER) program data from 1988 to 2001. They represented 10% and 15% of EC respectively, but accounted for 39% and 27% of cancer death respectively.

Endometrial cancers can also be classified into four molecular subgroups: (1) ultramutated/POLE-mutant; (2) hypermutated MSI+ (e.g., MSI-H or MSI-L); (3) copy number low/microsatellite stable (MSS); and (4) copy number high/serous-like. Approximately 28% of cases are MSI-high. (Murali, Lancet Oncol. (2014). In some embodiments, a patient has a mismatch repair deficient subset of 2 L endometrial cancer.

In embodiments, an endometrial cancer is metastatic endometrial cancer.

In embodiments, a patient has a MSS endometrial cancer.

In embodiments, a patient has a MSI-H endometrial cancer.

In embodiments, a cancer is a lung cancer. In embodiments, a lung cancer is a squamous cell carcinoma of the lung. In embodiments, a lung cancer is small cell lung cancer (SCLC). In embodiments, a lung cancer is non-small cell lung cancer (NSCLC) such as squamous NSCLC. In embodiments, a lung cancer is an ALK-translocated lung cancer (e.g., ALK-translocated NSCLC). In embodiments, a lung cancer is an EGFR-mutant lung cancer (e.g., EGFR-mutant NSCLC).

In embodiments, a cancer is a colorectal (CRC) cancer (e.g., a solid tumor). In embodiments, a colorectal cancer is an advanced colorectal cancer. In embodiments, a colorectal cancer is a metastatic colorectal cancer. In embodiments, a colorectal cancer is a MSI-H colorectal cancer. In embodiments, a colorectal cancer is a MSS colorectal cancer. In embodiments, a colorectal cancer is a POLE-mutant colorectal cancer. In embodiments, a colorectal cancer is a POLD-mutant colorectal cancer. In embodiments, a colorectal cancer is a high TMB colorectal cancer.

In embodiments, a cancer is a melanoma. In embodiments, a melanoma is an advanced melanoma. In embodiments, a melanoma is a metastatic melanoma. In embodiments, a melanoma is a MSI-H melanoma. In embodiments, a melanoma is a MSS melanoma. In embodiments, a melanoma is a POLE-mutant melanoma. In embodiments, a melanoma is a POLD-mutant melanoma. In embodiments, a melanoma is a high TMB melanoma.

In embodiments, a cancer is an advanced cancer.

In embodiments, a cancer is a metastatic cancer.

In embodiments, a cancer is a recurrent cancer (e.g., a recurrent gynecological cancer such as recurrent epithelial ovarian cancer, recurrent fallopian tube cancer, recurrent primary peritoneal cancer, or recurrent endometrial cancer).

Cancers that can be treated with methods described herein include cancers associated with a high tumor mutation burden (TMB), cancers that microsatellite stable (MSS), cancers that are characterized by microsatellite instability, cancers that have a high microsatellite instability status (MSI-H), cancers that have low microsatellite instability status (MSI-L), cancers associated with high TMB and MSI-H (e.g., cancers associated with high TMB and MSI-L or MSS), cancers having a defective DNA mismatch repair system, cancers having a defect in a DNA mismatch repair gene, hypermutated cancers, cancers having homologous recombination repair deficiency/homologous repair deficiency ("HRD"), cancers comprising a mutation in polymerase delta (POLD), and cancers comprising a mutation in polymerase epsilon (POLE).

In some embodiments, a tumor to be treated is characterized by microsatellite instability. In some embodiments, a tumor is characterized by microsatellite instability high status (MSI-H). Microsatellite instability ("MSI") is or comprises a change that in the DNA of certain cells (such as tumor cells) in which the number of repeats of microsatellites (short, repeated sequences of DNA) is different than the number of repeats that was contained in the DNA from which it was inherited. About 15% of sporadic colorectal cancers (CRC) harbor widespread alterations in the length of microsatellite (MS) sequences, known as microsatellite instability (MSI) (Boland and Goel, 2010). Sporadic MSI CRC tumors display unique clinicopathological features including near-diploid karyotype, higher frequency in older populations and in females, and a better prognosis (de la Chapelle and Hampel, 2010; Popat et al., 2005). MSI is also present in other tumors, such as in endometrial cancer (EC) of the uterus, the most common gynecological malignancy (Duggan et al., 1994). The same reference Bethesda panel originally developed to screen an inherited genetic disorder (Lynch syndrome) (Umar et al., 2004) is currently applied to test MSI for CRCs and ECs. However, the genes frequently targeted by MSI in CRC genomes rarely harbor DNA slippage events in EC genomes (Gurin et al., 1999).

Microsatellite instability arises from a failure to repair replication-associated errors due to a defective DNA mismatch repair (MMR) system. This failure allows persistence of mismatch mutations all over the genome, but especially in regions of repetitive DNA known as microsatellites, leading to increased mutational load. It has been demonstrated that at least some tumors characterized by MSI-H have improved responses to certain anti-PD-1 agents (Le et al., (2015) *N Engl. J. Med.* 372(26):2509-2520; Westdorp et al., (2016) *Cancer Immunol. Immunother.* 65(10):1249-1259). In some embodiments, a cancer has a microsatellite instability of high microsatellite instability (e.g., MSI-H status). In some embodiments, a cancer has a microsatellite instability status of low microsatellite instability (e.g., MSI-Low).

In some embodiments, a cancer has a microsatellite instability status of microsatellite stable (e.g., MSS status). In some embodiments microsatellite instability status is assessed by a next generation sequencing (NGS)-based assay, an immunohistochemistry (IHC)-based assay, and/or a PCR-based assay. In some embodiments, microsatellite instability is detected by NGS. In some embodiments, microsatellite instability is detected by IHC. In some embodiments, microsatellite instability is detected by PCR.

In embodiments, a patient has a MSI-L cancer.

In embodiments, a patient has a MSI-H cancer. In some embodiments, a patient has a MSI-H solid tumor. In embodiments, a MSI-H cancer is MSI-H endometrial cancer. In embodiments, a MSI-H cancer is a solid tumor. In embodiments, a MSI-H cancer is a metastatic tumor. In embodiments, a MSI-H cancer is endometrial cancer. In embodiments, a MSI-H cancer is a non-endometrial cancer. In embodiments, a MSI-H cancer is colorectal cancer.

In embodiments, a patient has a MSS cancer. In embodiments, a MSS cancer is MSS endometrial cancer.

In embodiments, a cancer is associated with a POLE (DNA polymerase epsilon) mutation (i.e., a cancer is a POLE-mutant cancer). In embodiments, a POLE mutation is a mutation in the exonuclease domain. In embodiments, a POLE mutation is a germline mutation. In embodiments, a POLE mutation is a sporadic mutation. In embodiments, a MSI cancer also is associated with a POLE mutation. In embodiments, a MSS cancer also is associated with a POLE mutation. In embodiments, a POLE mutation is identified using sequencing. In embodiments, a POLE-mutant cancer is endometrial cancer. In embodiments, a POLE-mutant cancer is colon cancer. In embodiments, a POLE-mutant cancer is pancreatic cancer, ovarian cancer, or cancer of the small intestine.

In embodiments, a cancer is associated with a POLD (DNA polymerase delta) mutation (i.e., a cancer is a POLD-mutant cancer). In embodiments, a POLD mutation is a mutation in the exonuclease domain. In embodiments, a POLD mutation is a somatic mutation. In embodiments, a POLD mutation is a germline mutation. In embodiments, a POLD-mutant cancer is identified using sequencing. In embodiments, a POLD-mutant cancer is endometrial cancer. In embodiments, a POLD-mutant cancer is colorectal cancer. In embodiments, a POLD-mutant cancer is brain cancer.

In some embodiments, a patient has a mismatch repair deficient (MMRd) cancer.

In embodiments, a MMRd cancer is colorectal cancer.

Microsatellite instability may arise from a failure to repair replication-associated errors due to a defective DNA mismatch repair (MMR) system. This failure allows persistence of mismatch mutations all over the genome, but especially in regions of repetitive DNA known as microsatellites, leading to increased mutational load that may improve responses to certain anti-PD-1 agents. Id. In some embodiments MSI-H status is assess by a NGS-based assay and/or a PCR-based MSI assay. In some embodiments, microsatellite instability is detected by next generation sequencing. In embodiments, microsatellite instability is detected using immunohistochemistry (IHC) testing.

In embodiments, a cancer (e.g., a MMRd cancer) is characterized by a high tumor mutation burden (i.e., a cancer is a high TMB cancer). In some embodiments, the cancer is associated with high TMB and MSI-H. In some embodiments, the cancer is associated with high TMB and MSI-L or MSS. In some embodiments, the cancer is endometrial cancer associated with high TMB. In some related embodiments, the endometrial cancer is associated with high TMB and MSI-H. In some related embodiments, the endometrial cancer is associated with high TMB and MSI-L or MSS. In embodiments, a high TMB cancer is colorectal cancer. In embodiments, a high TMB cancer is lung cancer (e.g., small cell lung cancer (SCLC) or non-small cell lung cancer (NSCLC) such as squamous NSCLC or non-squamous NSCLC). In embodiments, a high TMB cancer is melanoma. In embodiments, a high TMB cancer is urothelial cancer.

In embodiments, a patient has a cancer with elevated expression of tumor-infiltrating lymphocytes (TILs), i.e., a patient has a high-TIL cancer. In embodiments, a high-TIL cancer is breast cancer (e.g., triple negative breast cancer (TNBC) or HER2-positive breast cancer). In embodiments, a high-TIL cancer is a metastatic cancer (e.g., a metastatic breast cancer).

In embodiments, immune-related gene expression signatures can be predictive of a response to an anti-PD-1 therapy for cancer as described herein. For example, a gene panel that includes genes associated with IFN-γ signaling can be useful in identifying cancer patients who would benefit from anti-PD-1 therapy. Exemplary gene panels are described in Ayers et al., *J. Clin. Invest.*, 127(8):2930-2940, 2017. In embodiments, a cancer patient has a cancer that is breast cancer (e.g., TNBC) or ovarian cancer. In embodiments, a cancer patient has a cancer that is bladder cancer, gastric cancer, bilary cancer, esophageal cancer, or head and neck squamous cell carcinoma (HNSCC). In embodiments, a cancer patient has a cancer that is anal cancer or colorectal cancer.

In some embodiments, a patient has a tumor that expresses PD-L1. In some embodiments, PD-L1 status is evaluated in a patient or patient population. In some embodiments, mutational load and baseline gene expression profiles in archival or fresh pre-treatment biopsies are evaluated before, during and/or after treatment with an anti-PD-1 antibody agent. In some embodiments, the status and/or expression of TIM-3 and/or LAG-3 are evaluated in patients.

In some embodiments, at least some of the patients in the cancer patient population have not previously been treated with one or more different cancer treatment modalities.

In some embodiments, a patient has previously been treated with one or more different cancer treatment modalities (e.g., one or more of surgery, radiotherapy, chemotherapy or immunotherapy). In embodiments, a subject has previously been treated with two or more different cancer treatment modalities (e.g., one or more of surgery, radiotherapy, chemotherapy, or immunotherapy). In embodiments, a subject has been previously treated with a cytotoxic therapy. In embodiments, a subject has been previously treated with chemotherapy. In embodiments, a subject has previously been treated with two different cancer treatment modalities (e.g., one or more of surgery, radiotherapy, chemotherapy, or immunotherapy). In embodiments, a subject has previously been treated with three different cancer treatment modalities (e.g., one or more of surgery, radiotherapy, chemotherapy, or immunotherapy).

In embodiments of methods described herein, a method further comprises administering one or more of surgery, a radiotherapy, a chemotherapy, an immunotherapy, an anti-angiogenic agent, or an anti-inflammatory. In embodiments, a method further comprises administering a chemotherapy.

In some embodiments, at least some of the patients in the cancer patient population have previously been treated with chemotherapy (e.g., platinum-based chemotherapy). For example, a patient who has received two lines of cancer treatment can be identified as a 2 L cancer patient (e.g., a 2 L NSCLC patient). In embodiments, a patient has received two lines or more lines of cancer treatment (e.g., a 2 L+ cancer patient such as a 2 L+ endometrial cancer patient). In embodiments, a patient has not been previously treated with an anti-PD-1 therapy. In embodiments, a patient previously received at least one line of cancer treatment (e.g., a patient previously received at least one line or at least two lines of cancer treatment). In embodiments, a patient previously received at least one line of treatment for metastatic cancer (e.g., a patient previously received one or two lines of treatment for metastatic cancer).

In embodiments, a subject is resistant to treatment with an agent that inhibits PD-1.

In embodiments, a subject is refractory to treatment with an agent that inhibits PD-1.

In embodiments, a method described herein sensitizes the subject to treatment with an agent that inhibits PD-1.

In embodiments, a subject comprises an exhausted immune cell (e.g., an exhausted immune cell that is an exhausted T cell).

In embodiments of methods described herein, a subject is an animal (e.g., a mammal). In embodiments, a subject is a human. In embodiments, a subject is a non-human mammal (e.g., mice, rats, rabbits, or non-human primates). Accordingly, methods described herein can be useful in both treatment of humans and in veterinary medicine.

In embodiments, a PD-1 inhibitor (e.g., an anti-PD-1 antibody) is administered intravenously (e.g., by intravenous infusion).

Programmed Death 1 (PD-1)

Programmed Death 1 (PD-1) (also known as Programmed Cell Death 1) is a type I transmembrane protein of 268 amino acids originally identified by subtractive hybridization of a mouse T cell line undergoing apoptosis (Ishida et al., *Embo J.*, 11: 3887-95 (1992)). PD-1 is a member of the CD28/CTLA-4 family of T-cell regulators, and is expressed on activated T-cells, B-cells, and myeloid lineage cells (Greenwald et al., *Annu. Rev. Immunol.*, 23: 515-548 (2005); and Sharpe et al., *Nat. Immunol.*, 8: 239-245 (2007)). PD-1 is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) *Curr. Opin. Immunol* 14:391779-82; Bennett et al. (2003) *J Immunol* 170:711-8).

Two ligands for PD-1 have been identified, PD ligand 1 (PD-L1) and PD ligand 2 (PD-L2), both of which belong to the B7 protein superfamily (Greenwald et al, supra). PD-L1 is expressed in a variety of cell types, including cells of the lung, heart, thymus, spleen, and kidney (see, e.g., Freeman et al., *J. Exp. Med.*, 192(7): 1027-1034 (2000); and Yamazaki et al., *J. Immunol.*, 169(10): 5538-5545 (2002)). PD-L1 expression is unregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Natl Acad. Sci. USA*, 99(9): 12293-12297 (2002); and Blank et al., *Cancer Res.*, 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.*, 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 negatively regulates T-cell activation, and this inhibitory function is linked to an immunoreceptor tyrosine-based switch motif (ITSM) in the cytoplasmic domain (see, e.g., Greenwald et al., supra; and Parry et al., *Mol. Cell. Biol.*, 25: 9543-9553 (2005)). PD-1 deficiency can lead to autoimmunity. For example, C57BL/6 PD-1 knockout mice have been shown to develop a lupus-like syndrome (see, e.g., Nishimura et al., *Immunity*, 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens*, 62(6): 492-497 (2003); Bertsias et al., *Arthritis Rheum.*, 60(1): 207-218 (2009); Ni et al, *Hum. Genet.*, 121(2): 223-232 (2007); Tahoori et al., *Clin. Exp. Rheumatol.*, 29(5): 763-767 (2011); and Kroner et al., *Ann. Neurol.*, 58(1): 50-57 (2005)). Abnormal PD-1 expression also has been implicated in T-cell dysfunctions in several pathologies, such as tumor immune evasion and chronic viral infections (see, e.g., Barber et al., *Nature*, 439: 682-687 (2006); and Sharpe et al., supra).

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.*, 8: 793-800 (2002)). Expression of PD-L1 by tumor cells has been directly associated with their resistance to lysis by anti-tumor T-cells in vitro (Dong et al., supra; and Blank et al., *Cancer Res.*, 64: 1140-1145 (2004)). PD-1 knockout mice are resistant to tumor challenge (Iwai et al., *Int. Immunol.*, 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.*, 65: 1089-1096 (2005)), and high levels of PD-L1 expression in tumors are associated with poor prognosis for many human cancer types (Hamanishi et al., *Proc. Natl. Acad. Sci. USA*, 104: 3360-335 (2007), Brown et al, *J. Immunol.*, 170: 1257-1266 (2003); and Flies et al., *Yale Journal of Biology and Medicine*, 84(4): 409-421 (2011)).

In view of the foregoing, strategies for inhibiting PD-1 activity to treat various types of cancer and for immunopotentiation (e.g., to treat infectious diseases) have been developed (see, e.g., Ascierto et al., *Clin. Cancer. Res.*, 19(5): 1009-1020 (2013)). In this respect, monoclonal antibodies targeting PD-1 have been developed for the treatment of cancer (see, e.g., Weber, *Semin. Oncol.*, 37(5): 430-4309 (2010); and Tang et al., *Current Oncology Reports*, 15(2):

98-104 (2013)). For example, nivolumab (also known as BMS-936558) produced complete or partial responses in non-small-cell lung cancer, melanoma, and renal-cell cancer in a Phase I clinical trial (see, e.g., Topalian, *New England. J. Med.,* 366: 2443-2454 (2012)), and is currently in Phase III clinical trials. MK-3575 is a humanized monoclonal antibody directed against PD-1 that has shown evidence of antitumor activity in Phase I clinical trials (see, e.g., Patnaik et al., 2012 *American Society of Clinical Oncology (ASCO) Annual Meeting,* Abstract #2512). In addition, recent evidence suggests that therapies which target PD-1 may enhance immune responses against pathogens, such as HIV (see, e.g., Porichis et al., *Curr. HIV/AIDS Rep.,* 9(1): 81-90 (2012)). Despite these advances, however, the efficacy of these potential therapies in humans may be limited.

PD-1-Binding Agents

The present disclosure provides methods of treating cancer that include administering compositions that deliver particular programmed death-1 protein (PD-1)-binding agents according to regimens that may achieve clinical benefit(s). The present disclosure describes, at least in part, PD-1-binding agents (e.g., anti-PD-1 antibody agents) and various compositions and methods relating thereto. In some embodiments, a PD-1-binding agent (e.g., anti-PD-1 antibody agent) binds an epitope of PD-1 which blocks the binding of PD-1 to any one or more of its putative ligands. In some embodiments, a PD-1-binding agent (e.g., anti-PD-1 antibody agent) binds an epitope of PD-1 which blocks the binding of PD-1 to two or more of its putative ligands. In some embodiments, a PD-1-binding agent (e.g., anti-PD-1 antibody agent) binds an epitope of a PD-1 protein which blocks the binding of PD-1 to PD-L1 and/or PD-L2. PD-1-binding agents (e.g., anti-PD-1 antibody agents) of the present disclosure may comprise a heavy chain constant region (Fc) of any suitable class. In some embodiments, a PD-1-binding agent (e.g., anti-PD-1 antibody agent) comprises a heavy chain constant region that is based upon wild-type IgG1, IgG2, or IgG4 antibodies, or variants thereof. In some embodiments, a PD-1-binding agent is a monoclonal antibody.

In some embodiments, a PD-1-binding agent comprises a heavy chain variable region with one or more CDR sequences selected from SEQ ID NOs: 9, 10, and 11 and/or a light chain variable region with one or more CDR sequences selected from SEQ ID NOs: 12, 13, and 14. In some embodiments, a PD-1-binding agent comprises a heavy chain variable region with two or more CDR sequences selected from SEQ ID NOs: 9, 10, and 11 and/or a light chain variable region with two or more CDR sequences selected from SEQ ID NOs: 12, 13, and 14. In some embodiments, a PD-1-binding agent comprises a heavy chain variable region with three CDRs that have sequences of SEQ ID NOs: 9, 10, and 11 and/or a light chain variable region with three CDRs that have sequences of SEQ ID NOs: 12, 13, and 14.

```
(HCDR1)-
                                        SEQ ID NO: 9
SYDMS (HCDR2)-
                                        SEQ ID NO: 10
TISGGGSYTYYQDSVKG (HCDR3)-
                                        SEQ ID NO: 11
PYYAMDY (LCDR1)-
                                        SEQ ID NO: 12
KASQDVGTAVA (LCDR2)-
                                        SEQ ID NO: 13
WASTLHT (LCDR3)-
                                        SEQ ID NO: 14
QHYSSYPWT
```

In some embodiments, a PD-1-binding agent comprises an immunoglobulin heavy chain variable domain whose amino acid sequence comprises SEQ ID NO: 1 or SEQ ID NO: 7.

```
                                        SEQ ID NO: 1
EVQLLESGGGLVQPGGSLRLSCAASGFTFSSYDMSWVRQAPGKGLEWVST
ISGGGSYTYYQDSVKGRFTISRDNSKNTLYLQMNSLRAEDTAVYYCASPY
YAMDYWGQGTTVTVSSA

SEQ ID NO: 7
EVQLLESGGGLVQPGGSLRLSCAASGFTFSSYDMSWVRQAPGKGLEWVST
ISGGGSYTYYQDSVKGRFTISRDNSKNTLYLQMNSLRAEDTAVYYCASPY
YAMDYWGQGTTVTVSS
```

In some embodiments, a PD-1-binding agent comprises an immunoglobulin light chain variable domain whose amino acid sequence comprises SEQ ID NO: 2 or SEQ ID NO: 8.

```
                                        SEQ ID NO: 2
DIQLTQSPSFLSAYVGDRVTITCKASQDVGTAVAWYQQKPGKAPKLLIYW
ASTLHTGVPSRFSGSGSGTEFTLTISSLQPEDFATYYCQHYSSYPWTFGQ
GTKLEIKR

SEQ ID NO: 8
DIQLTQSPSFLSAYVGDRVTITCKASQDVGTAVAWYQQKPGKAPKLLIYW
ASTLHTGVPSRFSGSGSGTEFTLTISSLQPEDFATYYCQHYSSYPWTFGQ
GTKLEIK
```

In some embodiments, a PD-1-binding agent comprises an immunoglobulin heavy chain variable domain whose amino acid sequence comprises SEQ ID NO: 1 or SEQ ID NO: 7 and/or an immunoglobulin light chain variable domain whose amino acid sequence comprises SEQ ID NO: 2 or SEQ ID NO: 8. In some embodiments a PD-1-binding agent is or comprises an immunoglobulin G4 (IgG4) humanized monoclonal antibody (mAb). In some embodiments, a PD-1-binding agent comprises a human IGHG4*01 polypeptide. In some embodiments, a PD-1-binding agent comprises one or more mutations within the IgG heavy chain region. In some embodiments, a PD-1-binding agent comprises an IgG4 heavy chain constant region having one or more mutations in the heavy chain constant region. In some embodiments, a PD-1-binding agent comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include a serine to proline stabilizing mutation that prevents half molecule exchange with other IgG4 molecules. In some embodiments, the one or more mutations in hinge region of IgG4 may include an S228P mutation. See, e.g., J. Biol. Chem. 2015; 290(9):5462-5469.

In some embodiments, a PD-1-binding agent comprises an immunoglobulin heavy chain polypeptide whose amino acid sequence comprises SEQ ID NO: 3.

-An anti-PD-1 antibody heavy chain polypeptide
(CDR sequences)
SEQ ID NO: 3
EVQLLESGGGLVQPGGSLRLSCAASGFTFS<u>SYDMS</u>WVRQAPGKGKLEWVS<u>T <u>ISGGGSYTYYQDSVKG</u>RFTISRDNSKNTLYLQMNSLRAEDTAVYYCAS<u>PY <u>YAMD</u>YWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

In some embodiments, a PD-1-binding agent comprises an immunoglobulin light chain polypeptide whose amino acid sequence comprises SEQ ID NO: 4.

-An anti-PD-1 antibody light chain polypeptide
(CDR sequences)
SEQ ID NO: 4
DIQLTQSPSFLSAYVGDRVTITC<u>KASQDVGTAVA</u>WYQQKPGKAPKLLIY<u>W <u>ASTLHT</u>GVPSRFSGSGSGTEFTLTISSLQPEDFATYYC<u>QHYSSYPWT</u>FGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NOs: 3 and 4 describe an exemplary humanized monoclonal anti-PD-1 antibody utilizing a human IGHG4*01 heavy chain gene, and a human IGKC*01 kappa light chain gene, as scaffolds. There is a single Ser to Pro point mutation in the hinge region of the IgG4 heavy chain. This mutation is at the canonical S228 position, corresponding to residue 224 in SEQ ID NO: 3. Without wishing to be bound by theory, it is envisioned that this point mutation serves to stabilize the hinge of the antibody heavy chain.

Biophysical and biochemical characterization of this exemplary humanized monoclonal anti-PD-1 antibody is consistent with the expected disulfide linkage pattern for an IgG4 molecule. The residues involved in the expected inter- and intrachain disulfide linkages are tabulated below (Tables 1 and 2).

TABLE 1

Expected residues involved in disulfide linkages of an exemplary anti-PD-1 antibody agent heavy chain having an amino acid sequence as set forth in SEQ ID NO: 3.

| Cysteine residue ID after Edelman[a] | anti-PD-1 mAb HC Residue (position in SEQ ID NO: 3) |
|---|---|
| I | 22 |
| II | 96 |
| III | 130 |
| IV | 143 |
| V | 199 |
| VI | 222 |
| VII | 225 |
| VIII | 257 |
| IX | 317 |

TABLE 1-continued

Expected residues involved in disulfide linkages of an exemplary anti-PD-1 antibody agent heavy chain having an amino acid sequence as set forth in SEQ ID NO: 3.

| Cysteine residue ID after Edelman[a] | anti-PD-1 mAb HC Residue (position in SEQ ID NO: 3) |
|---|---|
| X | 363 |
| XI | 421 |

TABLE 2

Expected residues involved in disulfide linkages of an exemplary anti-PD-1 antibody agent light chain having an amino acid sequence as set forth in SEQ ID NO: 4.

| Cysteine residue ID after Edelman[a] | anti-PD-1 mAb LC Residue (position in SEQ ID NO: 4) |
|---|---|
| I | 23 |
| II | 88 |
| III | 134 |
| IV | 194 |
| V | 214 |

This exemplary anti-PD-1 antibody exhibits an occupied N-glycosylation site at asparagine residue 293 in the CH2 domain of each heavy chain in the mature protein sequence (SEQ ID NO:3). The expressed N-glycosylation at this site is a mixture of oligosaccharide species typically observed on IgGs expressed in mammalian cell culture, for example, shown below is the relative abundance of glycan species from a preparation of this exemplary anti-PD-1 antibody cultured in Chinese Hamster Ovary (CHO) cells (Table 3).

TABLE 3

Glycan Analysis of an anti-PD-1 antibody binding agent

| Species | Abundance (% of total oligosaccharide) | Description of Glycan |
|---|---|---|
| G0 | <0.1% | Nonfucosylated agalactobiantennary complex-type oligosaccharide |
| G0F | 19.5% | Core fucosylated agalactobiantennary complex type oligosaccharide |
| G1 | 0.1% | Nonfucosylated monogalactosylated biantennary complex type oligosaccharide |
| G1F | 45.6% | Core fucosylated monogalactosylated biantennary complex type oligosaccharide |
| G2F | 27.4% | Core fucosylated galactosylated biantennary complex type oligosaccharide |
| M5 | 0.5% | Oligomannosidic N-glycan, $Man_5GlcNAc_2$ |

In some embodiments, the present disclosure provides an anti-PD-1 antibody agent comprising at least one immunoglobulin heavy chain having an amino acid sequence as set forth in SEQ ID NO: 3 and at least one immunoglobulin light chain having an amino acid sequence as set forth in SEQ ID NO: 4. In some embodiments an anti-PD-1 antibody agent comprises two immunoglobulin heavy chains, each having an amino acid sequence as set forth in SEQ ID NO: 3. Alternatively or additionally, in some embodiments an anti-PD-1 antibody agent comprises two immunoglobulin light chains, each having an amino acid sequence as set forth in SEQ ID NO: 4. In some embodiments, an anti-PD-1 antibody agent has a canonical antibody format.

In some embodiments, a PD-1-binding agent is nivolumab, pembrolizumab, atezolizumab, durvalumab, avelumab, or any of the antibodies disclosed in WO2014/179664.

Pembrolizumab is an anti-PD-1 monoclonal antibody ("mAb") (also known as MK-3475, SCH 9000475, Keytruda). Pembrolizumab is an immunoglobulin G4/kappa isotype humanized mAb. The mechanism of pembrolizumab consists of the mAb binding to the PD-1 receptor of lymphocytes to block the interaction of PD-1 with PD-L1 and PD-L2 ligands produced by other cells in the body, including tumor cells of certain cancers.

Similarly to pembrolizumab, nivolumab (also known as BMS-936558, Opdivo) was first approved by the FDA in 2014 to treat melanoma that cannot be surgically removed or has metastasized following treatment with ipilimumab and a BRAF inhibitor where appropriate.

In some embodiments, a PD-1 antibody agent is as disclosed in International Patent Application Publication WO2014/179664, the entirety of which is incorporated herein.

In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin.

In some embodiments, a PD-1-binding agent is glycosylated and one or more sites. As used herein, "glycan" is a sugar polymer (moiety) component of a glycoprotein. The term "glycan" encompasses free glycans, including glycans that have been cleaved or otherwise released from a glycoprotein. In some embodiments, present disclosure provides a composition comprising one or more glycoforms of a heavy chain, light chain, and/or antibody agent as described herein. In some embodiments, a glycan is N-linked to an Fc region. In some embodiments, a PD-1-binding agent is glycosylated at Asn297 (Kabat numbering).

The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform." In some embodiments, a provided composition comprises a plurality of glycoforms of one or more of an heavy chain, light chain, and/or antibody agent as described herein.

In some embodiments a PD-1-binding agent binds with high affinity to human and cynomolgus monkey PD-1. In some embodiments, binding of a PD-1-binding agent can be characterized by surface plasma resonance (SPR). In some embodiments, SPR measurements may demonstrate or confirm binding of a PD-1 binding agent a to human and/or a cynomolgus monkey PD-1 Fc fusion. In some embodiments, a PD-1-binding agent binds human and cynomolgus PD-1 with a fast association rate, slow dissociation rate, and high affinity (Table 4). For example, with an exemplary PD-1-binding agent, binding kinetics to human and cynomolgus monkey PD-1 were similar, with less than a 2-fold difference in $K_D$ values. In addition, binding of an exemplary PD-1-binding agent to human or cynomolgus monkey PD-1 expressed on CHO-K1 cells was assessed by flow cytometry. An exemplary PD-1-binding agent was determined to bind to cell surface human and cynomolgus PD-1 with an $EC_{50}$ of 2.0 and 3.4 nM, respectively.

TABLE 4

Binding of a PD-1-binding agent (comprising SEQ ID NOs: 1 and 2) to PD-1 as determined by Surface Plasma Resonance and bind to PD-1 Expressing CHO cells

| Species | Kinetic Parameters (SPR) | | | PD-1 expressing CHO cells $EC_{50}$ (nM) |
|---|---|---|---|---|
| | $K_{assoc}$ $(Ms)^{-1}$ | $K_{dissoc}$ $(s^{-1})$ | $K_D$ (nM) | |
| Human PD-1 | $5.7 \times 10^5$ | $1.7 \times 10^{-4}$ | 0.30 | 2.0 |
| Cyno PD-1 | $4.3 \times 10^5$ | $2.3 \times 10^{-4}$ | 0.53 | 3.4 |

CHO = Chinese hamster ovary; cyno = cynomolgus monkey, $EC_{50}$ = half-maximal effective concentration; $K_{assoc}$ = association rate constant; $K_D$ = dissociation constant; $K_{dissoc}$ = dissociation rate constant; PD-1 = programmed cell death-1; SPR = surface plasma resonance.

In some embodiments, antagonist activity of a PD-1-binding agent in blocking the PD-1/PD-L1 or PD-L2 interaction may be confirmed or determined using a flow cytometry-based assay that measured binding of labeled PD-L1 and PD-L2 expressed as a mouse IgG1 Fc fusion proteins (PD-L1 mFc or PD-L2 mFc) to PD-1-expressing cells. In some embodiments, a PD-1-binding agent can efficiently block PD-1/PD-L1 and PD-1/PD-L2 binding compared to an IgG4 isotype control.

In some embodiments, a PD-1-binding agent can effectively neutralize PD-1 activity (e.g., can inhibit binding of PD-1 to PD-L1 and PD-L2). In some embodiments, functional antagonist activity of a PD-1-binding agent may be confirmed or determined in a mixed lymphocyte reaction (MLR) demonstrating enhanced interleukin (IL)-2 production upon addition of a PD-1-binding agent. In some embodiments, a MLR assay may be carried out using primary human CD4+ T cells as responders and human dendritic cells as stimulators.

Expression and Formulation

In some embodiments, a PD-1-binding agent is expressed from a vector comprising one or more nucleic acid sequences. In some embodiments, a PD-1-binding agent comprises an immunoglobulin heavy chain polypeptide that is encoded by a nucleotide sequence which comprises SEQ ID NO: 5.

SEQ ID NO: 5
GAG GTG CAG CTG TTG GAG TCT GGG GGA GGC TTG GTA

CAG CCT GGG GGG TCC CTG AGA CTC TCC TGT GCA GCC

TCT GGA TTC ACT TTC AGT AGC TAT GAC ATG TCT TGG

GTC CGC CAG GCT CCA GGG AAG GGG CTG GAG TGG GTC

TCA ACC ATT AGT GGT GGT GGT AGT TAC ACC TAC TAT

CAA GAC AGT GTG AAG GGG CGG TTC ACC ATC TCC AGA

GAC AAT TCC AAG AAC ACG CTG TAT CTG CAA ATG AAC

AGC CTG AGA GCC GAG GAC ACG GCC GTA TAT TAC TGT

GCG TCC CCT TAC TAT GCT ATG GAC TAC TGG GGG CAA

GGG ACC ACG GTC ACC GTC TCC TCA GCA TCC ACC AAG

GGC CCA TCG GTC TTC CCG CTA GCA CCC TGC TCC AGG

AGC ACC TCC GAG AGC ACA GCC GCC CTG GGC TGC CTG

GTC AAG GAC TAC TTC CCC GAA CCA GTG ACG GTG TCG

```
TGG AAC TCA GGC GCC CTG ACC AGC GGC GTG CAC ACC

TTC CCG GCT GTC CTA CAG TCC TCA GGA CTC TAC TCC

CTC AGC AGC GTG GTG ACC GTG CCC TCC AGC AGC TTG

GGC ACG AAG ACC TAC ACC TGC AAC GTA GAT CAC AAG

CCC AGC AAC ACC AAG GTG GAC AAG AGA GTT GAG TCC

AAA TAT GGT CCC CCA TGC CCA CCA TGC CCA GCA CCT

GAG TTC CTG GGG GGA CCA TCA GTC TTC CTG TTC CCC

CCA AAA CCC AAG GAC ACT CTC ATG ATC TCC CGG ACC

CCT GAG GTC ACG TGC GTG GTG GTG GAC GTG AGC CAG

GAA GAC CCC GAG GTC CAG TTC AAC TGG TAC GTG GAT

GGC GTG GAG GTG CAT AAT GCC AAG ACA AAG CCG CGG

GAG GAG CAG TTC AAC AGC ACG TAC CGT GTG GTC AGC

GTC CTC ACC GTC CTG CAC CAG GAC TGG CTG AAC GGC

AAG GAG TAC AAG TGC AAG GTC TCC AAC AAA GGC CTC

CCG TCC TCC ATC GAG AAA ACC ATC TCC AAA GCC AAA

GGG CAG CCC CGA GAG CCA CAG GTG TAC ACC CTG CCC

CCA TCC CAG GAG GAG ATG ACC AAG AAC CAG GTC AGC

CTG ACC TGC CTG GTC AAA GGC TTC TAC CCC AGC GAC

ATC GCC GTG GAG TGG GAG AGC AAT GGG CAG CCG GAG

AAC AAC TAC AAG ACC ACG CCT CCC GTG CTG GAC TCC

GAC GGC TCC TTC TTC CTC TAC AGC AGG CTA ACC GTG

GAC AAG AGC AGG TGG CAG GAG GGG AAT GTC TTC TCA

TGC TCC GTG ATG CAT GAG GCT CTG CAC AAC CAC TAC

ACA CAG AAG AGC CTC TCC CTG TCT CTG GGT AAA
```

In some embodiments, a PD-1-binding agent comprises an immunoglobulin light chain polypeptide that is encoded by a nucleotide sequence which comprises SEQ ID NO: 6.

```
                                               SEQ ID NO: 6
GAC ATC CAG TTG ACC CAG TCT CCA TCC TTC CTG TCT

GCA TAT GTA GGA GAC AGA GTC ACC ATC ACT TGC AAG

GCC AGT CAG GAT GTG GGT ACT GCT GTA GCC TGG TAT

CAG CAA AAA CCA GGG AAA GCC CCT AAG CTC CTG ATC

TAT TGG GCA TCC ACC CTG CAC ACT GGG GTC CCA TCA

AGG TTC AGC GGC AGT GGA TCT GGG ACA GAA TTC ACT

CTC ACA ATC AGC AGC CTG CAG CCT GAA GAT TTT GCA

ACT TAT TAC TGT CAG CAT TAT AGC AGC TAT CCG TGG

ACG TTT GGC CAG GGG ACC AAG CTG GAG ATC AAA CGG

ACT GTG GCT GCA CCA TCT GTC TTC ATC TTC CCG CCA

TCT GAT GAG CAA TTG AAA TCT GGA ACT GCC TCT GTT

GTG TGC CTG CTG AAT AAC TTC TAT CCC AGA GAG GCC

AAA GTA CAG TGG AAG GTG GAT AAC GCC CTC CAA TCG
```

```
GGT AAC TCC CAG GAG AGT GTC ACA GAG CAG GAC AGC

AAG GAC AGC ACC TAC AGC CTC AGC AGC ACC CTG ACG

CTG AGC AAA GCA GAC TAC GAG AAA CAC AAA GTC TAC

GCC TGC GAA GTC ACC CAT CAG GGC CTC AGC TCG CCC

GTC ACA AAG AGC TTC AAC AGG GGA GAG TGT
```

In some embodiments, a PD-1 binding agent is expressed from a vector comprising one or more nucleic acid sequences encoding a PD-1-binding immunoglobulin heavy chain variable domain polypeptide and/or a PD-1-binding immunoglobulin light chain variable domain polypeptide. In some embodiments, a PD-1 binding agent is expressed from a vector comprising one or more nucleic acid sequences encoding a PD-1-binding immunoglobulin heavy chain polypeptide and/or a PD-1-binding immunoglobulin light chain polypeptide. The vector can be, for example, a plasmid, episome, cosmid, viral vector (e.g., retroviral or adenoviral), or phage. Suitable vectors and methods of vector preparation are well known in the art (see, e.g., Sambrook et al., Molecular Cloning, a Laboratory Manual, 3rd edition, Cold Spring Harbor Press, Cold Spring Harbor, N.Y. (2001), and Ausubel et al, Current Protocols in Molecular Biology, Greene Publishing Associates and John Wiley & Sons, New York, N.Y. (1994)).

In some embodiment, vector(s) for expression of PD-1-binding agents further comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, Gene Expression Technology: Methods in Enzymology, Vol. 185, Academic Press, San Diego, Calif. (1990).

The vector(s) comprising the nucleic acid(s) encoding PD-1-binding agents of the present disclosure can be introduced into a host cell that is capable of expressing the polypeptides encoded thereby, including any suitable prokaryotic or eukaryotic cell. Some preferable qualities of host cells include easy and reliable growth, a reasonably fast growth rate, having well-characterized expression systems, and/or ease/efficient transformation or transfection.

In some embodiments, mammalian cells are utilized. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al, Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70).

Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al, Proc. Natl. Acad. Sci. USA, 85: 1581-1585 (1988)), Raji cells (CCL-86), and derivatives thereof.

In some embodiments, a PD-1-binding agent is formulated as a pharmaceutical composition, containing one or a combination of monoclonal antibodies, or antigen-binding portion(s) thereof, formulated with a pharmaceutically acceptable carrier. An anti-PD-1 antibody agent may be formulated alone or in combination with other drugs (e.g., as an adjuvant). For example, a PD-1-binding agent can be administered in combination with other agents for the treatment or prevention of the diseases disclosed herein (e.g., cancer).

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it may be useful to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the ease of sterile powders is the preparation of sterile injectable solutions, such methods of preparation may include vacuum drying and freeze-drying (lyophilization) to yield a powder of the active ingredient plus any additional desired ingredient from a previously sterile-filtered solution thereof.

In some embodiments, a therapeutic composition is formulated as a sterile liquid. In some embodiments, the composition is free from visible particles. In some embodiments, the composition is formulated in a buffer (e.g., a citrate buffer). In some embodiments, the composition comprises a PD-1-binding agent and two or more of the following: citrate, arginine, sodium chloride and polysorbate 80.

In some embodiments, a therapeutic composition of the present disclosure (e.g., a PD-1 binding agent) is aseptically filled into a clear glass vial. In some embodiments, such a glass vial is stoppered with a chlorobutyl elastomer stopper laminated with fluoropolymer and sealed with an aluminum overseal.

In some embodiments, a PD-1 binding agent is stored at 2-8° C. In some embodiments, a drug product of the present disclosure is free of preservatives.

General Protocol

As described herein, provided methods comprise administering a PD-1 binding agent to a patient, a subject, or a population of subjects according to a regimen that achieves clinical benefit.

Provided methods can provide various benefits (e.g., a clinical benefit). In embodiments, a method described herein achieves a clinical benefit. In embodiments, a clinical benefit is stable disease (SD). In embodiments, a clinical benefit is a partial response (PR). IN embodiments, a clinical benefit is a complete response (CR).

In embodiments, a combination therapy achieves a clinical benefit for each therapy administered to a patient. For example, a combination therapy may improve a clinical benefit obtained with a PD-1 inhibitor (e.g., any anti-PD-1 antibody described herein).

In embodiments, a patient or subject is an animal. In embodiments, a patient or subject is a human.

In some embodiments, the regimen comprises at least one parental dose of a PD-1 binding agent. In some embodiments, the regimen comprises a plurality of parental doses.

In some embodiments, the parental dose is an amount of a PD-1 binding agent is within a range of about 5 to about 5000 mg (e.g., about 5 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 2000 mg, about 3000 mg, about 4000 mg, about 5000 mg, or a range defined by any two of the foregoing values). In some embodiments, the parental dose of a PD-1 binding agent is 500 mg or 1000 mg.

In some embodiments, the dose is in an amount relative to body weight. In some embodiments, the parental dose of a PD-1 binding agent is within a range of about 0.01 mg/kg to 100 mg/kg of animal or human body weight; however, doses below or above this exemplary range are within the scope of the invention. The daily parenteral dose can be about 0.01 mg/kg to about 50 mg/kg of total body weight (e.g., about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 12 mg/kg, about 15 mg/kg, about 20 mg/kg, or a range defined by any two of the foregoing values).

In some embodiments, a composition that delivers a PD-1-binding agent (e.g., an anti-PD-1 antibody) is administered to a patient at a dose of about 1, 3 or 10 mg/kg. In some embodiments, a PD-1-binding agent (e.g., an anti-PD-1 antibody) is administered according to a regimen that delivers a dose of about 1, 3 or 10 mg/kg every two weeks. In some embodiments, a PD-1-binding agent (e.g., an anti-PD-1 antibody) is administered according to a regimen that delivers a dose of about 1, 3 or 10 mg/kg every three weeks. In some embodiments, a PD-1-binding agent (e.g., an anti-PD-1 antibody) is administered according to a regimen that delivers a dose of about 1, 3 or 10 mg/kg every four weeks. In some embodiments, a PD-1-binding agent (e.g., an anti-PD-1 antibody) is administered according to a regimen that delivers a dose of about 1 mg/kg every three weeks. In some embodiments, a PD-1-binding agent (e.g., an anti-PD-1 antibody) is administered according to a regimen that delivers a dose of about 3 mg/kg every three weeks. In some embodiments, a PD-1-binding agent (e.g., an anti-PD-1 antibody) is administered according to a regimen that delivers a dose of about 10 mg/kg every three weeks.

In some embodiments, a composition that delivers a PD-1-binding agent (e.g., an anti-PD-1 antibody) is administered to a patient at a dose of about 400 mg. In some embodiments, a PD-1-binding agent (e.g., an anti-PD-1 antibody) is administered according to a regimen that delivers a dose of about 400 mg every two weeks. In some embodiments, a PD-1-binding agent (e.g., an anti-PD-1 antibody) is administered according to a regimen that delivers a dose of about 400 mg every three weeks. In some embodiments, a PD-1-binding agent (e.g., an anti-PD-1 antibody) is administered according to a regimen that delivers a dose of about 400 mg every four weeks.

In some embodiments, a composition that delivers a PD-1-binding agent (e.g., an anti-PD-1 antibody) is administered to a patient at a dose of about 500 mg. In some embodiments, a PD-1-binding agent (e.g., an anti-PD-1 antibody) is administered according to a regimen that delivers a dose of about 500 mg every two weeks. In some embodiments, a PD-1-binding agent (e.g., an anti-PD-1 antibody) is administered according to a regimen that delivers a dose of about 500 mg every three weeks. In some embodiments, a PD-1-binding agent (e.g., an anti-PD-1 antibody) is administered according to a regimen that delivers a dose of about 500 mg every four weeks.

In some embodiments, a composition that delivers a PD-1-binding agent (e.g., an anti-PD-1 antibody) is administered to a patient at a dose of about 800 mg. In some embodiments, a PD-1-binding agent (e.g., an anti-PD-1 antibody) is administered according to a regimen that delivers a dose of about 800 mg every three weeks. In some embodiments, a PD-1-binding agent (e.g., an anti-PD-1 antibody) is administered according to a regimen that delivers a dose of about 800 mg every four weeks. In some embodiments, a PD-1-binding agent (e.g., an anti-PD-1 antibody) is administered according to a regimen that delivers a dose of about 800 mg every six weeks. In some embodiments, a PD-1-binding agent (e.g., an anti-PD-1 antibody) is administered according to a regimen that delivers a dose of about 800 mg every eight weeks.

In some embodiments, a composition that delivers a PD-1-binding agent (e.g., an anti-PD-1 antibody) is administered to a patient at a dose of about 1,000 mg. In some embodiments, a PD-1-binding agent (e.g., an anti-PD-1 antibody) is administered according to a regimen that delivers a dose of about 1,000 mg every three weeks. In some embodiments, a PD-1-binding agent (e.g., an anti-PD-1 antibody) is administered according to a regimen that delivers a dose of about 1,000 mg every four weeks. In some embodiments, a PD-1-binding agent (e.g., an anti-PD-1 antibody) is administered according to a regimen that delivers a dose of about 1,000 mg every five weeks. In some embodiments, a PD-1-binding agent (e.g., an anti-PD-1 antibody) is administered according to a regimen that delivers a dose of about 1,000 mg every six weeks. In some embodiments, a PD-1-binding agent (e.g., an anti-PD-1 antibody) is administered according to a regimen that delivers a dose of about 1,000 mg every seven weeks. In some embodiments, a PD-1-binding agent (e.g., an anti-PD-1 antibody) is administered according to a regimen that delivers a dose of about 1,000 mg every eight weeks. In some embodiments, a PD-1-binding agent (e.g., an anti-PD-1 antibody) is administered according to a regimen that delivers a dose of about 1,000 mg every nine weeks.

In some embodiments, a PD-1-binding agent (e.g., an anti-PD-1 antibody) is administered according to a regimen that delivers a dose of about 500 mg every three weeks. In some embodiments, a PD-1-binding agent (e.g., an anti-PD-1 antibody) is administered according to a regimen that delivers a dose of about 1000 mg every six weeks.

In some embodiments, a PD-1-binding agent (e.g., an anti-PD-1 antibody) is administered according to a regimen that delivers a first dose of PD-1-binding agent for the first 2-6 dosing cycles (e.g., the first 3, 4, or 5 dosing cycles), and then delivers a second dose of a PD-1-binding agent for the subsequent dosing cycles until therapy is discontinued (e.g., due to disease progression or an adverse effect or as directed by a physician). In some embodiments, the duration of the first set of 2-6 dosing cycles (e.g., the first 3, 4, or 5 dosing cycles) is different from the duration of the subsequent dosing cycles. In embodiments, a PD-1-binding agent (e.g., an anti-PD-1 antibody) is administered according to a regimen that delivers a first dose of PD-1-binding agent once every three weeks for the first three dosing cycles, and then delivers a second dose of a PD-1-binding agent once every six weeks or more for the remaining dosing cycles (e.g., a second dose of a PD-1-binding agent once every six weeks for the remaining dosing cycles). In embodiments, a PD-1-binding agent (e.g., an anti-PD-1 antibody) is administered according to a regimen that delivers a first dose of PD-1-binding agent once every three weeks for the first four dosing cycles, and then delivers a second dose of a PD-1-binding agent once every six weeks or more for the remaining dosing cycles (e.g., a second dose of a PD-1-binding agent once every six weeks for the remaining dosing cycles). In embodiments, a PD-1-binding agent (e.g., an anti-PD-1 antibody) is administered according to a regimen that delivers a first dose of PD-1-binding agent once every three weeks for the first five dosing cycles, and then delivers a second dose of a PD-1-binding agent once every six weeks or for the remaining dosing cycles (e.g., a second dose of a PD-1-binding agent once every six weeks for the remaining dosing cycles). In some embodiments, a PD-1-binding agent (e.g., an anti-PD-1 antibody) is administered according to a regimen that delivers a first dose of PD-1-binding agent once every three weeks for the first 2-6 dosing cycles (e.g., the first 3, 4, or 5 dosing cycles), and then delivers a second dose of a PD-1-binding agent once every six weeks or until therapy is discontinued (e.g., due to disease progression or an adverse effect or as directed by a physician). In some embodiments, a PD-1-binding agent (e.g., an anti-PD-1 antibody) is administered according to a regimen that delivers a first dose of a PD-1-binding agent once every three weeks for the first 3, 4, or 5 dosing cycles (e.g., the first 4 dosing cycles), and then delivers a second dose of a PD-1-binding agent once every six weeks or more until therapy is discontinued (e.g., due to disease progression or an adverse effect or as directed by a physician). In embodiments, the method comprises delivering a second dose of PD-1 binding agent once every six weeks until therapy is discontinued.

In some embodiments the first and/or second dose of a PD-1-binding agent (e.g., an anti-PD-1 antibody) is about 100 mg to about 2,000 mg (e.g., about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg). In some embodiments the first dose and the second dose are the same. In some embodiments, the first dose and the second dose are different. In embodiments, the first dose is about 500 mg of a PD-1-binding agent (e.g., an anti-PD-1 antibody). In embodiments, the first dose is about 1000 mg of a PD-1-binding agent (e.g., an anti-PD-1 antibody).

In some embodiments, a PD-1-binding agent (e.g., an anti-PD-1 antibody) is administered according to a regimen that comprises administering an about 500 mg dose every 3 weeks for four doses followed by administering at least one about 1,000 mg dose every six weeks after the fourth dose of about 500 mg. In some embodiments, additional about 1,000 mg doses are administered every six weeks after the first about 1000 mg dose until no further clinical benefit is achieved. In some particular embodiments, a PD-1 binding agent (e.g., an anti-PD1 antibody) is administered according to a dosing regimen that includes 500 mg for 4 cycles Q3W followed by 1000 mg Q6W.

In some embodiments, a PD-1-binding agent (e.g., an anti-PD-1 antibody) is administered according to a regimen that comprises administering a 400 mg dose every 3 weeks for four doses followed by administering at least one 800 mg dose every six weeks after the fourth 400 mg dose. In some embodiments, additional 800 mg doses are administered every six weeks after the first 800 mg dose until no further clinical benefit is achieved. In some particular embodiments, a PD-1 binding agent (e.g., an anti-PD1 antibody) is administered according to a dosing regimen that includes 400 mg for 4 cycles Q3W followed by 800 mg Q6W.

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention.

The desired dosage can be delivered by a single bolus administration of the composition, by multiple bolus administrations of the composition, or by continuous infusion administration of the composition.

In some embodiments, a PD-1 binding agent is administered to a patient or population of subjects who has exhibited response to prior therapy. In some embodiments, the patient or population of subjects has exhibited response to a prior cancer therapy.

In some embodiments, a PD-1 binding agent is administered to a patient or population of subjects who has not exhibited response to prior therapy. In some embodiments, the patient or population of subjects has not received or exhibited response to a prior cancer therapy.

In embodiments, a subject is resistant to treatment with an agent that inhibits PD-1. In embodiments, a subject is refractory to treatment with an agent that inhibits PD-1. In embodiments, a method described herein sensitizes the subject to treatment with an agent that inhibits PD-1.

In embodiments, an anti-PD-1 therapy as described herein is administered in combination with one or more additional therapies (e.g., therapies as described herein). That is, a subject is treated with an anti-PD-1 therapy and one or more additional therapies is administered to a subject such that the subject receives each therapy.

In embodiments, an additional therapy is surgery. In embodiments, an additional therapy is radiotherapy. In embodiments, an additional therapy is chemotherapy. In embodiments, an additional therapy is immunotherapy.

In some embodiments, a PD-1 binding agent is administered simultaneously or sequentially with an additional therapeutic agent, such as, for example, another antibody agent (e.g., an antibody agent that binds to lymphocyte-activation gene 3 (LAG-3) or T-cell immunoglobulin domain and mucin domain 3 protein (TIM-3)) and/or a chemotherapeutic agent (e.g., niraparib). In some embodiments, a PD-1 binding agent is administered before, during, or after administration of an additional therapeutic agent. In some embodiments, a PD-1 binding agent is administered before, during, or after administration of a chemotherapeutic agent (e.g., niraparib).

An anti-PD-1 antibody agent may be administered alone or in combination with other drugs (e.g., as an adjuvant). For example, the PD-1 binding agent can be administered in combination with other agents for the treatment or prevention of the diseases disclosed herein (e.g., cancer). In this respect, the PD-1 binding agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery.

Administration of a PD-1 binding agent simultaneously or sequentially with an additional therapeutic agent is referred to herein as "combination therapy." In combination therapy, a PD-1 binding agent can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional therapeutic agent to a subject in need thereof. In some embodiments a PD-1 binding agent and an additional therapeutic agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

PARP Inhibitors

In embodiments, an additional therapy is a poly (ADP-ribose) polymerase (PARP) inhibitor.

In embodiments, a PARP inhibitor inhibits PARP-1 and/or PARP-2. In some embodiments, the agent is a small molecule, a nucleic acid, a polypeptide (e.g., an antibody), a carbohydrate, a lipid, a metal, or a toxin. In related embodiments, the agent is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), 0N02231, PD 128763, R 503, R554, rucaparib (RUBRACA) (AG-014699, PF-01367338), SBP 101, SC 101914, simmiparib, talazoparib (BMN-673), veliparib (ABT-888), WW 46, 2-(4-(trifluoromethyl)phenyl)-7,8-dihydro-5H-thiopyrano[4,3-d]pyrimidin-4-ol, and salts or derivatives thereof. In some related embodiments, an agent is niraparib, olaparib, rucaparib, talazoparib, veliparib, or salts or derivatives thereof. In certain embodiments, an agent is niraparib or a salt or derivative thereof. In certain embodiments, an agent is olaparib or a salt or derivative thereof. In certain embodiments, an agent is rucaparib or a salt or derivative thereof. In certain embodiments, an agent is talazoparib or a salt or derivative thereof. In certain embodiments, an agent is veliparib or a salt or derivative thereof.

Niraparib, (3 S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. See WO 2008/084261 (published on Jul. 17, 2008), WO 2009/087381 (published Jul. 16, 2009), and PCT/US17/40039 (filed Jun. 29, 2017), the entirety of each of which is hereby incorporated by reference. Niraparib can be prepared according to Scheme 1 of WO 2008/084261.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate. The molecular structure of the tosylate monohydrate salt of niraparib is shown below:

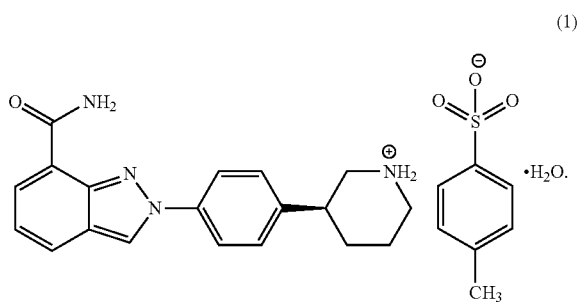

(1)

Niraparib is a potent and selective PARP-1 and PARP-2 inhibitor with inhibitory concentration at 50% of control $(IC_{50})$=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control $(IC_{90})$ of about 4 and 50 nM, respectively.

In embodiments, niraparib is administered at a dose equivalent to about 100 mg of niraparib free base (e.g., a pharmaceutically acceptable salt of niraparib such as niraparib tosylate monohydrate is administered at a dose equivalent to about 100 mg of niraparib free base). In embodiments, niraparib is administered at a dose equivalent to about 200 mg of niraparib free base (e.g., a pharmaceutically acceptable salt of niraparib such as niraparib tosylate monohydrate is administered at a dose equivalent to about 200 mg of niraparib free base. In embodiments, niraparib is administered at a dose equivalent to about 300 mg of niraparib free base (e.g., a pharmaceutically acceptable salt of niraparib such as niraparib tosylate monohydrate is administered at a dose equivalent to about 300 mg of niraparib free base).

Checkpoint Inhibitors

In embodiments, an additional therapy is an immunotherapy. In embodiments, an immunotherapy comprises administration of one or more further immune checkpoint inhibitors (e.g., administration of one, two, three, four, or more further immune checkpoint inhibitors).

Exemplary immune checkpoint targets for inhibition include: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, IDO, and CSF-1R. Accordingly, agents that inhibit of any of these molecules can be used in combination with an anti-PD-1 therapy described herein.

In embodiments, a checkpoint inhibitor is a small molecule, a nucleic acid, a polypeptide (e.g., an antibody), a carbohydrate, a lipid, a metal, a toxin, or a binding agent. In embodiments, a checkpoint inhibitor is an antibody, an antibody conjugate, or an antigen-binding fragment thereof.

In embodiments, an immune checkpoint inhibitor is an agent that inhibits TIM-3, CTLA-4, LAG-3, TIGIT, IDO or CSF1R.

In embodiments, an immune checkpoint inhibitor is a TIM-3 inhibitor. In embodiments, a TIM-3 inhibitor is a TIM-3 binding agent (e.g., an antibody, an antibody conjugate, or an antigen-binding fragment thereof). In embodiments, a TIM-3 inhibitor is a TIM-3 inhibitor described in WO 2016/161270, which is hereby incorporated by reference in its entirety. In embodiments, a TIM-3 inhibitor is TSR-022. For example, a TIM-3 inhibitor (e.g., TSR-022) can be administered in a dose of about 1, 3 or 10 mg/kg (e.g., about 1 mg/kg; about 3 mg/kg; or about 10 mg/kg) or a flat dose between about 100-1500 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg).

In embodiments, an immune checkpoint inhibitor is a CTLA-4 inhibitor (e.g., an antibody, an antibody conjugate, or an antigen-binding fragment thereof). In embodiments, a CTLA-4 inhibitor is a small molecule, a nucleic acid, a polypeptide (e.g., an antibody), a carbohydrate, a lipid, a metal, or a toxin. In embodiments, a CTLA-4 inhibitor is a small molecule. In embodiments, a CTLA-4 inhibitor is a CTLA-4 binding agent. In embodiments, a CTLA-4 inhibitor is an antibody, an antibody conjugate, or an antigen-binding fragment thereof. In embodiments, a CTLA-4 inhibitor is ipilimumab (Yervoy), AGEN1884, or tremelimumab.

In embodiments, an immune checkpoint inhibitor is a LAG-3 inhibitor (e.g., an antibody, an antibody conjugate, or an antigen-binding fragment thereof). In embodiments, a LAG-3 inhibitor is a small molecule, a nucleic acid, a polypeptide (e.g., an antibody), a carbohydrate, a lipid, a metal, or a toxin. In embodiments, a LAG-3 inhibitor is a small molecule. In embodiments, a LAG-3 inhibitor is a LAG-3 binding agent. In embodiments, a LAG-3 inhibitor is an antibody, an antibody conjugate, or an antigen-binding fragment thereof. In embodiments, a LAG-3 inhibitor is a IMP321, BMS-986016, GSK2831781, Novartis LAG525, or a LAG-3 inhibitor described in WO 2016/126858, WO 2017/019894, or WO 2015/138920, each of which is hereby incorporated by reference in its entirety.

In embodiments, an immune checkpoint inhibitor is a TIGIT inhibitor (e.g., an antibody, an antibody conjugate, or an antigen-binding fragment thereof). In embodiments, a TIGIT inhibitor is a small molecule, a nucleic acid, a polypeptide (e.g., an antibody), a carbohydrate, a lipid, a metal, or a toxin. In embodiments, a TIGIT inhibitor is small molecule. In embodiments, a TIGIT inhibitor is a TIGIT binding agent. In embodiments, a TIGIT inhibitor is an antibody, an antibody conjugate, or an antigen-binding fragment thereof. In embodiments, a TIGIT inhibitor is MTIG7192A, BMS-986207, or OMP-31M32.

In embodiments, an immune checkpoint inhibitor is an IDO inhibitor. In embodiments, an IDO inhibitor is a small molecule, a nucleic acid, a polypeptide (e.g., an antibody), a carbohydrate, a lipid, a metal, or a toxin. In embodiments, an IDO inhibitor is small molecule. In embodiments, an IDO inhibitor is an IDO binding agent. In embodiments, an IDO inhibitor is an antibody, an antibody conjugate, or an antigen-binding fragment thereof.

In embodiments, an immune checkpoint inhibitor is a CSF1R inhibitor. In embodiments, a CSF1R inhibitor is a small molecule, a nucleic acid, a polypeptide (e.g., an antibody), a carbohydrate, a lipid, a metal, or a toxin. In embodiments, a CSF1R inhibitor is small molecule. In embodiments, a CSF1R inhibitor is a CSF1R binding agent. In embodiments, a CSF1R inhibitor is an antibody, an antibody conjugate, or an antigen-binding fragment thereof.

In embodiments, a checkpoint inhibitor (e.g., a TIM-3 inhibitor such as TSR-022) can be administered in a dose of about 1, 3 or 10 mg/kg (e.g., about 1 mg/kg; about 3 mg/kg; or about 10 mg/kg) or a flat dose between about 100-1500 mg (e.g., a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg).

In embodiments, an anti-PD-1 agent is administered in combination with at least one additional immune checkpoint inhibitor or at least two or at least three additional checkpoint inhibitors. In embodiments, a PARP inhibitor is further administered.

In embodiments, an anti-PD-1 agent is administered in combination with a TIM-3 inhibitor, and a LAG-3 inhibitor. In embodiments, an anti-PD-1 agent is administered in combination with a TIM-3 inhibitor, a LAG-3 inhibitor, and a CTLA-4 inhibitor.

In embodiments, an anti-PD-1 agent is administered in combination with a LAG-3 inhibitor and a PARP inhibitor (e.g., niraparib). In embodiments, an anti-PD-1 agent is administered in combination with a TIM-3 inhibitor, a LAG-3 inhibitor and a PARP inhibitor (e.g., niraparib).

For female patients of childbearing potential, it is preferable that the patient have a negative serum pregnancy test within 72 hours prior to the date of administration of the first dose of an anti-PD-1 binding agent. It is also preferable that female patients of childbearing potential and male patients agree to use 2 adequate methods of contraception with their partner. In some embodiments, a patient agrees to use 2 methods of contraception starting with the screening visit through 150 days after the last dose of study therapy.

Measuring Tumor Response

In some embodiments, a clinical benefit is a complete response ("CR"), a partial response ("PR") or a stable disease ("SD"). In some embodiments, a clinical benefit corresponds to at least SD. In some embodiments, a clinical benefit corresponds to at least a PR. In some embodiments, a clinical benefit corresponds to a CR. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, at least 5% of patients achieve a clinical benefit. In some embodiments, at least 5% of patients achieve SD. In some embodiments, at least 5% of patients achieve at least a PR. In some embodiments, at least 5% of patients achieve CR. In some embodiments, at least 20% of patients achieve a clinical benefit. In some embodiments, at least 20% of patients achieve SD.

In some embodiments, the clinical benefit (e.g., SD, PR and/or CR) is determined in accordance with Response Evaluation Criteria in Solid Tumors (RECIST). In some embodiments, the clinical benefit (e.g., SD, PR and/or CR) is determined in accordance RECIST guidelines.

In some embodiments, tumor response can be measured by, for example, the RECIST v 1.1 guidelines. The guidelines are provided by E. A. Eisenhauer, et al., "New response evaluation criteria in solid tumors: Revised RECIST guideline (version 1.1.)," *Eur. J. of Cancer*, 45: 228-247 (2009), which is incorporated by reference in its entirety. In some embodiments, RECIST guidelines may serve as a basis for all protocol guidelines related to disease status. In some embodiments, RECIST guidelines are used to assess tumor response to treatment and/or date of disease progression.

RECIST guidelines require, first, estimation of the overall tumor burden at baseline, which is used as a comparator for subsequent measurements. Tumors can be measured via use of any imaging system known in the art, for example, by a CT scan, or an X-ray. Measurable disease is defined by the presence of at least one measurable lesion. In studies where the primary endpoint is tumor progression (either time to progression or proportion with progression at a fixed date), the protocol must specify if entry is restricted to those with measurable disease or whether patients having non-measurable disease only are also eligible.

When more than one measurable lesion is present at baseline, all lesions up to a maximum of five lesions total (and a maximum of two lesions per organ) representative of all involved organs should be identified as target lesions and will be recorded and measured at baseline (this means in instances where patients have only one or two organ sites involved a maximum of two and four lesions respectively will be recorded).

Target lesions should be selected on the basis of their size (lesions with the longest diameter), be representative of all involved organs, but in addition should be those that lend themselves to reproducible repeated measurements.

Lymph nodes merit special mention since they are normal anatomical structures which may be visible by imaging even if not involved by tumor. Pathological nodes which are defined as measurable and may be identified as target lesions must meet the criterion of a short axis of P15 mm by CT scan. Only the short axis of these nodes will contribute to the baseline sum. The short axis of the node is the diameter normally used by radiologists to judge if a node is involved by solid tumor. Nodal size is normally reported as two dimensions in the plane in which the image is obtained (for CT scan this is almost always the axial plane; for MRI the plane of acquisition may be axial, sagittal or coronal). The smaller of these measures is the short axis.

For example, an abdominal node which is reported as being 20 mm. 30 mm has a short axis of 20 mm and qualifies as a malignant, measurable node. In this example, 20 mm should be recorded as the node measurement. All other pathological nodes (those with short axis P10 mm but <15 mm) should be considered non-target lesions. Nodes that have a short axis <10 mm are considered non-pathological and should not be recorded or followed.

A sum of the diameters (longest for non-nodal lesions, short axis for nodal lesions) for all target lesions will be calculated and reported as the baseline sum diameters. If lymph nodes are to be included in the sum, then as noted above, only the short axis is added into the sum. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent', or in rare cases 'unequivocal progression.' In addition, it is possible to record multiple nontarget lesions involving the same organ as a single item on the case record form (e.g., 'multiple enlarged pelvic lymph nodes' or 'multiple liver metastases').

In some embodiments, tumor response can be measured by, for example, the immune-related RECIST (irRECIST) guidelines, which include immune related Response Criteria (irRC). In irRC, measurable lesions are measured that have at least one dimension with a minimum size of 10 mm (in the longest diameter by CT or MRI scan) for nonnodal lesions and greater than or equal to 15 mm for nodal lesions, or at least 20 mm by chest X-ray.

In some embodiments, Immune Related Response Criteria include CR (complete disappearance of all lesions (measurable or not, and no new lesions)); PR (decrease in tumor burden by 50% or more relative to baseline); SD (not meeting criteria for CR or PR in the absence of PD); or PD (an increase in tumor burden of at 25% or more relative to nadir). Detailed description of irRECIST can be found at Bohnsack et al., (2014) ESMO, ABSTRACT 4958 and Nishino et al., (2013) *Clin. Cancer Res.* 19(14): 3936-43.

In some embodiments, tumor response can be assessed by either irRECIST or RECIST version 1.1. In some embodiments, tumor response can be assessed by both irRECIST and RECIST version 1.1.

Pharmacokinetics

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, a patient population includes one or more subjects ("a population of subjects") suffering from metastatic disease.

In some embodiments, a patient population includes one or more subjects that is suffering from or susceptible to cancer. In some embodiments, the cancer is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, the cancer is endometrial cancer, NSCLC, renal cancer, melanoma, cervical cancer, squamous cell carcinoma (e.g., of the lung) or colorectal cancer. In some embodiments, a patient population includes one or more subjects (e.g., comprises or consists of subjects) suffering from cancer. For example, in some embodiments, a patient population suffering from cancer may have previously been treated with a prior therapy, for example, radiation and/or chemotherapy.

In some embodiments, the pharmacokinetic parameter(s) can be any parameters suitable for describing the present composition. For example, in some embodiments, the $C_{max}$ is about 1 µg/ml; about 5 µg/ml, about 10 µg/ml, about 15 µg/ml, about 20 µg/ml, about 25 µg/ml, about 30 µg/ml, about 35 µg/ml, about 40 µg/ml, about 45 µg/ml, about 50 µg/ml, about 55 µg/ml, about 60 µg/ml, about 65 µg/ml, about 70 µg/ml, about 75 µg/ml, about 80 µg/ml, about 85 µg/ml, about 90 µg/ml, about 95 µg/ml, about 100 µg/ml, about 150 µg/ml, about 200 µg/ml, about 250 µg/ml, about 300 µg/ml, or any other $C_{max}$ appropriate for describing a pharmacokinetic profile of a PD-1 binding agent.

In some embodiments, the $T_{max}$ is, for example, not greater than about 0.5 hours, not greater than about 1.0 hours, not greater than about 1.5 hours, not greater than about 2.0 hours, not greater than about 2.5 hours, or not greater than about 3.0 hours, or any other $T_{max}$ appropriate for describing a pharmacokinetic profile of a PD-1 binding agent.

In general, AUC as described herein is the measure of the area under the curve that corresponds to the concentration of an analyte over a selected time period following administration of a dose of a therapeutic agent. In some embodiments, such time period begins at the dose administration (i.e., 0 hours after dose administration) and extends for about 2, about 6, about 12, about 36, about 48, about 72, about 168, about 336, about 514, about 682, or more hours after the dose administration. In some embodiments, AUC is that achieved from 0 hours to 336 hours following administration of a dose described herein.

The $AUC_{(0-336\ h)}$ can be, for example, about 500 µg·hr/mL, about 1000 µg·hr/mL, about 1500 µg·hr/mL, about 2000 µg·hr/mL, about 2500 µg·hr/mL, about 3000 µg·hr/mL, about 3500 µg·hr/mL, about 4000 µg·hr/mL, about 4500 µg·hr/mL, about 5000 µg·hr/mL, about 7500 µg·hr/mL, about 10,000 µg·hr/mL, about 15,000 µg·hr/mL, about 20,000 µg·hr/mL, about 25,000 µg·hr/mL, about 30,000 µg·hr/mL, about 35,000 µg·hr/mL, about 40,000 µg·hr/mL, about 45,000 µg·hr/mL, about 50,000 µg·hr/mL, about 65,000 µg·hr/mL, about 75,000 µg·hr/mL, about 90,000 µg·hr/mL, or any other $AUC_{(0-336\ h)}$ appropriate for describing a pharmacokinetic profile of a therapeutic agent (e.g., a PD-1 binding agent). In some embodiments, a PD-1-binding agent (e.g., an anti-PD-1 antibody) is administered according to a regimen that is demonstrated to achieve an average $AUC_{0-336\ h}$ of PD-1-binding agent concentration-time curve in a patient population that is within 2500 h*µg/mL to 50000 h*µg/mL. In some embodiments, the regimen is demonstrated to achieve an average $AUC_{0-336\ h}$ of PD-1-binding agent concentration-time curve in a patient population that is about 3400 h*µg/mL, about 11000 h*µg/mL, or about 36800 h*µg/mL.

In some embodiments, the AUC from 0 hours to the end of the dosing period is determined ($AUC_{(0-Tau)}$). In some embodiments, the dosing period is one week, two weeks, three weeks, four weeks, five weeks, six weeks, seven weeks, eight weeks, nine weeks or ten weeks. In some embodiments, the dosing period is 3 weeks. In some embodiments, the dosing period is six weeks.

In some embodiments, a PD-1-binding agent is administered according to a regimen demonstrated to achieve a response rate in relevant patient population such that no more than 50% to 80% of patients show progressive disease after 2, 4, 6, 8, 10, 12, 14, 16, 18, or 20 weeks following initiation of treatment. In some embodiments, no more than 80% of patients show progressive disease after at least 10 weeks following initiation of treatment.

In some embodiments, a PD-1-binding agent is administered according to a regimen that is sufficient to achieve an average PD-1 receptor occupancy of at least 50% to 90% after 1, 2, 3, 4, or 5 days following a single dose of the composition. In some embodiments, administration of a composition that delivers a PD-1-binding agent sufficient to achieve an average PD-1 receptor occupancy of at least 85% after 3 days following a single dose of the composition.

In some embodiments, a PD-1-binding agent is administered according to a regimen sufficient to achieve an average stimulation ratio of at least 1 in a functional PD-1 receptor occupancy assay after 3 days following a single dose of the PD-1-binding agent.

In some embodiments, a PD-1-binding agent is administered according to a regimen sufficient to achieve an average PD-1 receptor occupancy of at least 75% over a first period of time, e.g., about 14 days to about 60 days following a single dose of the PD-1-binding agent. In some embodiments, a PD-1-binding agent is administered according to a regimen sufficient to achieve an average PD-1 receptor occupancy of at least 75% over the first period of time (e.g., about 15 days to about 60 days; in some embodiments about 29 days) following a single dose of the PD-1-binding agent.

In some embodiments, a PD-1-binding agent is administered according to a regimen sufficient to achieve an average stimulation ratio of at least 1 in a functional PD-1 receptor occupancy assay over a first period of time, e.g., about 14 days to about 60 days following a single dose of the PD-1-binding agent. In some embodiments, a PD-1-binding agent is administered according to a regimen sufficient to achieve an average stimulation ratio of at least 1 in a functional PD-1 receptor occupancy assay over the first period of time (e.g., about 15 days to about 60 days; in some embodiments about 29 days) following a single dose of the PD-1-binding agent.

EXAMPLES

The following examples are provided to illustrate, but not limit the claimed invention.

Example 1. Dosing Regimens for an Exemplary PD-1-Binding Agent

This example describes a multicenter, open-label, first-in-human Phase 1 study evaluating a PD-1 binding agent (an anti-PD-1 antibody), in patients with tumors. Specifically, this example describes dosage effects of treatment with a particular PD-1 binding agent in patients, and in particular patients with advanced solid tumors or metastatic solid tumors. A PD-1 binding agent as described in the present study comprises a humanized monoclonal anti-PD-1 antibody. Specifically, a particular PD-1 binding agent that comprises a heavy chain variable region comprising CDR sequences of SEQ ID NOs: 9, 10, and 11 and a light chain variable region comprising CDR sequences of SEQ ID NOs: 12, 13, and 14. This exemplary anti-PD-1 antibody utilizes a human IGHG4*01 heavy chain gene, and a human IGKC*01 kappa light chain gene, as scaffolds. Further, there is a single Ser to Pro point mutation in the hinge region of the IgG4 heavy chain at the canonical S228 position.

Patients were included with histologically or cytologically proven advanced (unresectable) or metastatic solid tumor and who had disease progression after treatment with available therapies that are known to confer clinical benefit or who are intolerant to other known treatment(s).

This study comprises 2 parts: dose escalation and cohort expansion. Part 1 of the study (dose escalation) is intended, inter alia, to evaluate the safety, PK, and PDy profile, tolerability and anti-cancer effect of the anti-PD-1 antibody. A modified 3+3 design was used for dose escalation at 1 mg/kg, 3 mg/kg, and 10 mg/kg every 2 weeks (Q2W). Dose escalation continued to a maximally administered dose of 10 mg/kg Q2W and a MTD was not identified. No DLTs were observed. Preliminary safety findings indicate that the exemplary PD-1-binding agent is safe and well tolerated.

Part 2 of the study is intended, inter alia, are to evaluate safety and tolerability, PK, and PDy profile of the anti-PD-1 antibody at fixed doses of 400 mg or 500 mg administered every 3 weeks (Q3W) and 800 mg or 1000 mg administered every 6 weeks (Q6W) by using a modified 6+6 design. Part 2 of this study assesses the effects in patients who have certain tumor types, such as: endometrial cancer in separate cohorts consisting of MSS tumors and MSI-H tumors, triple negative breast cancer, ovarian cancer, NSCLC, and squamous cell carcinoma of the anogenital region (e.g., squamous cell carcinoma of the anus, penis, cervix, vagina, or vulva).

Pharmacokinetic parameters of a PD-1-binding agent in patients administered different doses were determined. As described herein, a least 18 patients were enrolled in the study, with at least 12 subjected in the dose-limiting toxicity (DLT) evaluation cohorts and at least 6 subjects in the PK/PDy cohorts. The clearance of a PD-1-binding agent was determined in patients following single IV infusion. Administration was done through a 30 minute IV infusion. The log-linear mean serum concentration versus time following a single dose of the anti-PD-1 antibody at concentrations of 1 mg/kg, 3 mg/kg and 10 mg/kg are each shown in FIG. 1 and FIG. 2, panel A.

Figure 3:
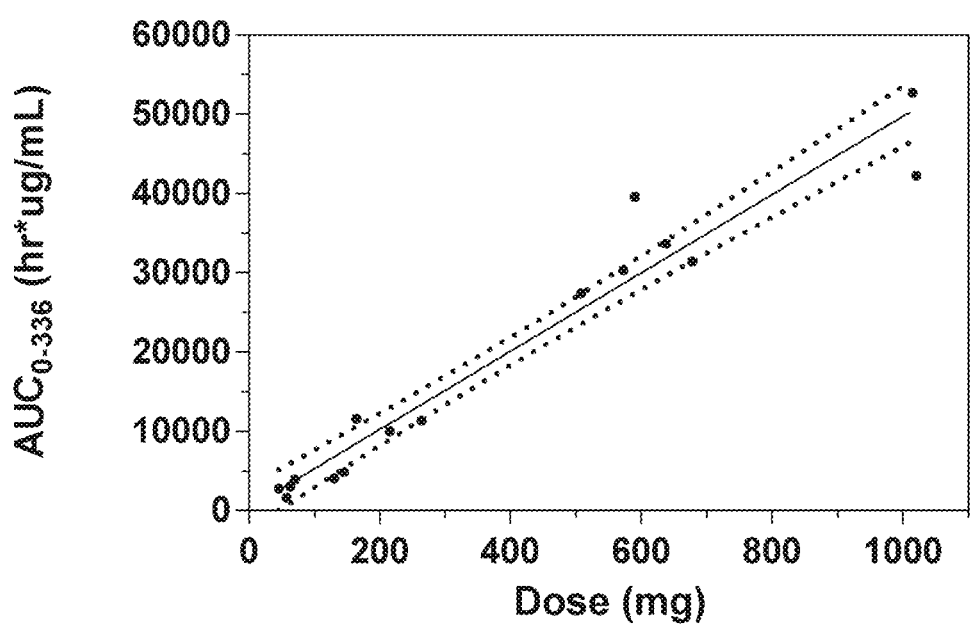
FIG. 3 depicts a graphical representation of dose and exposure relationship of an exemplary anti-PD-1 antibody. $AUC_{0-336\ hr}$(hr*μg/mL) was used as a model for exposure and was observed to increase linearly with dosage of anti-PD-1 antibody.

This anti-PD-1 antibody treatment exhibited dose proportional PK across all dose groups tested, see Table 5. The mean $C_{max}$ was approximately 21, 66, and 224 μg/mL and the mean $AUC_{0-336\ h}$ was approximately 3378, 10999, and 39303 h*μg/mL for dose levels 1, 3 and 10 mg/kg, respectively. The time of peak serum concentration ranged from 0.5-3 hours for all three treatment groups with median at 1.5 hours. The mean clearances were 0.201, 0.117 and 0.152 mL/h/kg for 1, 3, and 10 mg/kg dose groups, respectively. Terminal half-life ranged from approximately 201 to 438 hours. Moreover, as shown in FIG. 3, an exemplary anti-PD-1 antibody exhibited exposure, as assessed by $C_{max}$ and AUC, that was linearly proportional to dose.

TABLE 5

Mean Pharmacokinetic Parameters for Treatment Groups of PD-1-binding agent
(with a heavy chain variable region comprising CDR sequences of SEQ ID NOs: 9, 10, and
11 and a light chain variable region comprising CDR sequences of SEQ ID NOs: 12, 13, and
14) after intravenous infusion to patients.

| Dose (mg/kg) | $C_{max}$ (μg/mL) | $C_{336\,h}$ (μg/mL) | $t_{max}$ (h) | $t_{1/2}$ (h) | $AUC_{0\text{-}336\,h}$ (h × μg/mL) | $V_{ss}$ (mL/kg) | CL (mL/h/kg) |
|---|---|---|---|---|---|---|---|
| 1 mg/kg (n = 6) | 21.4 ± 4.43 | 5.99 ± 2.38 | 1.5 (0.5-3.0) | 311 ± 149 | 3378 ± 1141 | 74.2 ± 23.7 | 0.201 ± 0.121 |
| 3 mg/kg (n = 3) | 66.4 ± 6.25 | 23.4 ± 1.52 | 1.5 (1.5-3.0) | 438 ± 114 | 10,999 ± 841 | 71.7 ± 11.4 | 0.117 ± 0.010 |
| 10 mg/kg (n = 11) | 244 ± 52.7 | 76.6 ± 25.1 | 1.5 (1.5-3.0) | 317 ± 155 | 39,303 ± 10,301 | 60.7 ± 16.6 | 0.152 ± 0.052 |

Abbreviations:
$AUC_{0\text{-}336\,h}$ = area under the concentration-time curve from 0 to 336 hours;
$C_{336\,h}$ = concentration at 336 hours;
CL = clearance;
$C_{max}$ = maximum concentration;
n = number;
PD-1 = programmed cell death-1;
SD = standard deviation;
$t_{1/2}$ = half-life;
$t_{max}$ = time to reach maximum concentration;
$V_{ss}$ = volume of distribution at steady state.
Note:
Data are presented as mean ± SD for $C_{max}$, $C_{336\,h}$, $t_{1/2}$, $AUC_{0\text{-}336\,h}$, $V_{ss}$ and CL values and median (range) for $t_{max}$ values.

After repeat doses of a PD-1-binding agent in two week cycles (Q2W), PK profiles of 2 patients in 1 mg/kg group and 2 patients in 3 mg/kg group reached the steady state after 3 doses. The accumulation ratio based on concentration at the end of the dosage interval ($C_{trough}$) ranged from 1.45 to 2.93.

Figure 4:
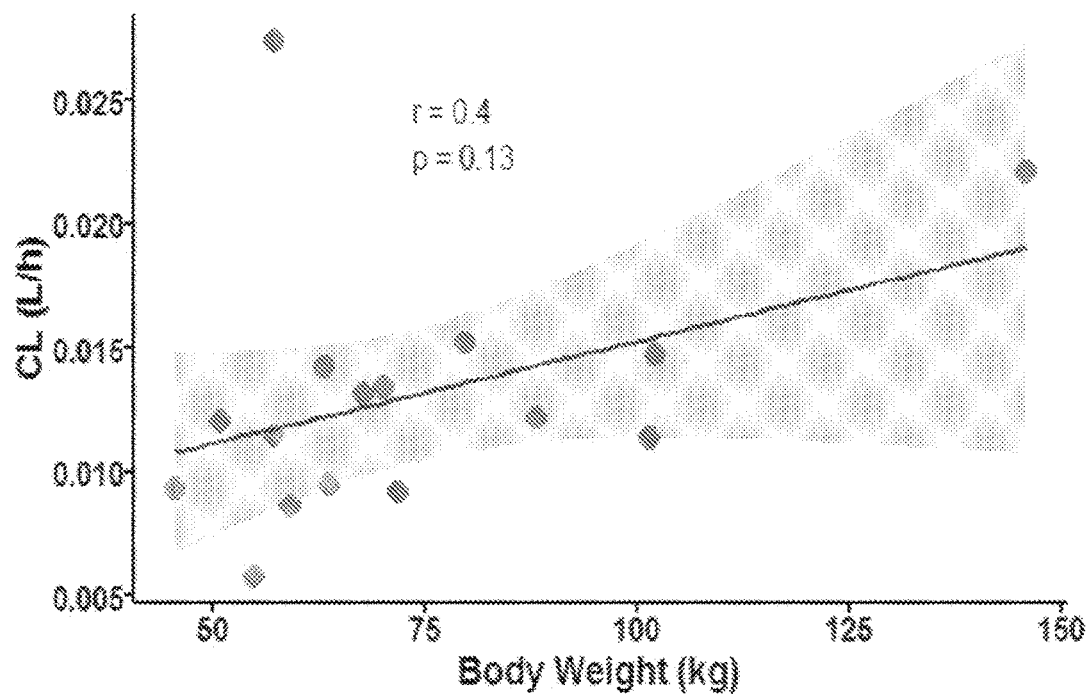
FIG. 4 depicts a graphical representation of clearance and body weight relationship. Body weight was not found to be a significant covariant for clearance of an anti-PD-1 antibody.

For selection of fixed doses, a two compartmental model was used to describe the observed PK data and predict the appropriate dose and regimen. The effect of body weight on clearance of a PD-1-binding agent was also explored. Body weight over a range of 45 kg to 146 kg was found not to be a significant covariant for clearance (See, FIG. 4). Full receptor occupancy was achieved at serum concentrations of anti-PD-1 antibody of 2.43 μg/ml and above. The model predicted $C_{trough}$ at steady state for the 500 mg Q3W and 1000 mg Q6W are 51.1 and 29.2 μg/mL with 90% confidence interval of (13.4, 111.1) and (4.1, 78.5), respectively. The projected mean and 90% lower bound of $C_{trough}$ at 500 mg Q3W and 1000 mg Q6W are about 21.0 and 12.0; 5.5 and 1.7 fold higher than the level required for full receptor occupancy of peripheral blood cells. Data assessing the dose and regimes at steady start are provided in Table 6 below.

TABLE 6

Pharmacokinetic parameters for different treatment regimens
with a PD-1-binding agent (with a heavy chain variable region
comprising CDR sequences of SEQ ID NOs: 9, 10, and 11 and
a light chain variable region comprising CDR sequences of
SEQ ID NOs: 12, 13, and 14).

| Dose and Regime | C trough (ug/mL) | 90% Confidence Interval | Cmax (ug/mL) | AUC (0-Tau) (h*ug/mL) |
|---|---|---|---|---|
| 400 mg Q3W | 40.9 | (10.7, 88.9) | 142.9 | 35864 |
| 500 mg Q3W | 51.1 | (13.4, 111.1) | 181.7 | 45445 |
| 80 mg Q6W | 23.4 | (3.3, 62.8) | 230.8 | 66469 |
| 1000 mg Q6W | 29.2 | (4.1, 78.5) | 291.8 | 90848 |

These data support flat dosing, including at 400 mg, 500 mg, 800 mg and/or 1000 mg.

Figure 2:
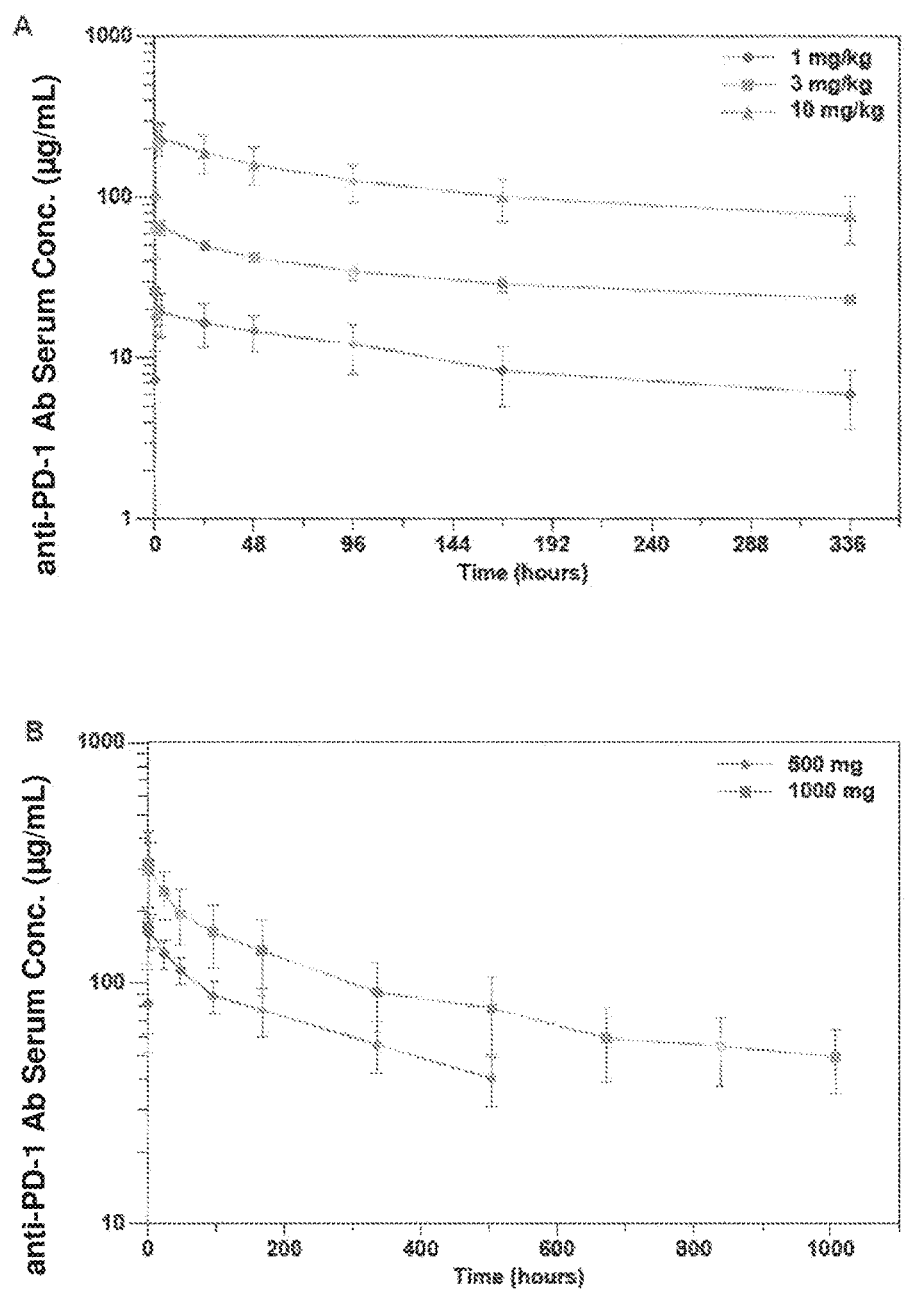
FIGS. 2A-2B depict graphical representations of log-linear mean concentration versus time profile following single dose administrations of an anti-PD-1 antibody at different dosages. (A) Dots represent a dose of 1 mg/kg, squares represent a dose of 3 mg/kg and triangles represent a dose of 10 mg/kg. (B) Dots represent a dose of 500 mg and squares represent a dose of 1000 mg. The x-axes indicates time from administration (in hours) and the y-axes indicates the serum concentration of the anti-PD-1 antibody in μg/mL. Error bars represent ±standard deviation.

Clearance of a PD-1-binding agent after single dose administration of 500 mg and 1000 mg was determined. Log-linear mean serum concentration versus time following a single dose of the anti-PD-1 antibody at concentrations of 500 mg and 1000 mg are shown in FIG. 2, panel B, and single-dose pharmacokinetic summaries are provided in Table 7 below. Mean maximum concentration was approximately 174 and 322 μg/mL for 500 mg Q3W and 1000 mg Q6W, respectively; mean area under the concentration-time curve from 0 to 504 hours ($AUC_{0\text{-}504\,h}$) and $AUC_{0\text{-}1008\,h}$ were approximately 36,424 and 91,376 h×μg/mL, respectively. The time of peak serum concentration ranged from 0.5 to 3.0 hours for both treatment groups, with the median at 1.0 and 1.5 hours, respectively. Serum concentrations of the exemplary PD-1-binding agent observed 3 weeks after the 500 mg dose were comparable to those observed 6 weeks after the 1000 mg dose.

TABLE 7

Mean Pharmacokinetic Parameters for Fixed Dose Treatment
Groups of PD-1-binding agent (with a heavy chain variable
region comprising CDR sequences of SEQ ID NOs: 9, 10, and
11 and a light chain variable region comprising CDR sequences
of SEQ ID NOs: 12, 13, and 14) after intravenous infusion
to patients.

| Dose (mg/kg) | $C_{max}$ (μg/mL) | $C_{last}$ (μg/mL) | $t_{max}$ (h) | $AUC_{0\text{-}last}$ (h × μg/mL) |
|---|---|---|---|---|
| 500 mg (n = 6) | 174 ± 35.2 | 40.2 ± 9.31 | 1.0 (0.5-3.0) | 36,424 ± 6674 |
| 1000 mg (n = 7) | 322 ± 101 | 43.7 ± 18.2[a] | 1.5 (0.5-3.0) | 91,376 ± 26,808 |

$AUC_{0\text{-}last}$ = area under the concentration-time curve from 0 to 504 hours (500 mg cohort) or with/without extrapolated 1008 hours (1000 mg cohort); $C_{last}$ = last measurable plasma concentration; $C_{max}$ = maximum concentration; n = number; Q3W = every 2 weeks; Q6W = every 6 weeks; SD = standard deviation; $t_{max}$ = time to reach maximum concentration; Data are presented as mean ± SD for $C_{max}$, $C_{last}$, $AUC_{0\text{-}last}$ values and median (range) for $t_{max}$ values. $C_{max}$ was measured at 504 hours for 500 mg Q3W group and 1008 hours for 1000 mg Q6W gropu.
[a] n = 5

Example 2. PD-1 Target Engagement of an Exemplary PD-1-Binding Agent

This example describes the ability of an exemplary PD-1-binding agent that is a humanized monoclonal anti-PD-1 antibody to engage with its target (e.g., the PD-1 receptor). Specifically, an exemplary anti-PD-1 antibody that comprises a heavy chain variable region comprising CDR sequences of SEQ ID NOs: 9, 10, and 11 and a light chain variable region comprising CDR sequences of SEQ ID NOs: 12, 13, and 14. Target engagement of an anti-PD-1 antibody agent was determined by measuring PD-1 receptor occupancy in peripheral blood from patients following a first dose with an anti-PD-1 antibody agent. Two assays are being employed: the first assay, termed conventional receptor occupancy (cRO), provides a measure of direct anti-PD-1 antibody agent binding to CD3+ cells and the second assay, termed functional receptor occupancy (fRO), measures IL-2 production by ex vivo stimulated T cells following administration of anti-PD-1 antibody agent.

cRO Assay Results

To measure direct binding in the cRO assay, PBMCs were isolated from patients at baseline as well as on Days 3 and 15 following administration of a first dose of anti-PD-1 antibody agent. Additionally, certain patients additional samples were collected on Days 22 and 29 following the first dose. PD-1—receptor occupancy by an anti-PD-1 antibody agent on circulating CD3+ T cells was measured by flow cytometry.

Following a single dose of the anti-PD-1 antibody agent at 1 mg/kg, 3 mg/kg or 10 mg/kg, the mean percent occupancy on Day 3 across all dose levels is about 90%. Consistent with published data for nivolumab (Brahmer et al., 2010), a mean occupancy of approximately 80% is maintained throughout the first 29 days following a single dose at 1 mg/kg (Table 8; data cut-off 30 Sep. 2016)

TABLE 8

Mean Percent PD-1 Occupancy for anti-PD-1 antibody agent in CD3+ cells at 1, 3 and 10 mg/kg Dose Levels

| Dose | Percent PD-1 Occupancy Mean ± SD (N) | | | | |
|---|---|---|---|---|---|
| | Baseline | Day 3 | Day 15 | Day 22 | Day 29 |
| 1 mg/kg | 3.23 ± 3.12 (6) | 95.6 ± 17.1 (6) | 84.3 ± 4.27 (6) | 82.8 ± 3.67 (3) | 77.8 ± 0.514 (2) |
| 3 mg/kg | 5.75 ± 1.72 (3) | 88.0 ± 5.42 (3) | 85.9 ± 2.49 (3) | ND | ND |
| 10 mg/kg | 2.42 ± 0.898 (5) | 86.9 ± 4.08 (5) | 85.8 ± 7.45 (3) | ND | ND |

Abbreviations: CD = cluster of differentiation; n = number; ND = no data available; PD-1 = programmed cell death-1; SD = standard deviation.

Figure 5:
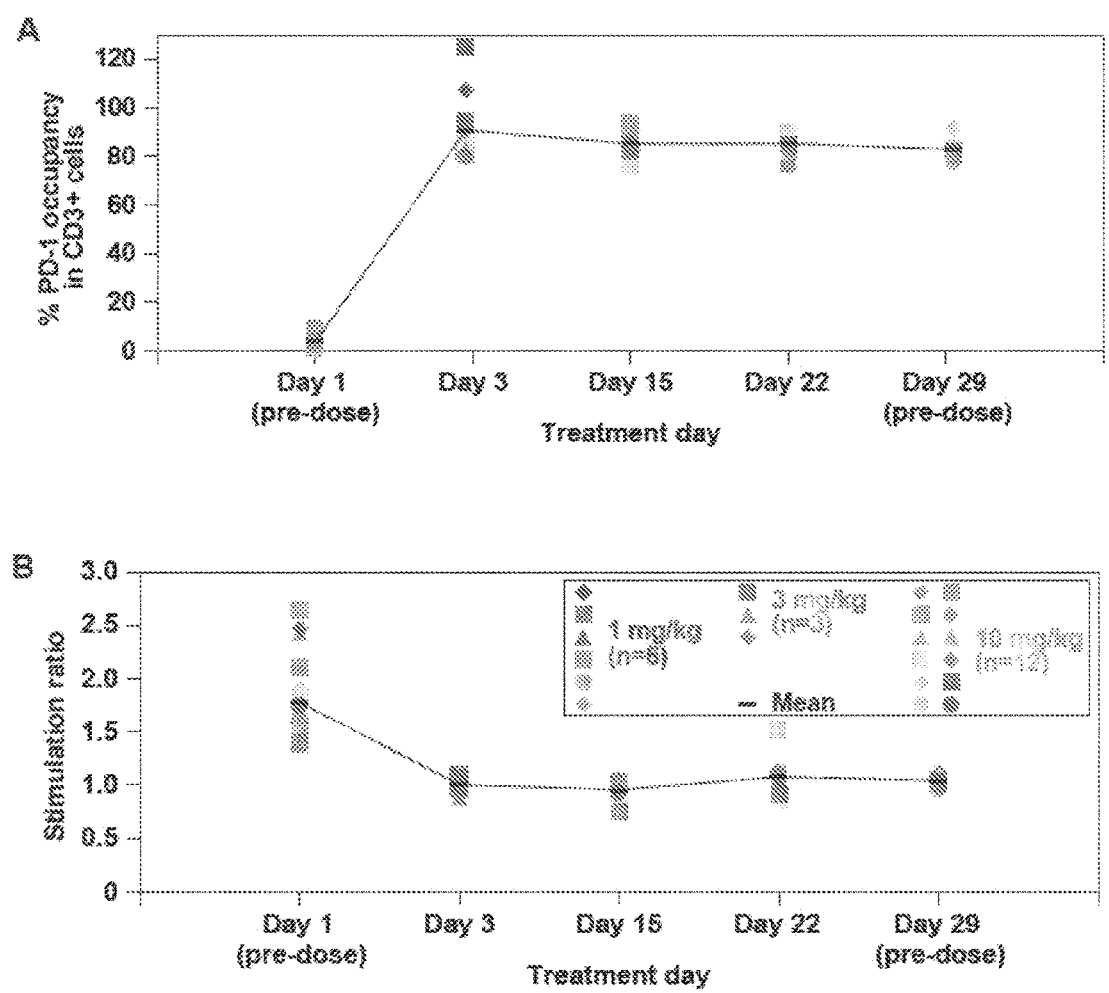
FIGS. 5A-5B depicts results for receptor occupancy assays for 1, 3, and 10 mg/kg doses. Panel A depicts % PD-1 receptor occupancy in CD3+ cells. Panel B depicts the IL-2 stimulation ratio.

Results for receptor occupancy assessed for dosing at 1, 3, and 10 mg/kg dose levels of the exemplary PD-1-binding agent is also shown in FIG. 5, panel A.

Figure 6:
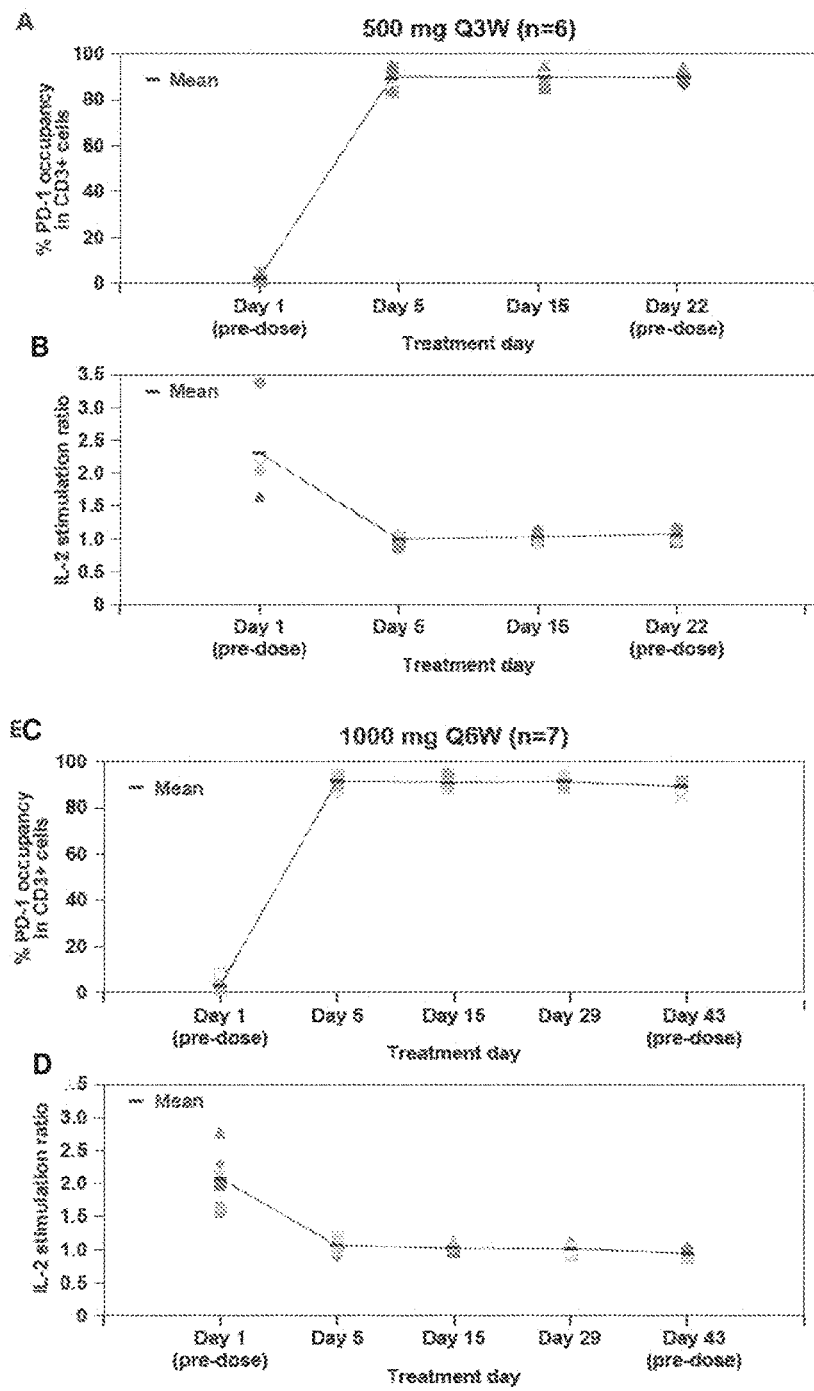
FIGS. 6A-6D depicts results for receptor occupancy assays for 500 mg Q3W and 1000 mg Q6W doses. Panels A and C depict % PD-1 receptor occupancy in CD3+ cells. Panels B and D depict the IL-2 stimulation ratio.

Additionally, PD-1 receptor occupancy as assessed above, was maintained over three and six weeks for fixed dosing levels of 500 mg at Q3W (n=6) and 1000 mg at Q6W (n=7), respectively. Results for receptor occupancy of the exemplary PD-1-binding agent at 500 mg and 1000 mg dose levels are shown in FIG. 6, panels A and C, respectively.

fRO Assay Results

To obtain a functional readout of receptor occupancy in the fRO assay, whole blood was collected at baseline as well as on Days 3 and 15 following the first dose. Additionally, in certain patients, samples were additionally collected on Days 22 and 29 following the first dose. PD-1—receptor occupancy by anti-PD-1 antibody agent on circulating T cells was measured as a function of IL-2 production following ex vivo stimulation with the superantigen staphylococcal enterotoxin B (SEB) in the presence of saturating concentrations of anti-PD-1 antibody agent or isotype control (Patnaik et al., 2015). In this assay an IL-2 ratio of 1 reflects stimulation close to the maximal stimulation and is reflective of maximal receptor occupancy.

Following a single dose of anti-PD-1 antibody agent, a mean IL-2 stimulation ratio of 1 is achieved on Day 3 across all dose levels. A mean IL-2 ratio of approximately 1 is maintained at 29 days following a single dose at 1 mg/kg (Table 9).

TABLE 9

Mean IL-2 Stimulation Ratio in fRO Assay at 1, 3 and 10 mg/kg Dose Levels of anti-PD-1 antibody agent

| Dose | Percent PD-1 Occupancy Mean ± SD (n =) | | | | |
|---|---|---|---|---|---|
| | Baseline | Day 3 | Day 15 | Day 22 | Day 29 |
| 1 mg/kg | 1.69 ± 0.241 (6) | 1.01 ± 0.073 (6) | 1.00 ± 0.0513 (6) | 1.32 ± 0.276 (2) | 1.08 ± 0.064 (2) |
| 3 mg/kg | 1.62 ± 0.236 (3) | 0.927 ± 0.0473 (3) | 0.977 ± 0.0702 (3) | ND | ND |
| 10 mg/kg | 1.86 ± 0.547 (4) | 1.05 ± 0.0603 (3) | 0.860 (1) | ND | ND |

Results for IL-2 stimulation for dosing at 1, 3, and 10 mg/kg dose levels of the exemplary PD-1-binding agent is also shown in FIG. 5, panel B. Additionally, IL-2 stimulation of the exemplary PD-1-binding agent at 500 mg at Q3W (n=6) and 1000 mg at Q6W (n=7) are shown in FIG. 6, panels B and D, respectively.

The receptor occupancy and IL-2 stimulation experiments demonstrate that the PD-1 antibody agent fully binds PD-1 on T cells in the periphery of patients treated at all dose levels tested. The lowest anti-PD-1 antibody agent concentration that resulted in full receptor occupancy was calculated to be 2.43 µg/mL. Moreover, the data demonstrate that the anti-PD-1 antibody agent binding to PD-1 is maintained for at least 29 days following a single dose at 1 mg/kg. These results demonstrate the efficacy and stability of a single dose of an anti-PD-1 antibody agent.

Moreover, for the fixed dosing regimens (500 mg Q3W and 1000 Q6W) the mean $C_{min}$ at which full receptor occupancy was observed was ~2 ug/ml. Taking the receptor occupancy studies in view of the pharmacokinetic data reveals advantageous properties of a dosing schedule for a PD-1-binding agent of 500 mg Q3W followed by 1000 mg Q6W. One benefit of this dosing schedule is that it provides trough concentrations which are at least 20-fold above the lowest concentration at which full peripheral receptor occupancy is achieved (40.2 ug/ml) for 500 mg Q3W and 43.7 µg/mL for 1000 mg Q6W).

The receptor occupancy (RO) for this 500 mg Q3W/1000 mg Q6W fixed dose regimen of the anti-PD-1 antibody also has been studied in patients having MSS endometrial cancer, MSI-H endometrial cancer, and NSCLC.

To measure direct binding in the RO assay, PBMCs were isolated from patients at baseline (Day 1 predose) as well as prior to the second dose (Day 22 predose) on a 500 mg Q3W schedule. PD-1-receptor occupancy by the anti-PD-1 antibody on circulating CD3+ T cells was measured by flow cytometry using a method similar to that previously reported for nivolumab (Brahmer, J C O 2010). PBMCs from treated patients were preincubated ex vivo with a saturating concentration of either unlabeled human IgG4 (isotype control) or the anti-PD-1 antibody. Following washing and staining with anti-CD3 and anti-human IgG4, PD-1 occupancy by the infused anti-PD-1 antibody was estimated as the ratio of CD3+ cells stained with anti-human IgG4 after ex vivo saturation with isotype control antibody (indicating in vivo binding) to that after anti-PD-1 antibody saturation (indicating total available binding sites).

Figure 8:
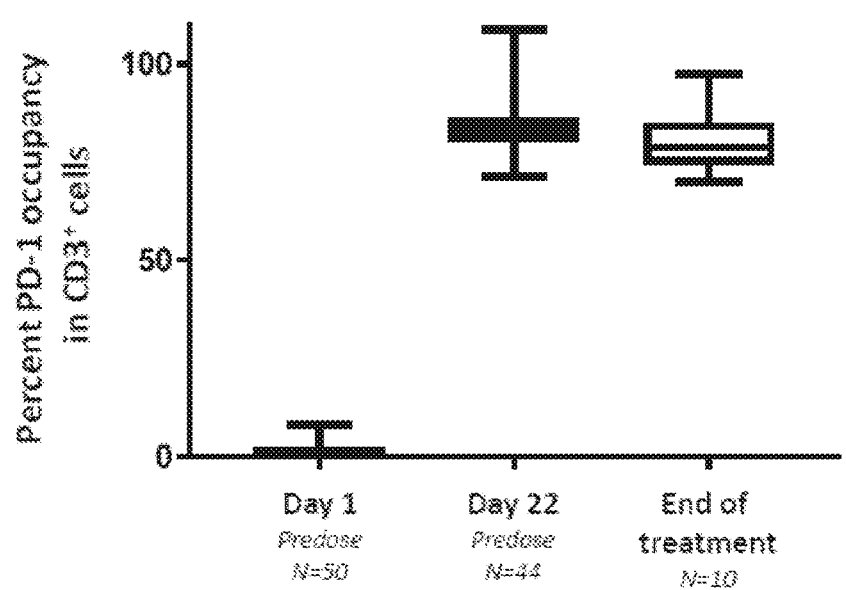
FIG. 8 depicts the percent of PD-1 receptor occupancy by an anti-PD-1 antibody as measured on circulating $CD3^+$ T cells by flow cytometry prior to the first and second 500 mg doses and again at the end of treatment.

Data from the RO assay are shown in FIG. 8, with the number of patients indicated in parentheses. In this plot, the line in the center of the box plot indicates the median, with the box extending to indicate the 25$^{th}$ and 75$^{th}$ percentiles. The bars represent the minimum and maximum values and show that high occupancy of the anti-PD-1 antibody is achieved.

Example 3. Treatment of Patients with an Exemplary PD-1-Binding Agent

This example describes clinical efficacy of an exemplary PD-1-binding agent in cancer patients, e.g., patients with advanced solid tumors. It was found that administration of a PD-1 binding agent by a dosing regimen of the present disclosure conferred clinical benefits to patients. An exemplary PD-1 binding agent as described in the present study is a humanized monoclonal anti-PD-1 antibody. For example, a particular PD-1 binding agent with a heavy chain variable region comprising CDR sequences of SEQ ID NOs: 9, 10, and 11 and a light chain variable region comprising CDR sequences of SEQ ID NOs: 12, 13, and 14 is evaluated. This anti-PD-1 antibody utilizes a human IGHG4*01 heavy chain gene, and a human IGKC*01 kappa light chain gene, as scaffolds. Further, there is a single Ser to Pro point mutation in the hinge region of the IgG4 heavy chain at the canonical 5228 position.

Moreover, it was found that administration of a composition comprising the anti-PD-1 antibody after intravenous infusion conferred clinical benefits to patients, at each of the doses tested. The tumor response in patients that were evaluated as of September 2016 are described in Table 10.

TABLE 10

Tumor Response in patient administered different dosing regimens of a PD-1-binding agent.

| Tumor Type | Cohort | Tumor Response | Intra-Patient Dose Escalation Y/N |
|---|---|---|---|
| Breast adenocarcinoma | 1 mg/kg | PD | |
| Ovarian adenocarcinoma | 1 mg/kg | PD | |
| Parotid Gland | 1 mg/kg | PD | Y |
| Ovarian adenocarcinoma | 3 mg/kg | PR | N |
| Prostate Cancer | 3 mg/kg | PD | |
| Fallopian tube carcinoma | 3 mg/kg | SD | Y |
| TNBC | 1 mg/kg PK/PDy | PD | |
| Ovarian adenocarcinoma | 1 mg/kg PK/PDy | PD | |
| Anal Cancer | 1 mg/kg PK/PDy | SD | Y |
| Peritoneal carcinoma | 10 mg/kg | PD | |
| Breast adenocarcinoma | 10 mg/kg | PD | |
| Small Cell Lung Cancer | 10 mg/kg | PR | |
| Colon Cancer | 10 mg/kg PK/PDy | PD | |
| TNBC | 10 mg/kg PK/PDy | PD | |
| Ovarian adenocarcinoma | 10 mg/kg MTD | PD | |
| Endometrioid ovarian cancer | 10 mg/kg MTD | PD | |
| Esophageal cancer | 10 mg/kg MTD | PD | |
| Pancreatic Cancer | 10 mg/kg PK/Pdy | PD | |
| Ovarian adenocarcinoma | 10 mg/kg PK/Pdy | ND | |
| Ovarian adenocarcinoma | 10 mg/kg PK/Pdy | SD | |
| Cervical cancer | 10 mg/kg PK/Pdy | ND | |

Figure 7:
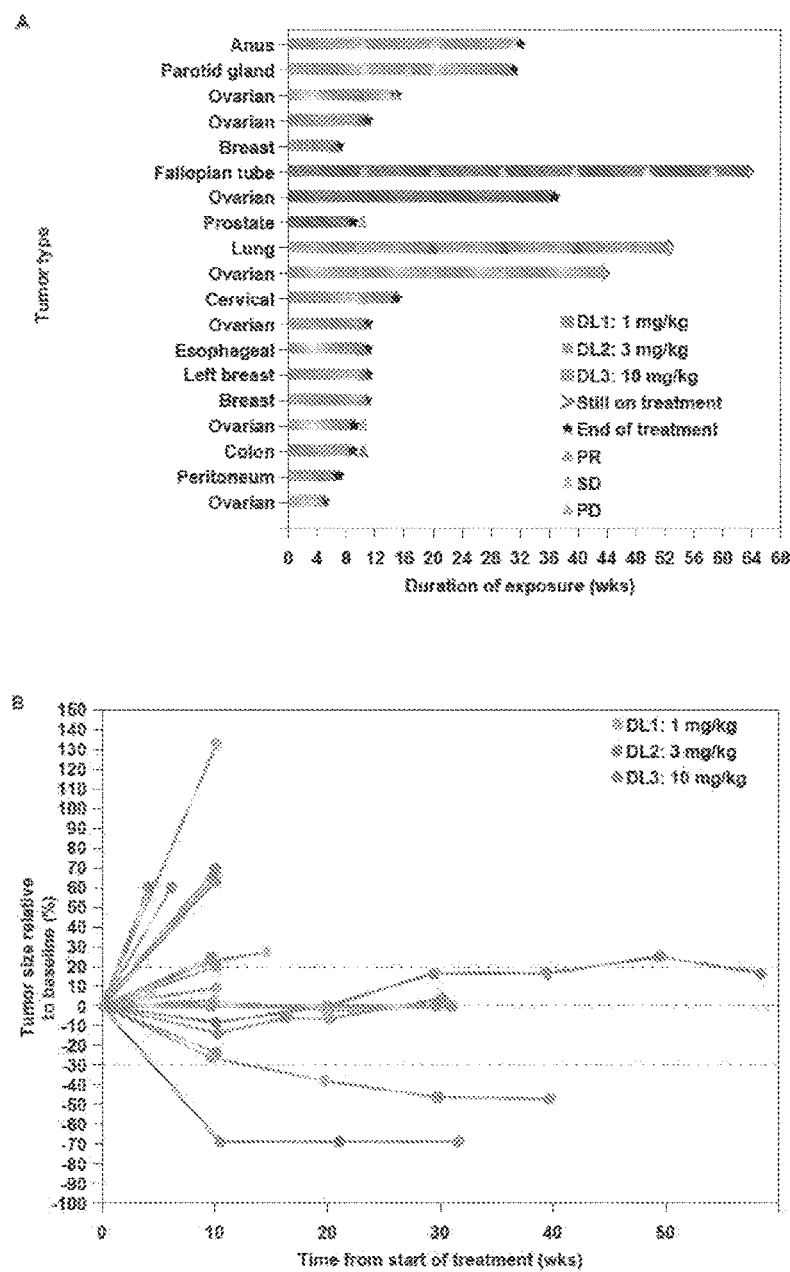
FIGS. 7A-7B depict a summary of treatment responses to an anti-PD-1 antibody. Panel A in FIG. 7 depicts a Swimmer-Lane and panel B shows a Spider Plot of treatment responses to the exemplary PD-1-binding agent.

"PD" = Progressive Disease; "SD" = Stable Disease; "PR" = Partial Response; "ND" = not determined at time of assessment A wide variety of tumor types have been tested thus far including tumors of the anus, rectum, parotid gland, ovaries, breast, fallopian tube, endometrial, uterine, appendix, prostate, lung, cervix, esophagus, peritoneum, kidney, and colon. As of July 2017, 19 patients had a follow-up scan in part 1, and 2 of the 19 patients were categorized as responsive. Both of these 2 patients achieved a PR: one patient with ovarian cancer had a duration of response of 26 weeks and ended treatment at week 36 without progression, and one patient with small cell lung cancer for whom treatment was ongoing, with duration of response ≥31 weeks. Five patients had stable disease, two of whom were continuing treatment (fallopian tube cancer, n=1; ovarian cancer, n=1). Treatment responses are summarized in FIG. 7. Panel A in FIG. 7 depicts a Swimmer-Lane and panel B shows a Spider Plot of treatment responses to the exemplary PD-1-binding agent.

Patients can also receive 500 mg anti-PD-1 antibody every three weeks (Q3W) for the first four cycles followed by 1000 mg every 6 weeks (Q6W) for all subsequent cycles. The effect of a composition this anti-PD-1 antibody administered according to this regimen was studied in patients having MSS endometrial cancer (Table 11). Patients may also receive 500 mg anti-PD-1 antibody every three weeks (Q3W) for the first three cycles followed by 1000 mg every 6 weeks (Q6W) for all subsequent cycles, or patients may receive 500 mg anti-PD-1 antibody every three weeks (Q3W) for the first five cycles followed by 1000 mg every 6 weeks (Q6W) for all subsequent cycles.

TABLE 11

Tumor Assessments in MSS Endometrial Cohort A2

| Best Overall Response by irRECIST | Cohort A2 (N = 25) [n (%)] |
|---|---|
| irCR | 0 |
| irPR | 6 (24) |
| irSD | 7 (28) |

TABLE 11-continued

Tumor Assessments in MSS Endometrial Cohort A2

| Best Overall Response by irRECIST | Cohort A2 (N = 25) [n (%)] |
|---|---|
| irPD | 11 (44) |
| Not evaluable | 0 |
| Not Done | 1 (4) |

Twenty five patients with advanced/recurrent MSS endometrial cancer were treated with the anti-PD-1 antibody and have had at least one CT scan for tumor assessment. These patients are patients who have progress on or after platinum doublet therapy and patients who have received no more than two lines of anti-cancer therapy for recurrent or advanced disease. Of the six patients that achieved irPR, one response has been confirmed. Five patients remain on treatment and one patient has discontinued treatment due to disease progression. These clinical outcomes with the anti-PD-1 antibody are surprising in contrast with previous results using agents such as atezolizumab and pembrolizumab.

The dosing regimen of 500 mg anti-PD-1 antibody every three weeks (Q3W) for the first four cycles followed by 1000 mg every 6 weeks (Q6W) for all subsequent cycles can also be useful for patients with non-small cell lung cancer (NSCLC) and patients with MSI-H cancers (e.g., MSI-H endometrial cancer). Other dosing regimens include 500 mg anti-PD-1 antibody every three weeks (Q3W) for the first three cycles followed by 1000 mg every 6 weeks (Q6W) for all subsequent cycles or 500 mg anti-PD-1 antibody every three weeks (Q3W) for the first five cycles followed by 1000 mg every 6 weeks (Q6W) for all subsequent cycles.

Accordingly, this example demonstrates that the exemplary PD-1-binding agent with a heavy chain variable region comprising CDR sequences of SEQ ID NOs: 9, 10, and 11 and a light chain variable region comprising CDR sequences of SEQ ID NOs: 12, 13, and 14 shows encouraging clinical benefits in patients with diverse cancer types.

Example 4. Treatment of Ovarian Cancer with Exemplary PD-1-Binding Agent in Combination with Niraparib This example describes a clinical trial of niraparib in combination with an anti-PD-1 antibody in first-line maintenance treatment of patients with advanced ovarian cancer who have responded to platinum induction therapy. An exemplary PD-1 binding agent may be a humanized monoclonal anti-PD-1 antibody. For example, a particular a PD-1 binding agent with a heavy chain variable region comprising CDR sequences of SEQ ID NOs: 9, 10, and 11 and a light chain variable region comprising CDR sequences of SEQ ID NOs: 12, 13, and 14 as described in Example 1 may be evaluated.

Patients with histologically or cytologically proven advanced (unresectable) or metastatic solid gynecological tumor (e.g., an ovarian cancer) and who responded to platinum chemotherapy may be included.

Specifically, this study will assess efficacy of treatment of patients with advanced recurrent ovarian cancer with an exemplary PD-1 binding agent in combination with niraparib. The exemplary PD-1 binding agent may comprise a heavy chain variable region with CDR sequences of SEQ ID NOs: 9, 10, and 11 and a light chain variable region with CDR sequences of SEQ ID NOs: 12, 13, and 14 in combination with niraparib. Combination treatment may include 100-300 mg once daily oral administration of niraparib (e.g., one to three capsules of 100 mg strength may be taken at each dose administration). It is envisioned that the PD-1 binding agent may be administered at a dose of 200-1000 mg of a PD-1 antibody agent (e.g., intravenous administration). The exemplary anti-PD-1 antibody may be administered at fixed doses, for example, of 400 mg or 500 mg administered every 3 weeks (Q3W), followed by administration and 800 mg or 1000 mg administered every 6 weeks (Q6W). In some embodiments, a PD-1 antibody agent is administered at a dose of 1, 3, and 10 mg/kg. Treatment cycles may be 14-42 days, e.g., 21 days, 28 days, etc.

Response evaluation criteria in solid tumors (RECIST) tumor assessment via clinically validated imaging methods may be performed at the end of every 1 to 3 cycles until progression.

Patients will continue to receive their assigned treatment until disease progression, unacceptable toxicity, death, withdrawal of consent, and/or lost to follow-up.

Example 5. Treatment of Lung Cancer with Niraparib

This example describes a clinical trial of niraparib alone and/or in combination with an exemplary PD-1 antibody agent for treatment of lung cancer (e.g., NSCLC and/or squamous cell carcinoma). An exemplary PD-1 binding agent may be a humanized monoclonal anti-PD-1 antibody. For example, a particular a PD-1 binding agent with a heavy chain variable region comprising CDR sequences of SEQ ID NOs: 9, 10, and 11 and a light chain variable region comprising CDR sequences of SEQ ID NOs: 12, 13, and 14 as described in Example 1 may be evaluated.

Patients with histologically or cytologically proven advanced (unresectable) or metastatic solid lung cancer (e.g., NSCLS and/or squamous cell carcinoma) may be included. In some embodiments, a patient will have had disease progression after treatment with available therapies that are known to confer clinical benefit or who are intolerant to other known treatment(s).

This study will assess efficacy of treatment of patients with advanced lung cancer with niraparib and/or the exemplary PD-1 binding agent. Patients with advanced lung cancers, for example, squamous cell carcinoma or NSCLC may be treated with niraparib alone and/or in combination with the exemplary PD-1 binding agent. Niraparib treatment may include 100-300 mg once daily oral administration of niraparib (e.g., one to three capsules of 100 mg strength may be taken at each dose administration). It is envisioned that the PD-1 binding agent may be administered at a dose of 200-1000 mg of a PD-1 antibody agent (e.g., intravenous administration). The exemplary anti-PD-1 antibody may be administered at fixed doses of 400 mg or 500 mg administered every 3 weeks (Q3W), followed by administration and 800 mg or 1000 mg administered every 6 weeks (Q6W). In some embodiments, a PD-1 antibody agent is administered at a dose of 1, 3, and 10 mg/kg. Treatment cycles may be 14-42 days, e.g., 21 days, 28 days, etc.

Response evaluation criteria in solid tumors (RECIST) tumor assessment via clinically validated imaging methods may be performed at the end of every 1 to 3 cycles until progression.

Patients will continue to receive their assigned treatment until disease progression, unacceptable toxicity, death, withdrawal of consent, and/or lost to follow-up.

Example 6. Treatment of PD-1 Expressing Lung Cancer with Exemplary PD-1-Binding Agent in Combination with Niraparib This example describes a clinical trial of an exemplary PD-1 antibody agent in combination with niraparib for treatment of lung cancer (e.g., NSCLS and/or squamous cell carcinoma) that expresses PD-1 and/or PD-L1, including subjects whose PD-1 or PDL-1 levels are considered high. An exemplary PD-1 binding agent may be a humanized monoclonal anti-PD-1 antibody. For example, a particular a PD-1 binding agent with a heavy chain variable region comprising CDR sequences of SEQ ID NOs: 9, 10, and 11 and a light chain variable region comprising CDR sequences of SEQ ID NOs: 12, 13, and 14 as described in Example 1 may be evaluated. Efficacy of combination treatment of PD-1/PD-L1 expressing lung cancer with the exemplary PD-1 binding agent in combination with niraparib may be compared with efficacy of treatment with the PD-1 binding agent alone.

Patients with histologically or cytologically proven advanced (unresectable) or metastatic solid lung cancer (e.g., NSCLS and/or squamous cell carcinoma) may be included. In some embodiments, a patient will have had disease progression after treatment with available therapies that are known to confer clinical benefit or who are intolerant to other known treatment(s). In some embodiments the lung cancer is characterized by a high level of expression of PD-1 and/or PD-L1.

This study will assess efficacy of treatment of patients with advanced lung cancer with the exemplary PD-1 binding agent in combination with niraparib compared to treatment with the PD-1 binding agent alone in patients with PD-1/PD-L1 expressing lung cancer. Patients will include those with advanced lung cancers, for example, squamous cell carcinoma or NSCLC. It is envisioned that the PD-1 binding agent may be administered at a dose of 200-1000 mg of a PD-1 antibody agent (e.g., intravenous administration). Niraparib treatment may include 100-300 mg once daily oral administration of niraparib (e.g., one to three capsules of 100 mg strength may be taken at each dose administration). The exemplary anti-PD-1 antibody may be administered at fixed doses of 400 mg or 500 mg administered every 3 weeks (Q3W), followed by administration and 800 mg or 1000 mg administered every 6 weeks (Q6W). In some embodiments, a PD-1 antibody agent is administered at a dose of 1, 3, and 10 mg/kg. Treatment cycles may be 14-42 days, e.g., 21 days, 28 days, etc.

Response evaluation criteria in solid tumors (RECIST) tumor assessment via clinically validated imaging methods may be performed at the end of every 1 to 3 cycles until progression.

Patients will continue to receive their assigned treatment until disease progression, unacceptable toxicity, death, withdrawal of consent, and/or lost to follow-up.

Having thus described at least several aspects and embodiments of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawing are by way of example only and the invention is described in further detail by the claims that follow.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. A method of treating cancer in a human subject, the method comprising:
   administering an immunoglobulin G4 (IgG4) humanized monoclonal anti-Programmed Death-1 (PD-1) antibody, wherein said administering comprises a first dose of 500 mg once every 3 weeks (Q3W) for 4 cycles, followed by a second dose of 1000 mg once every 6 weeks (Q6W); and
   wherein the anti-PD-1 antibody comprises a heavy chain sequence of SEQ ID NO: 3, and a light chain sequence of SEQ ID NO: 4.

2. The method of claim 1, wherein the cancer is:
   (i) a cancer associated with a high tumor mutation burden (TMB);
   (ii) a cancer that is microsatellite stable (MSS),
   (iii) a cancer that is characterized by microsatellite instability,
   (iv) a cancer that has a high microsatellite instability status (MSI-H),
   (v) a cancer that has a low microsatellite instability status (MSI-L),
   (vi) a cancer associated with high TMB and MSI-H,
   (vii) a cancer associated with high TMB and MSI-L or MSS,
   (viii) a cancer that has a defective DNA mismatch repair system,
   (ix) a cancer that has a defect in a DNA mismatch repair gene,
   (x) a hypermutated cancer,
   (xi) a cancer comprising a mutation in polymerase delta (POLD),
   (xii) a cancer comprising a mutation in polymerase epsilon (POLE), or
   (xiii) a cancer that has homologous recombination repair deficiency/homologous repair deficiency ("HRD").

3. The method of claim 1, wherein the human subject is further administered an immune checkpoint inhibitor.

4. The method of claim 3, wherein the immune checkpoint inhibitor is an agent that inhibits T cell immunoglobulin and mucin protein 3 (TIM-3), cytotoxic T-lymphocyte-associated protein 4 (CTLA-4), lymphocyte activation gene-3 (LAG-3), or T cell immunoglobulin and ITIM domain (TIGIT).

5. The method of claim 1, wherein the human subject is further administered an agent that inhibits poly (ADP-ribose) polymerase (PARP).

6. The method of claim 5, wherein the PARP inhibitor is selected from the group consisting of niraparib, olaparib, rucaparib, talazoparib, and veliparib.

7. The method of claim 5, wherein PARP inhibitor is niraparib.

8. The method of claim 1, wherein the human subject has previously been treated with one or more of surgery, radiotherapy, chemotherapy, or immunotherapy.

9. The method of claim 1, wherein the method further comprises administering one or more of surgery, a radiotherapy, a chemotherapy, an immunotherapy, an anti-angiogenic agent, or an anti-inflammatory.

10. The method of claim 1, wherein the cancer is endometrial cancer.

11. The method of claim 1, wherein the human subject is further administered an antibody that binds to TIM-3, CTLA-4, LAG-3, or TIGIT.

12. The method of claim 11, wherein the human subject is further administered an antibody that binds to TIM-3, wherein the antibody is TSR-022.

13. The method of claim 12, wherein TSR-022 is administered at a dose of 300 mg Q3W.

14. A method of treating non-small cell lung cancer (NSCLC) in a human subject, the method comprising:
   administering an IgG4 humanized monoclonal anti-PD-1 antibody, wherein said administering comprises a first dose of 500 mg Q3W for 4 cycles, followed by a second dose of 1000 mg Q6W;
   wherein the anti-PD-1 antibody comprises a heavy chain sequence of SEQ ID NO: 3, and a light chain sequence of SEQ ID NO: 4.

15. The method of claim 14, wherein the human subject is administered TSR-022 at a dose of 300 mg Q3W.

16. A method of treating NSCLC in a human subject, the method comprising:
   administering an IgG4 humanized monoclonal anti-PD-1 antibody at a dose of 500 mg Q3W;
   wherein the anti-PD-1 antibody comprises a heavy chain sequence of SEQ ID NO: 3, and a light chain sequence of SEQ ID NO: 4; and
   wherein the human subject is further administered TSR-022 at a dose of 300 mg Q3W.

\* \* \* \* \*